(12) United States Patent
Ishihara et al.

(10) Patent No.: US 7,427,747 B2
(45) Date of Patent: Sep. 23, 2008

(54) OPTICAL IMAGE PICKUP APPARATUS FOR IMAGING LIVING BODY TISSUE

(75) Inventors: Yasushige Ishihara, Hachioji (JP); Atsushi Okawa, Hachioji (JP); Hiroshi Tosaka, Hachioji (JP); Tianyu Xie, Akiruno (JP); Tadashi Hirata, Hachioji (JP); Akihiro Horii, Hachioji (JP); Kazunari Tokuda, Hachioji (JP)

(73) Assignee: Olympus Corporation, Tokyo (JP)

( * ) Notice: Subject to any disclaimer, the term of this patent is extended or adjusted under 35 U.S.C. 154(b) by 38 days.

(21) Appl. No.: 11/494,184

(22) Filed: Jul. 27, 2006

(65) Prior Publication Data

US 2006/0261263 A1 Nov. 23, 2006

Related U.S. Application Data

(62) Division of application No. 10/846,967, filed on May 14, 2004, now Pat. No. 7,129,473.

(30) Foreign Application Priority Data

May 16, 2003 (JP) .............................. 2003-139522
May 30, 2003 (JP) .............................. 2003-155816
Jun. 3, 2003 (JP) .............................. 2003-158463

(51) Int. Cl.
*H01J 3/14* (2006.01)
*G01B 11/30* (2006.01)
(52) U.S. Cl. .................... 250/234; 250/230; 250/205; 250/559.22; 356/237.2; 356/600; 356/601; 359/197

(58) Field of Classification Search ................ 250/205, 250/230, 234, 235, 559.22; 356/237.2, 237.4, 356/237.5, 600, 602; 359/146, 147
See application file for complete search history.

(56) References Cited

U.S. PATENT DOCUMENTS

| 4,127,781 | A | 11/1978 | Sato |
| 4,152,588 | A | 5/1979 | Klatt et al. |
| 4,348,939 | A | 9/1982 | Hipp |
| 4,423,496 | A | 12/1983 | Opheij et al. |
| 4,564,757 | A | 1/1986 | LaBudde et al. |

(Continued)

FOREIGN PATENT DOCUMENTS

| JP | 7-86557 | 3/1995 |
| JP | 9-230248 | 9/1997 |

*Primary Examiner*—Stephen Yam
(74) *Attorney, Agent, or Firm*—Scully, Scott, Murphy & Presser, P.C.

(57) ABSTRACT

A control portion of an optical image pickup apparatus includes a scan driver, a lock-in amplifier, and an A/D converter. The scan driver outputs a predetermined drive signal to a Y-scanning mirror and an X-scanning mirror and scans the Y-scanning mirror and the X-scanning mirror. The lock-in amplifier detects a signal level Vout of a frequency component of the drive signal of the scan driver among signals detected by a detector portion. The A/D converter converts a signal detected by a detector portion and a signal level of the detected signal of a frequency component of a drive signal detected by the lock-in amplifier to digital signals and outputs the digital signals to an image processor. Thus, mirror scan operations of the scanning mirrors can be securely detected.

14 Claims, 68 Drawing Sheets

U.S. PATENT DOCUMENTS

| | | |
|---|---|---|
| 4,694,164 A | 9/1987 | Noguchi |
| 4,861,982 A | 8/1989 | Smid et al. |
| 5,131,744 A | 7/1992 | Kaneko et al. |
| 5,223,710 A | 6/1993 | Pavlak |
| 5,235,180 A * | 8/1993 | Montagu ............... 250/231.13 |
| 5,247,173 A | 9/1993 | Benchetrit et al. |
| 5,305,759 A * | 4/1994 | Kaneko et al. ............. 600/476 |
| 6,321,106 B1 * | 11/2001 | Lemelson .................. 600/407 |
| 6,441,356 B1 * | 8/2002 | Mandella et al. ......... 250/201.3 |
| 6,615,072 B1 * | 9/2003 | Izatt et al. .................... 600/478 |
| 6,895,270 B2 * | 5/2005 | Ostrovsky .................. 600/476 |
| 7,280,600 B2 * | 10/2007 | Orhand et al. ......... 375/240.24 |

* cited by examiner

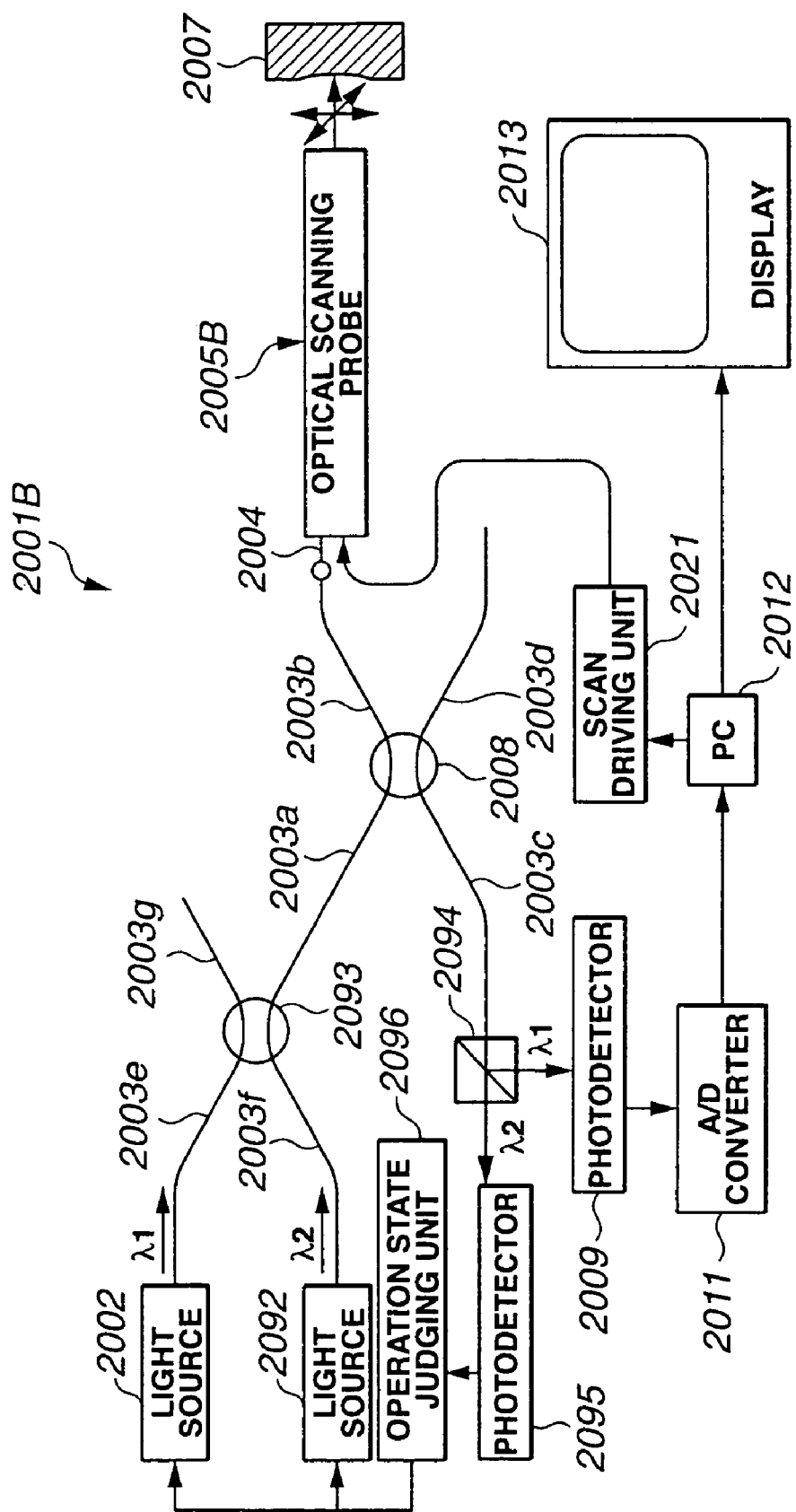

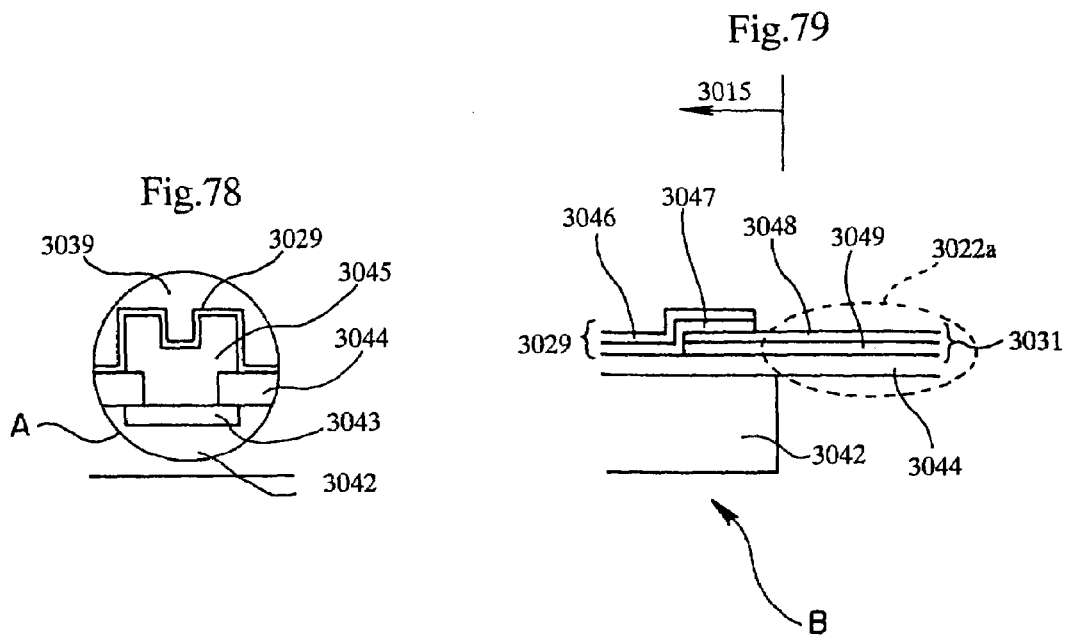
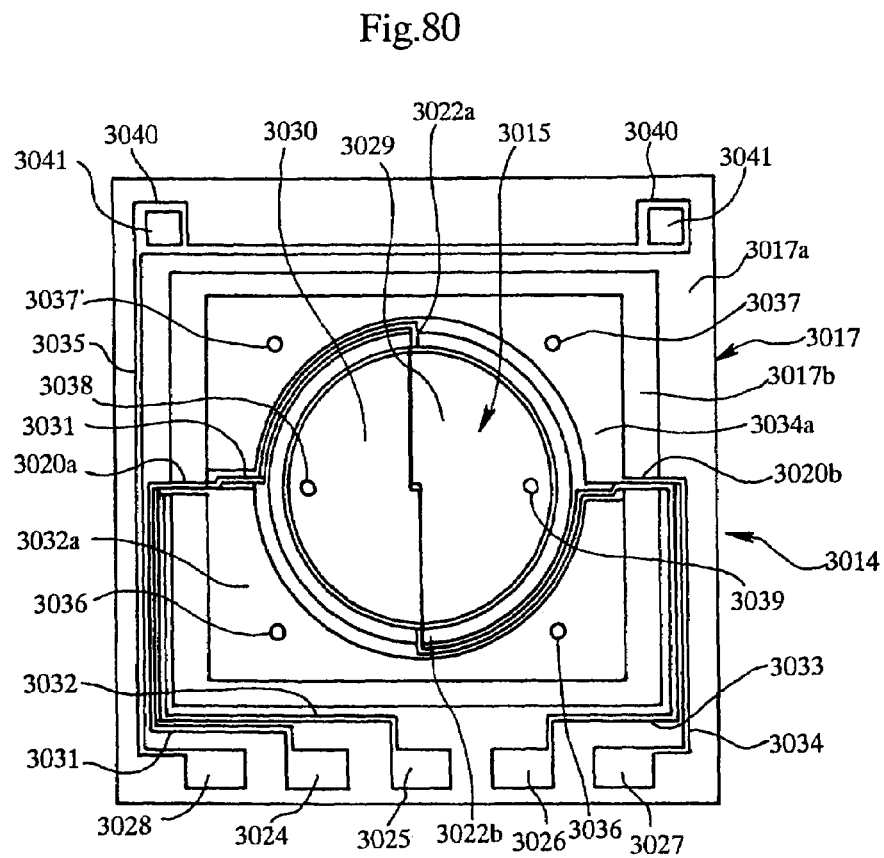

though a small confocal microscope is large, and a sample is cut into small sections and is placed on the microscope for observation.

OPTICAL IMAGE PICKUP APPARATUS FOR IMAGING LIVING BODY TISSUE

This application is a divisional of U.S. patent application Ser. No. 10/846,967 filed on May 14, 2004 now U.S. Pat. No. 7,129,473 which claims benefit of Japanese Application No. 2003-158463 filed in Japan on Jun. 3, 2003, Japanese application No. 2003-155816 filed in Japan on May 30, 2003, Japanese Application No. 2003-139522 filed in Japan on May 16, 2003, and Japanese Application No. 2002-308678 filed in Japan on Oct. 23, 2002, the entirety of each of the above-identified applications are incorporated herein by reference.

BACKGROUND OF THE INVENTION

1. Field of the Invention

The present invention relates to an optical image pickup apparatus for imaging a living body tissue by using a confocal optical system.

2. Related Art Statement

Recently, an optical scan type confocal microscope has been known as means for observing living body tissues and/or cells with higher resolution in an optical axis direction. However, in this case, the size of a general confocal microscope is large, and a sample is cut into small sections and is placed on the microscope for observation.

A technology for guiding a small confocal microscope to and observing a biological digestive tract, for example, has been disclosed as a minute confocal microscope in Japanese Unexamined Patent Application Publication No. 9-230248, for example.

OBJECTS AND SUMMARY OF THE INVENTION

An optical image pickup apparatus according to the invention includes:

at least one light source;

first light transmitting means for transmitting light generated from the light source and irradiating a subject;

light gathering means for gathering light transmitted by the first light transmitting means to the subject;

optical scanning means for moving light to be irradiated to the subject;

photoreceptor means for receiving light from the subject;

first photodetector means for detecting light received by using the photoreceptor means;

image creating means for creating an image from signals output from the photodetector means;

second photodetector means for detecting reflected light, scattering light or fluorescence generated in the first light transmitting means, the light-gathering means, the optical scanning means or the subject; and scanning state detecting means for detecting an operation state of the optical scanning means based on signals output from the second photodetector means.

The other features and advantages of the invention will be apparent from following descriptions.

BRIEF OF DESCRIPTION OF THE DRAWINGS

FIGS. 1 and 2 relate to a first embodiment of the invention. FIG. 1 is a configuration diagram showing a configuration of an optical image pickup apparatus. FIG. 2 is a diagram showing a construction of an internal part of a distal end of an optical scan probe in FIG. 1.

Figure 8:
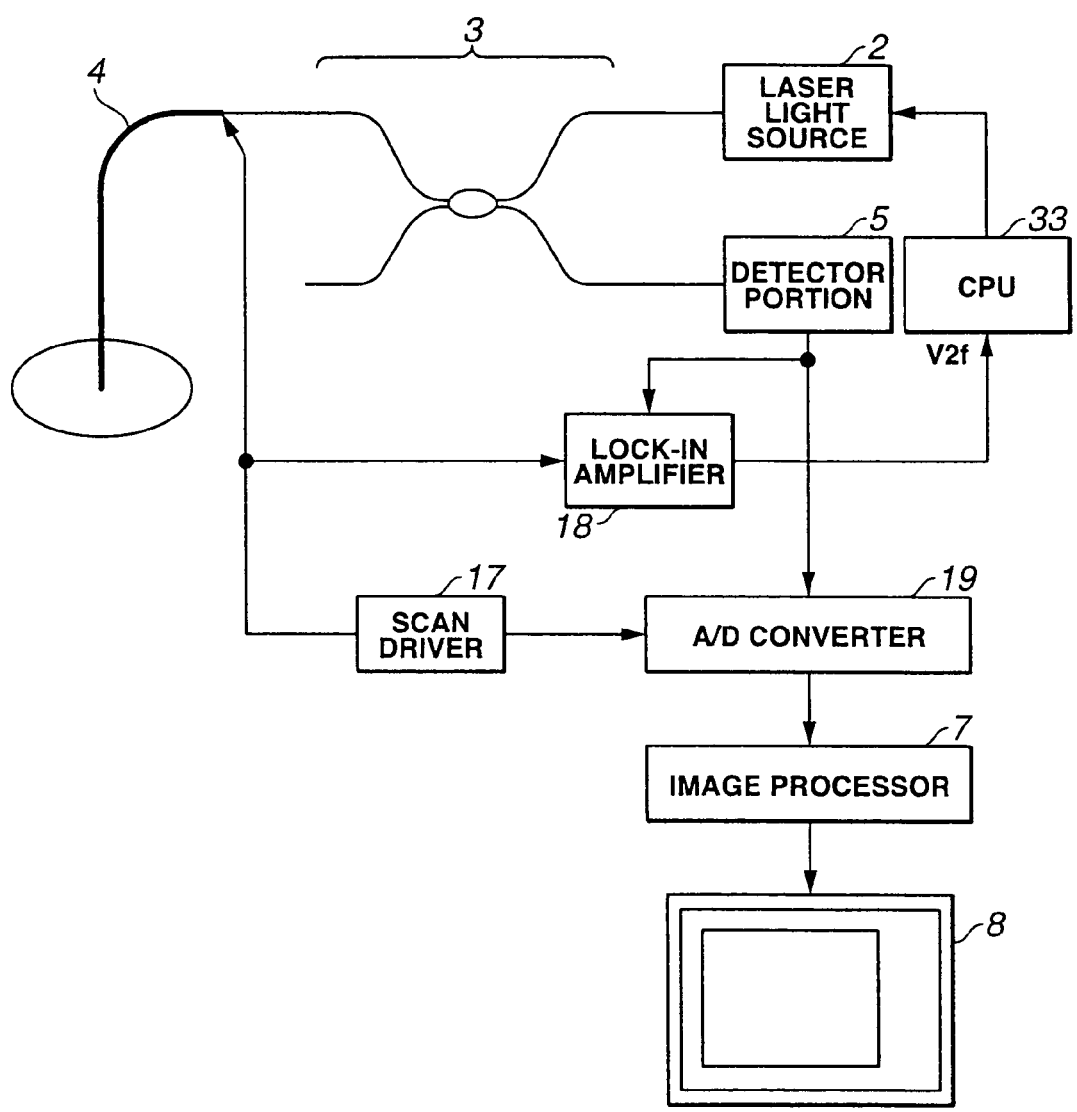
Figure 9:
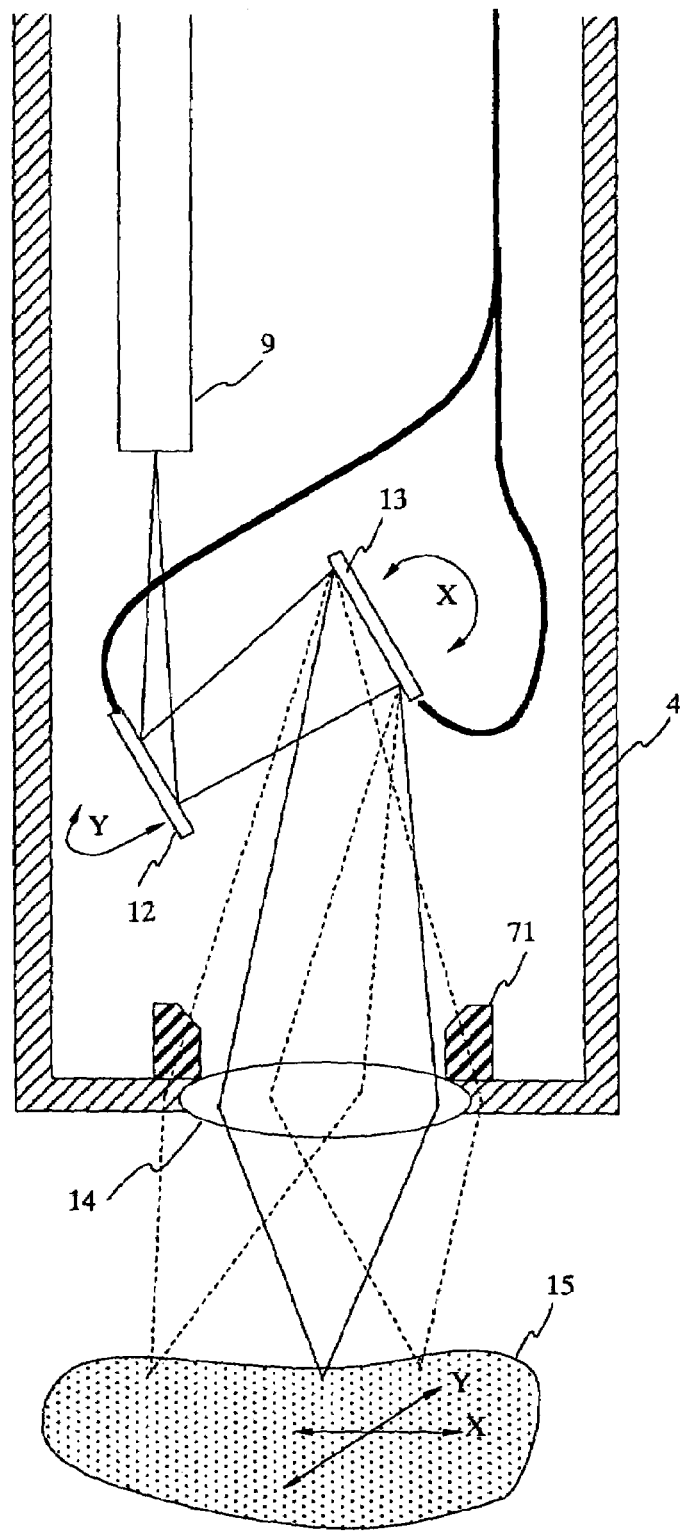
Figure 10:
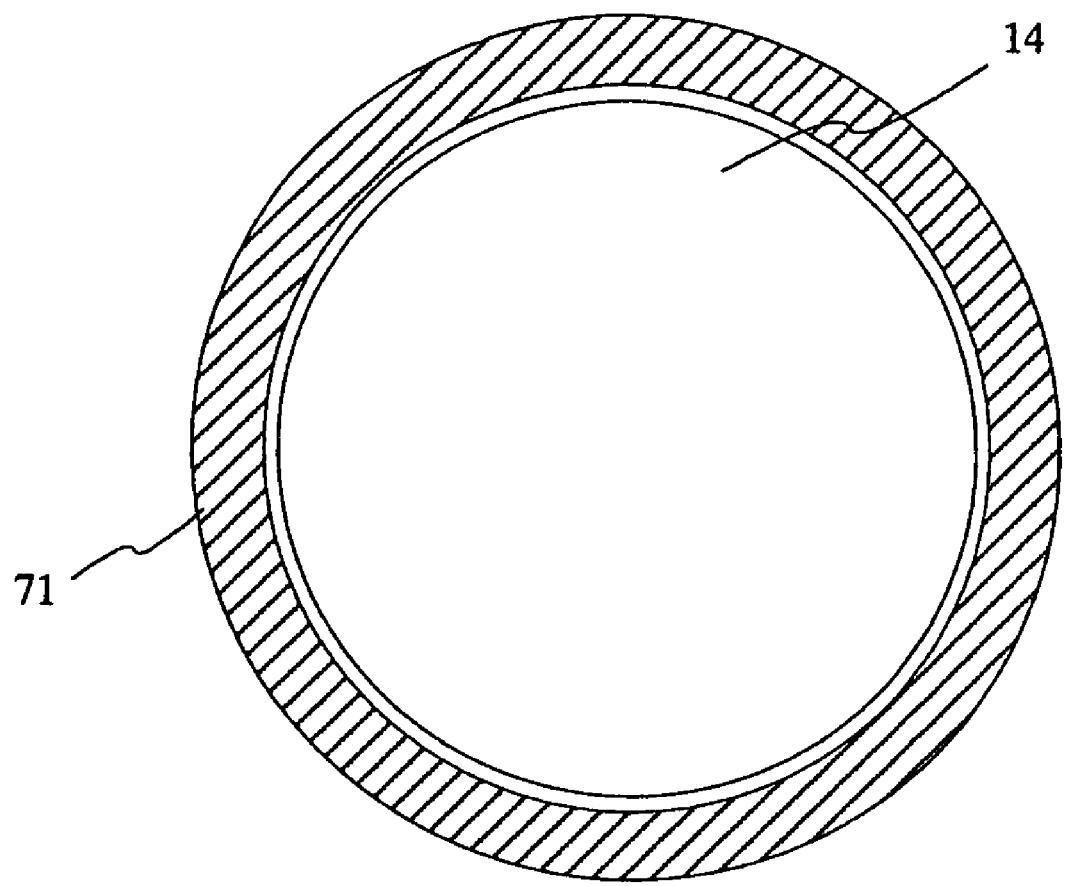
Figure 11:
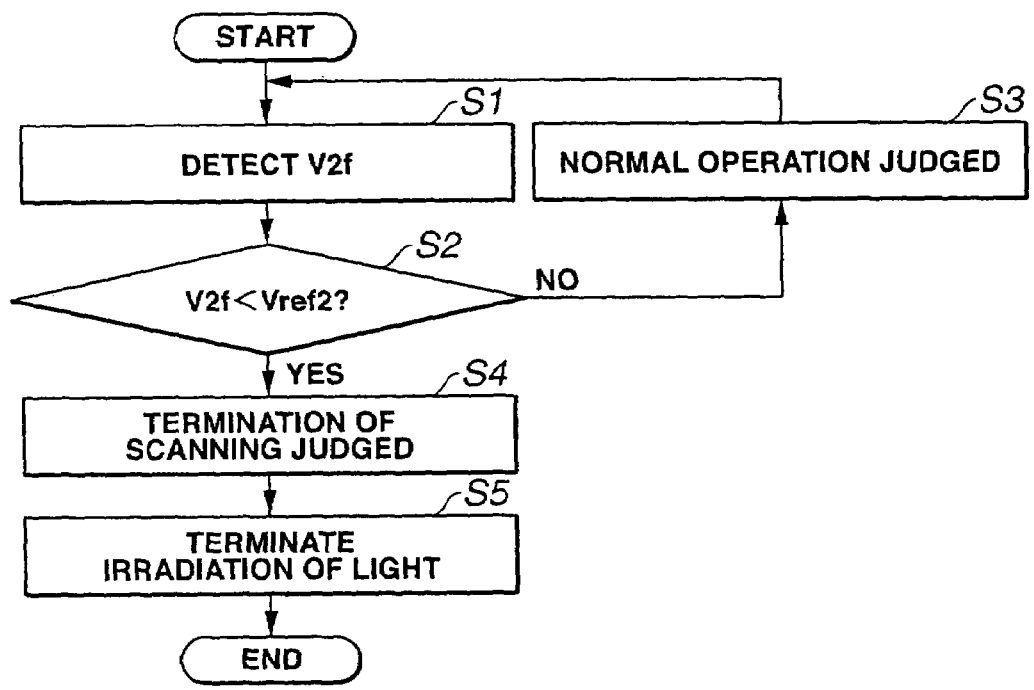
Figure 12:
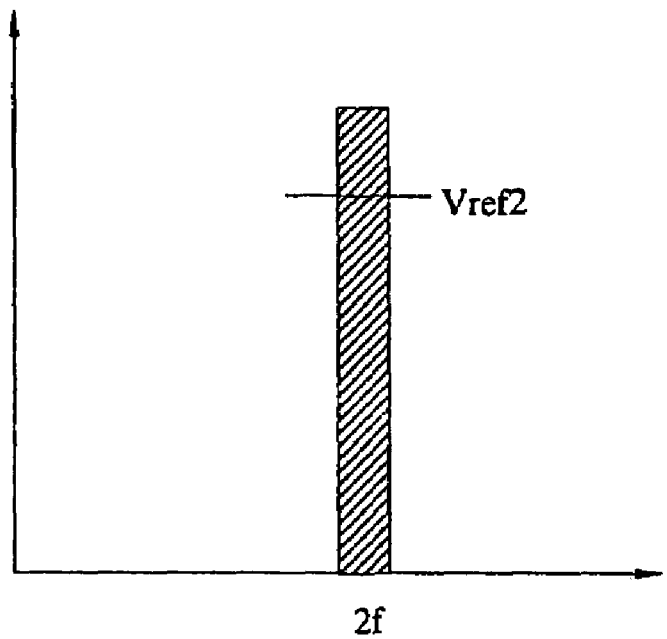
Figure 13:
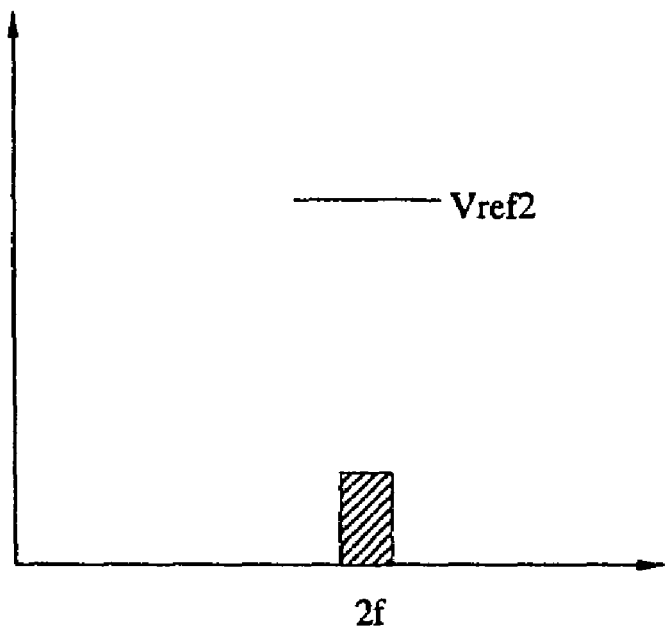
Figure 14:
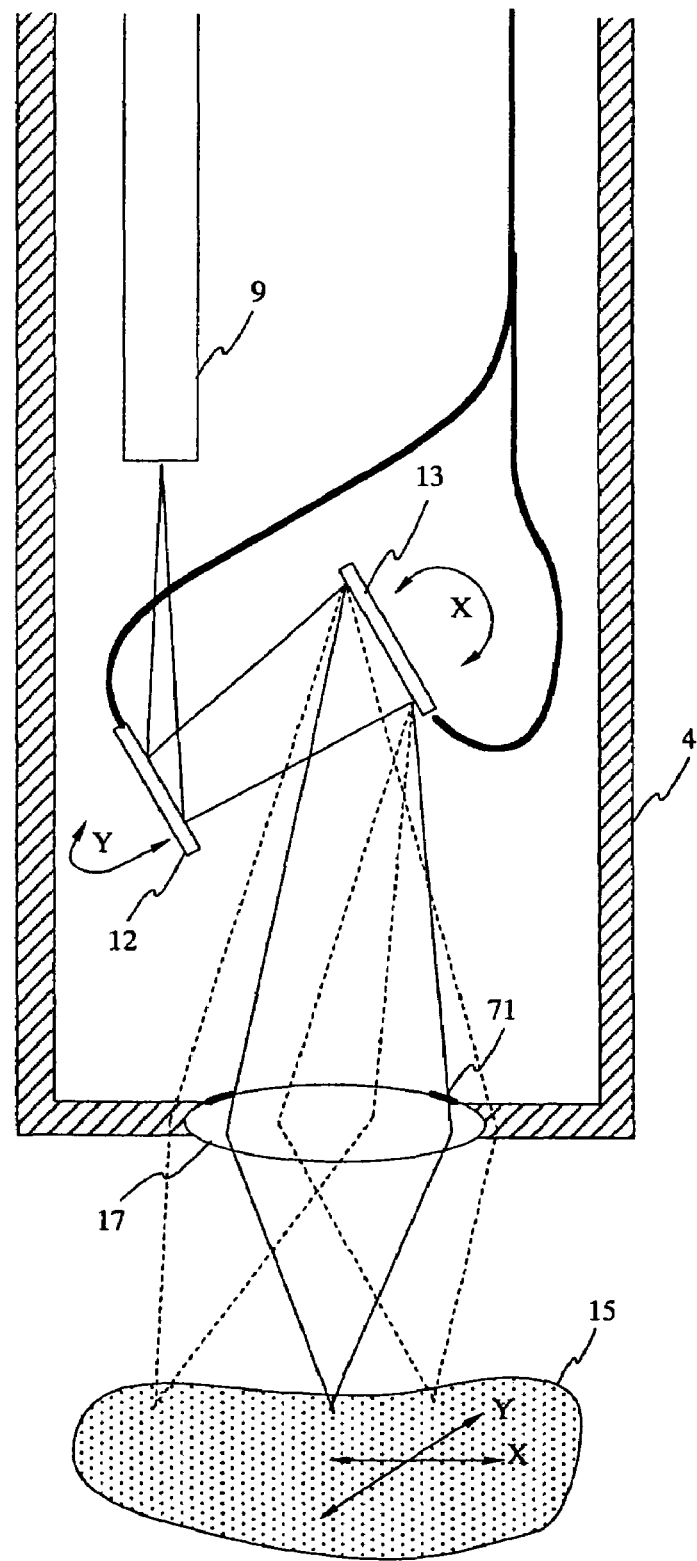
Figure 15:
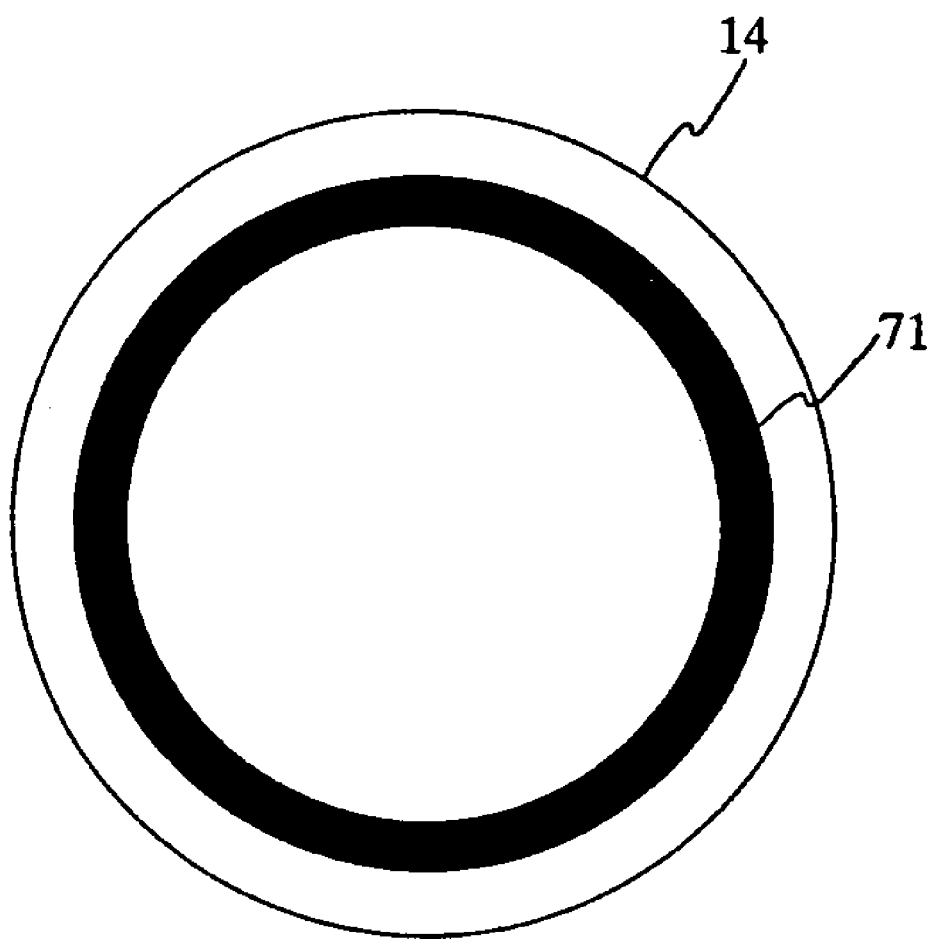

FIGS. 8 to 15 relate to a seventh embodiment of the invention. FIG. 8 is a configuration diagram showing a configuration of an optical image pickup apparatus. FIG. 9 is a diagram showing a construction of an internal part of a distal end of an optical scan probe in FIG. 8. FIG. 10 is a diagram showing a configuration of an objective lens in FIG. 9. FIG. 11 is a flowchart illustrating an operation of a CPU in FIG. 8. FIG. 12 is a first diagram illustrating processing in FIG. 11. FIG. 13 is a second diagram illustrating processing in FIG. 11. FIG. 14 is a diagram showing a variation example of the optical scan probe in FIG. 8. FIG. 15 is a diagram showing a configuration of an objective lens in FIG. 14.

Figure 16:
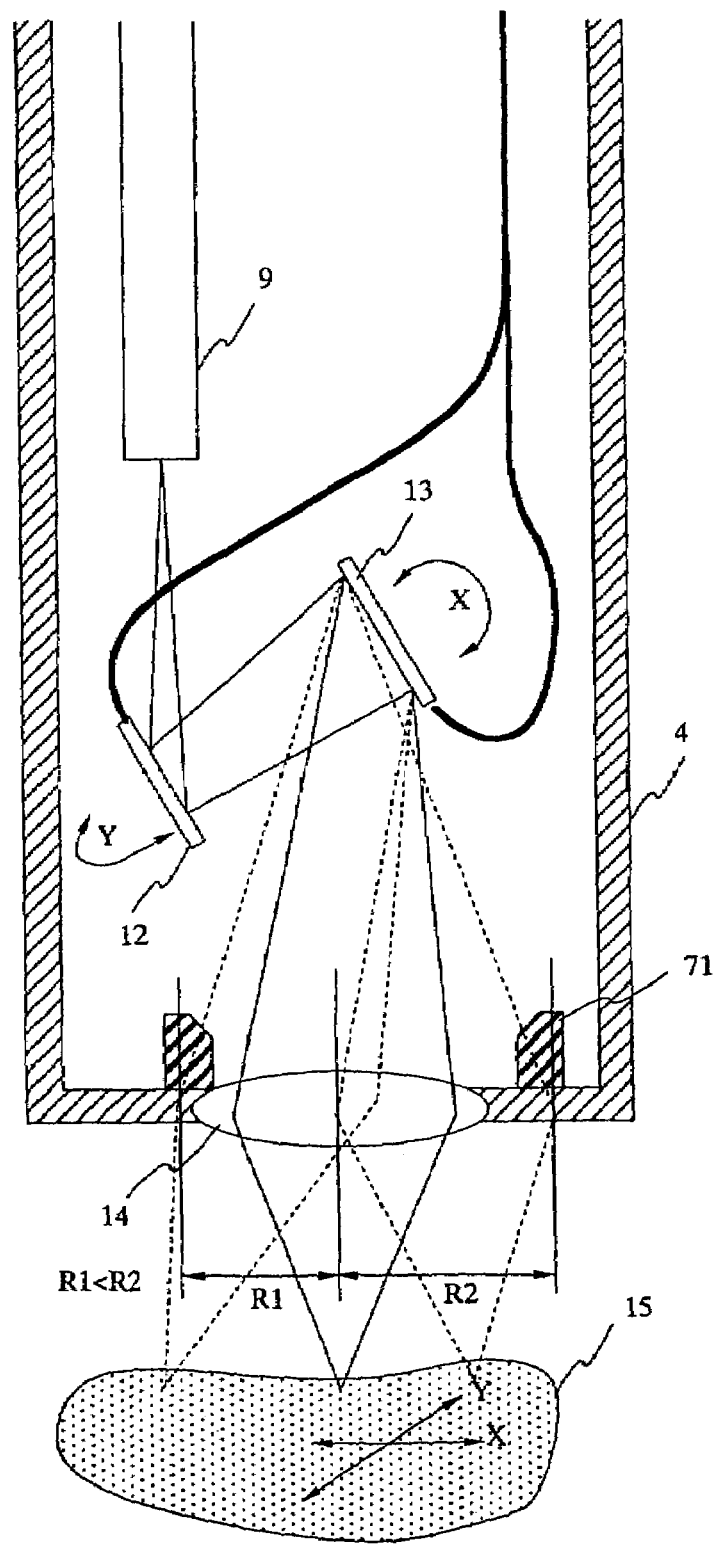
Figure 17:
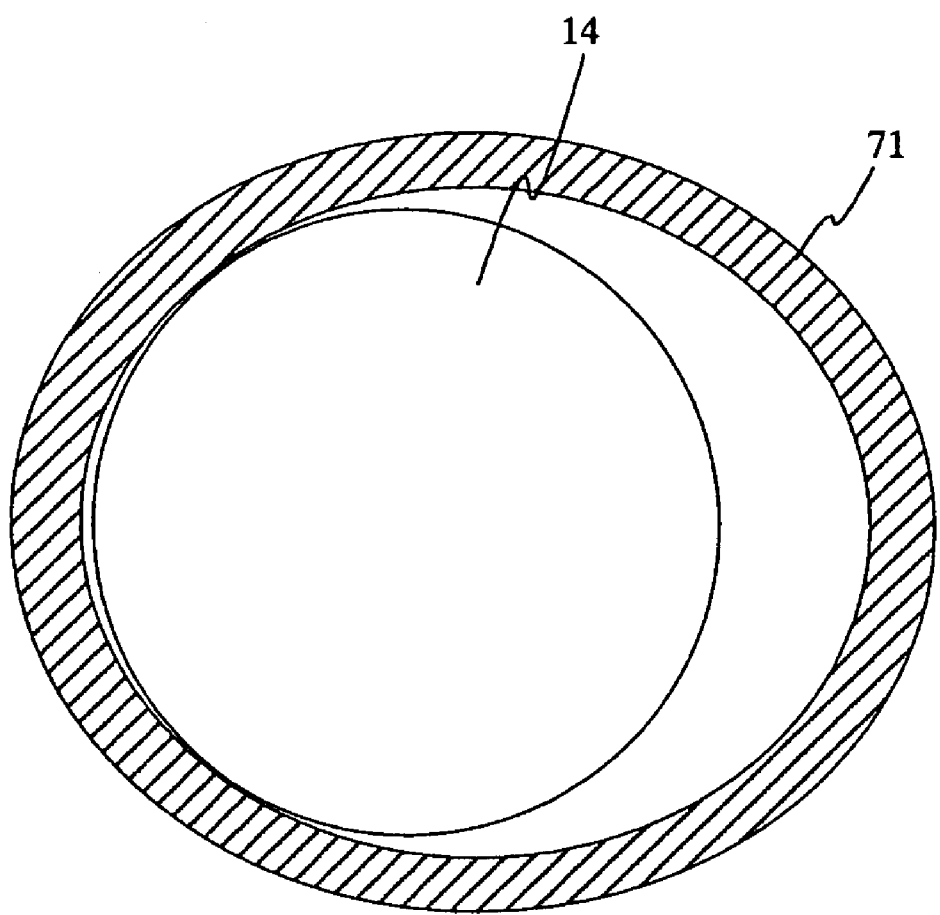
Figure 18:
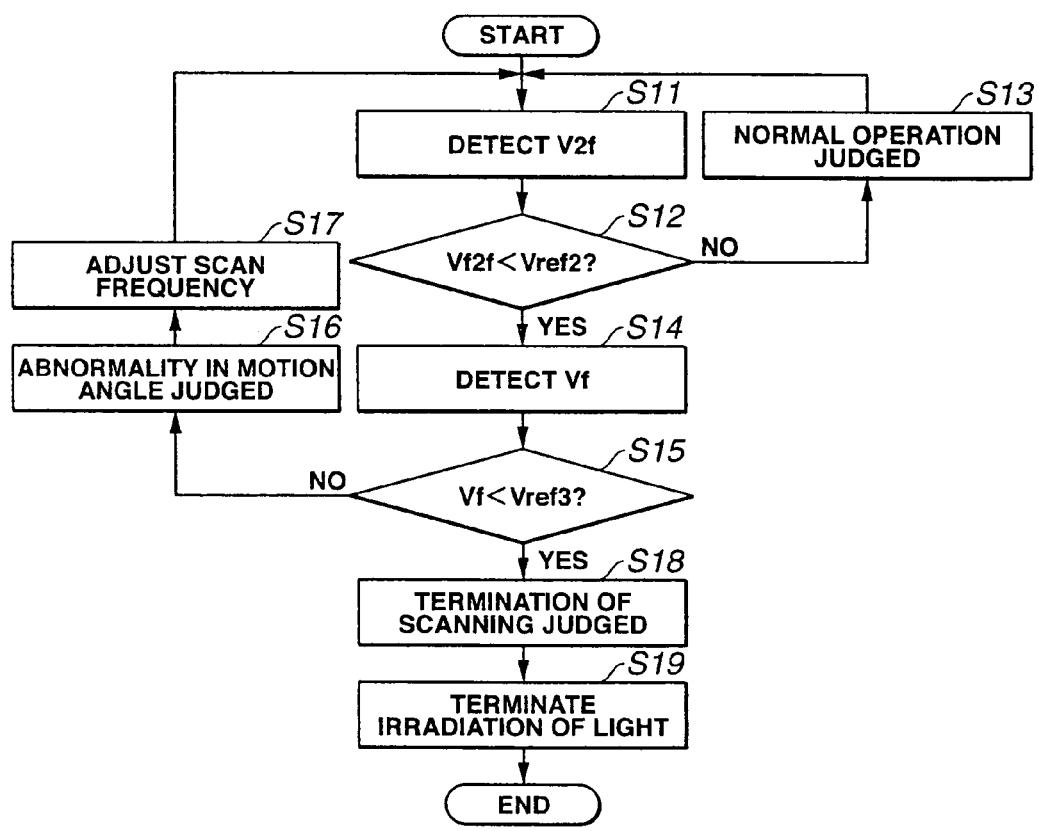
Figure 19:
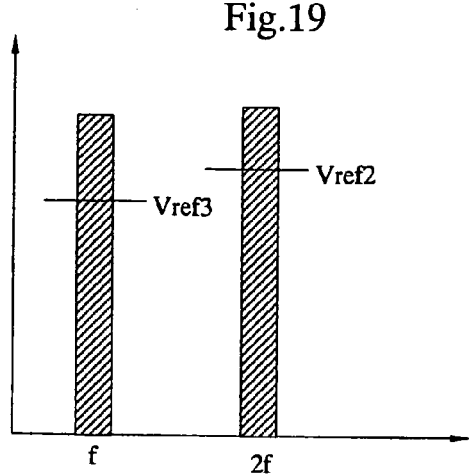
Figure 20:
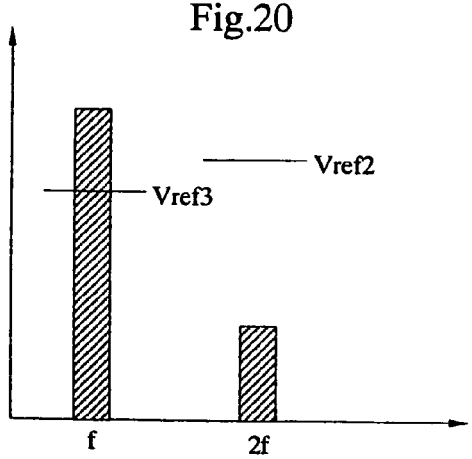
Figure 21:
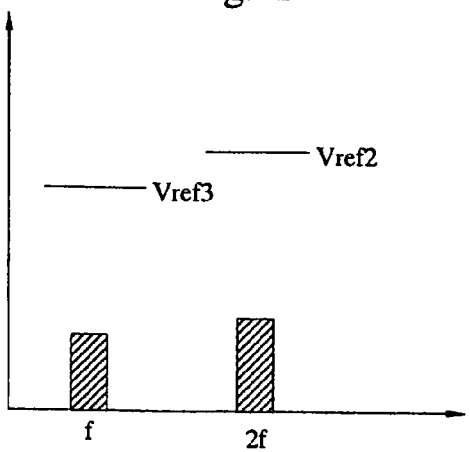

FIGS. 16 to 21 relate to an eighth embodiment of the invention. FIG. 16 is a diagram showing a construction of an internal part of a distal end of an optical scan probe. FIG. 17 is a diagram showing a construction of an objective lens in FIG. 16. FIG. 18 is a flowchart illustrating operations of a CPU when the optical scan probe in FIG. 17 is used. FIG. 19 is a first diagram illustrating processing in FIG. 18. FIG. 20 is a second diagram illustrating processing in FIG. 18. FIG. 21 a third diagram illustrating processing in FIG. 18.

Figure 22:
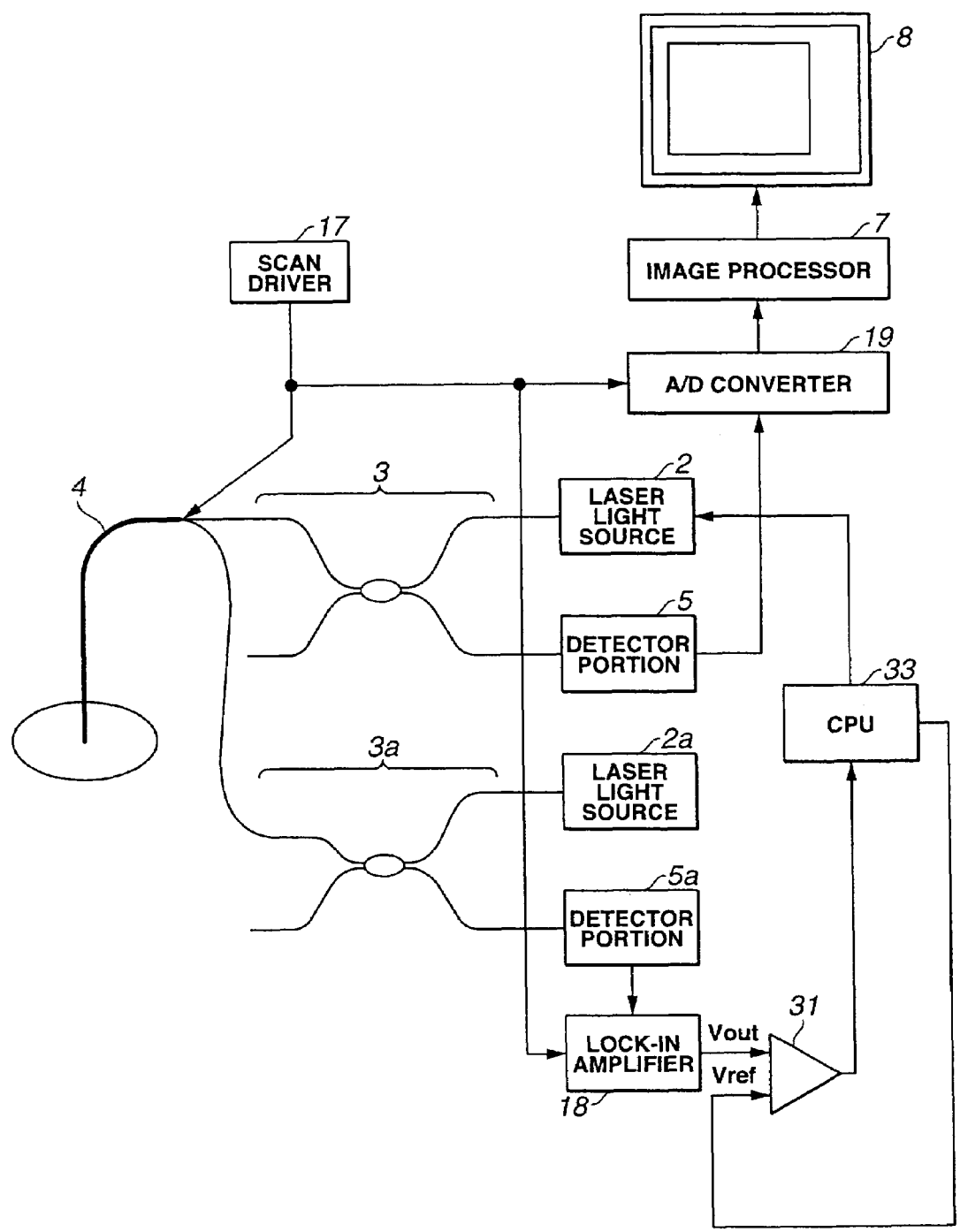
Figure 23:
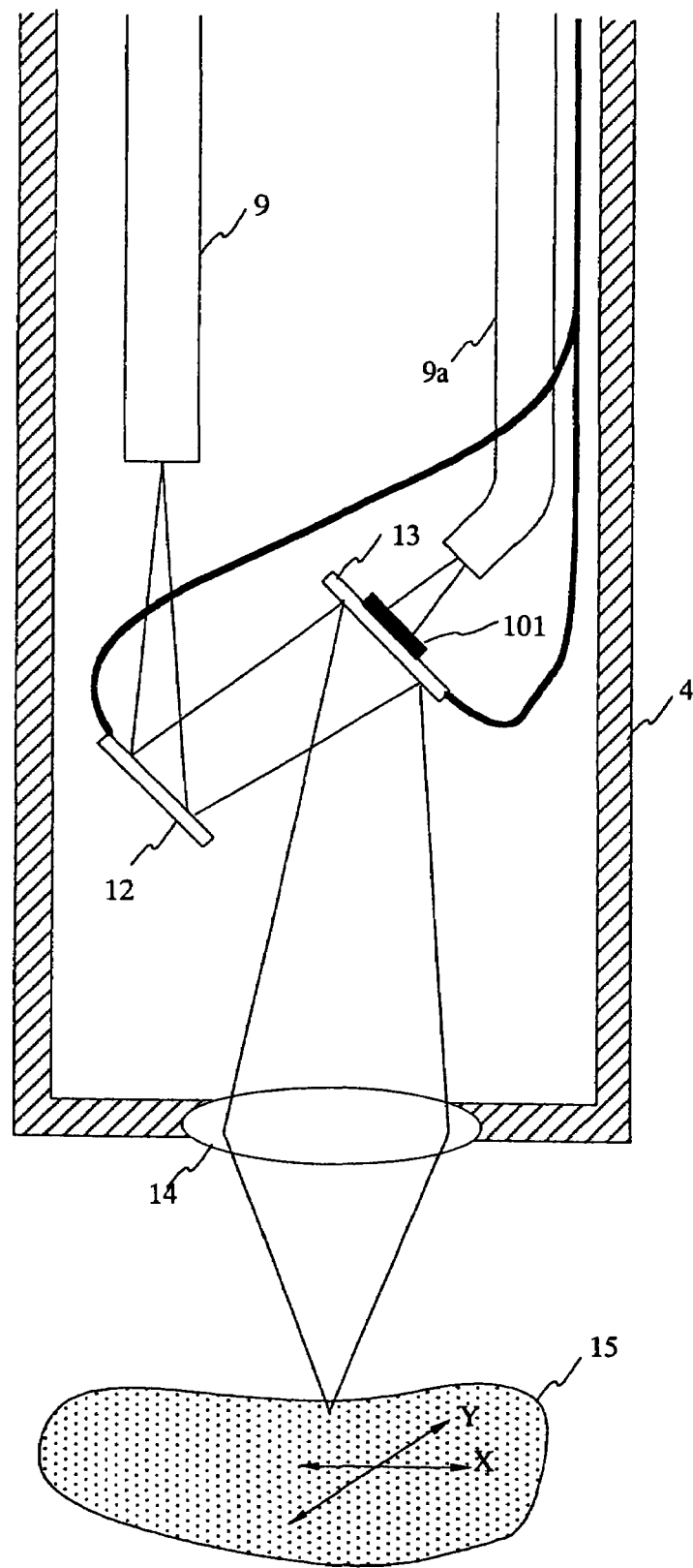
Figure 24:
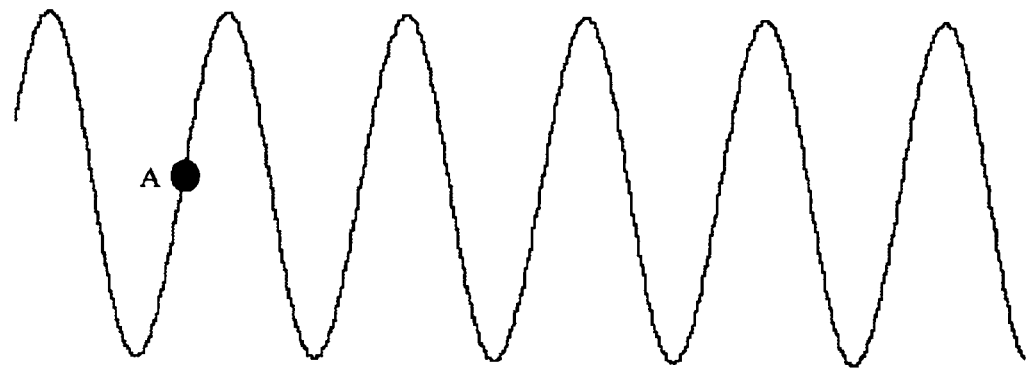
Figure 25:
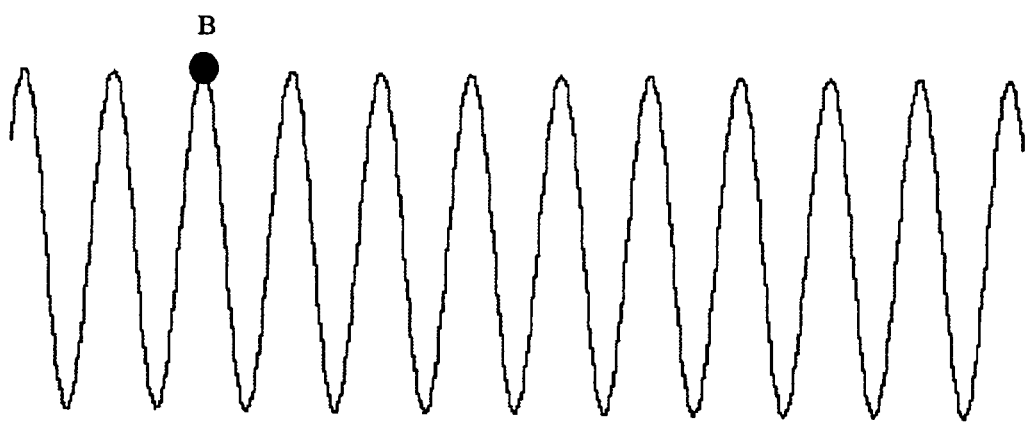
Figure 26:
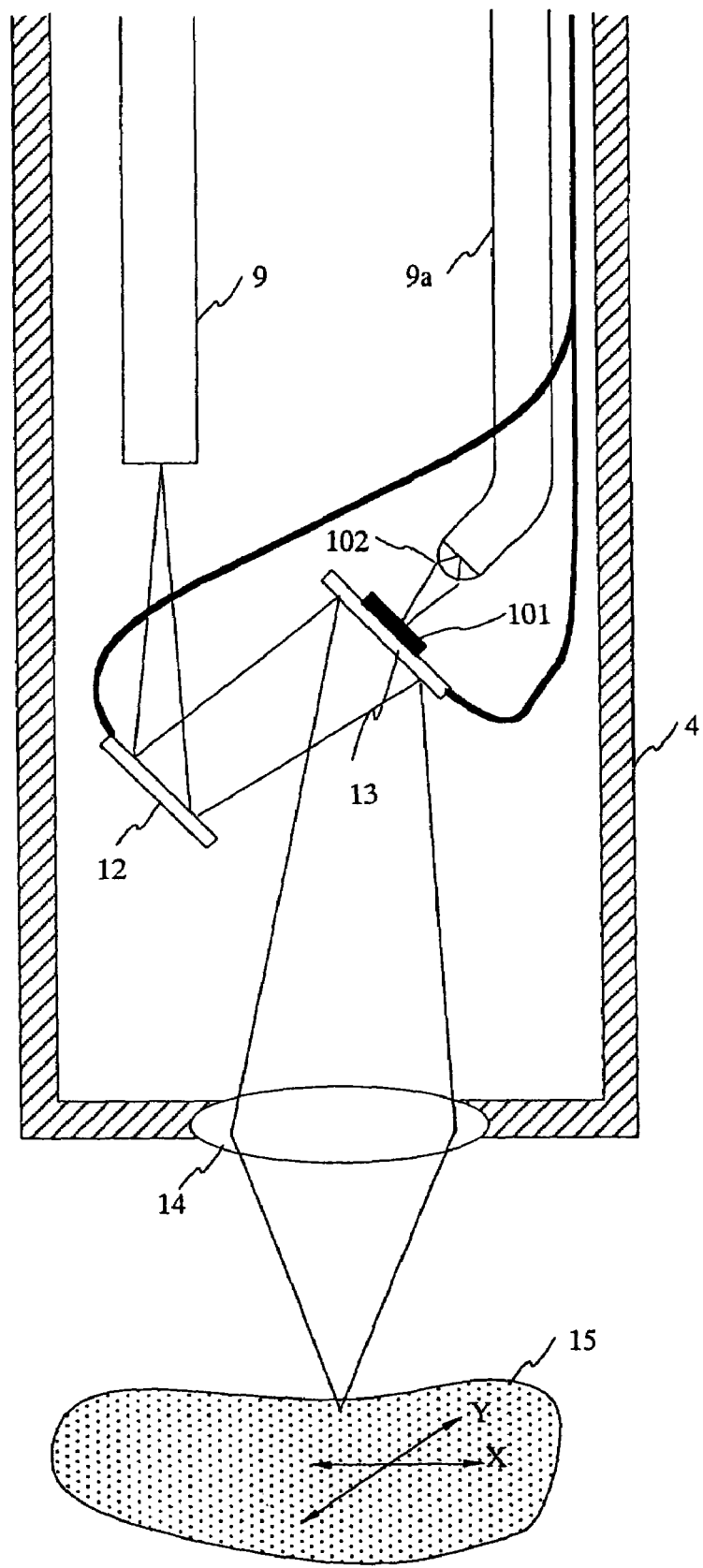

FIGS. 22 to 26 relate to a ninth embodiment of the invention. FIG. 22 is a configuration diagram showing a configuration of an optical image pickup apparatus. FIG. 23 is a diagram showing a construction of an internal part of a distal end of an optical scan probe in FIG. 22. FIG. 24 is a diagram showing a drive waveform of an X-scan mirror in FIG. 23. FIG. 25 is a diagram showing a waveform of return light from a scattering body in FIG. 23. FIG. 26 is a diagram showing a construction of an internal part of a distal end of a variation example of an optical scan probe in FIG. 22.

Figure 27:
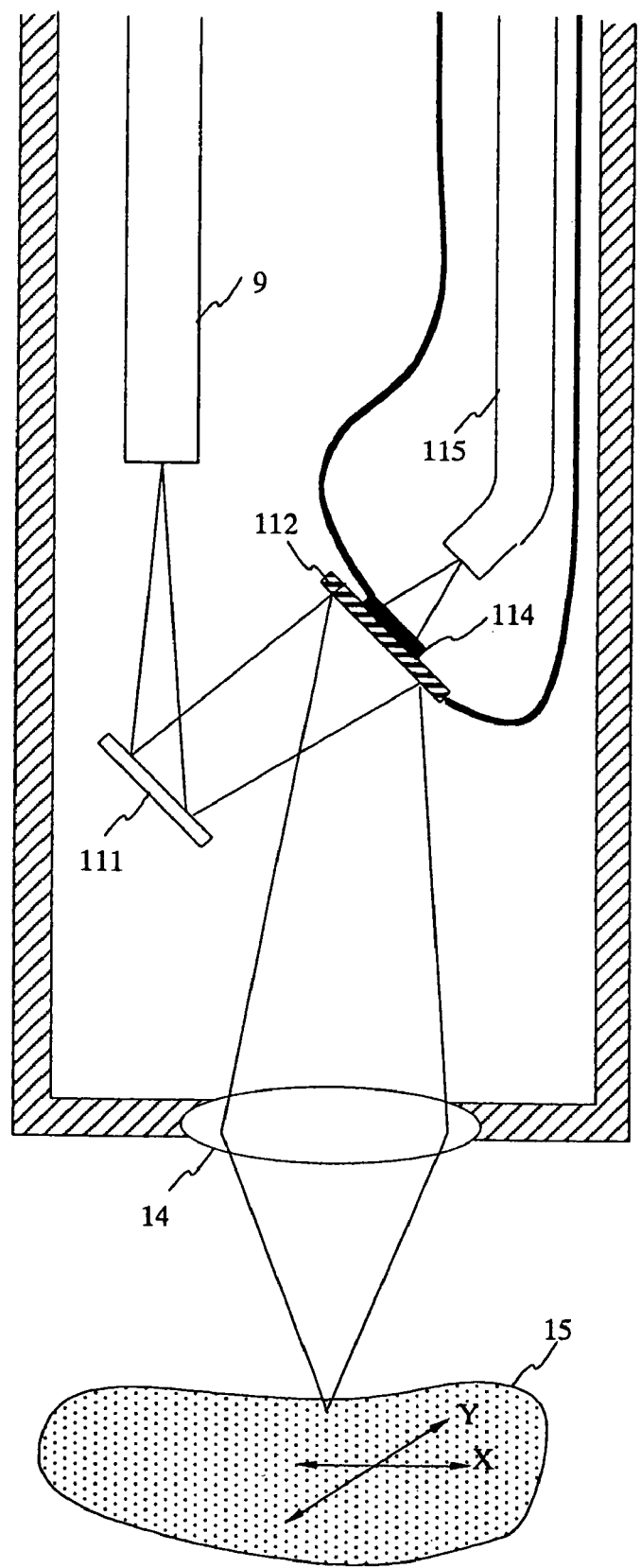
Figure 28:
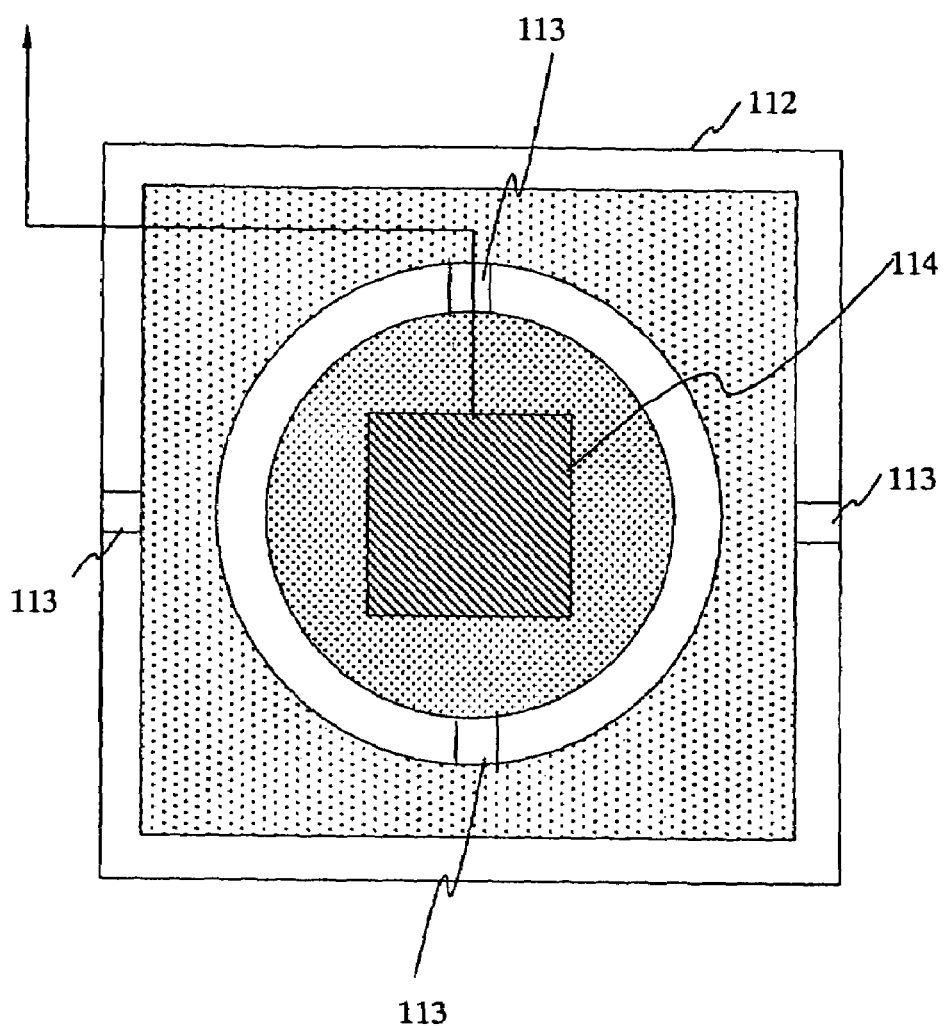
Figure 29:
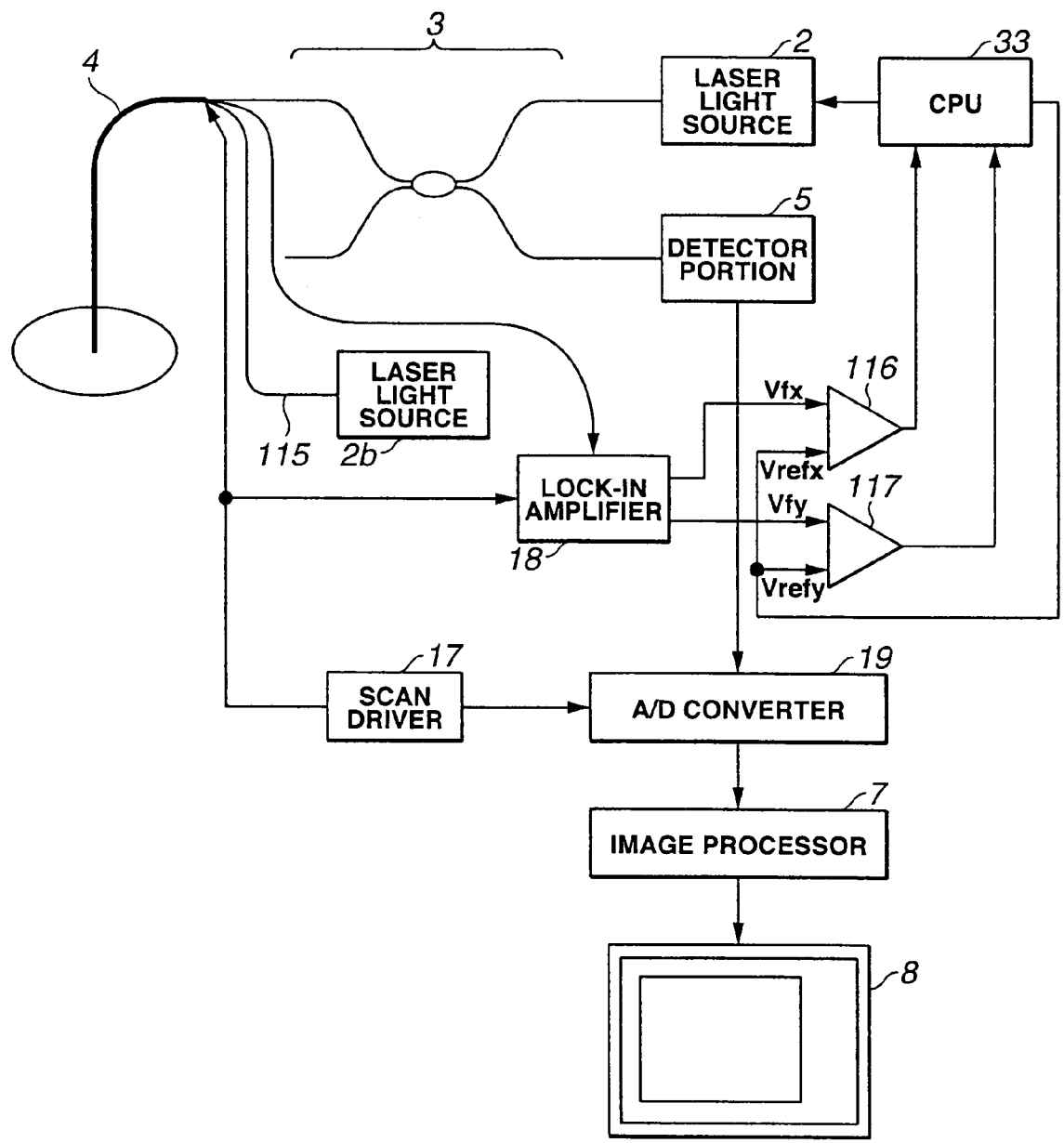
Figure 30:
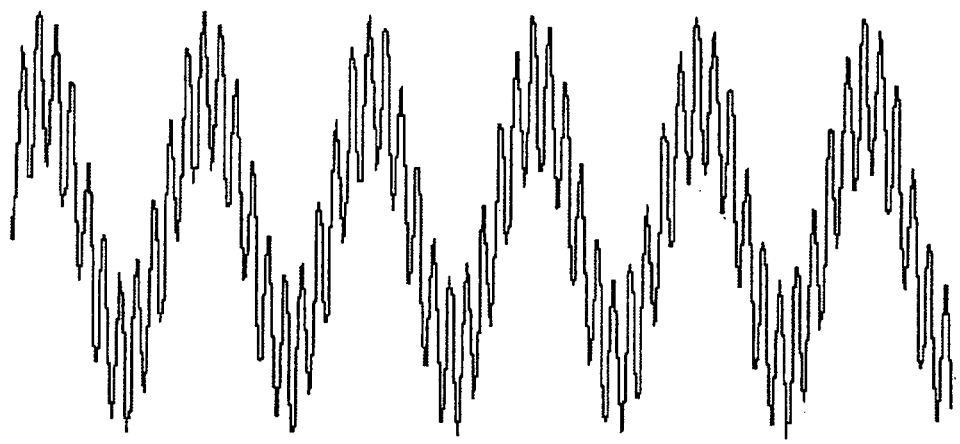
Figure 31:
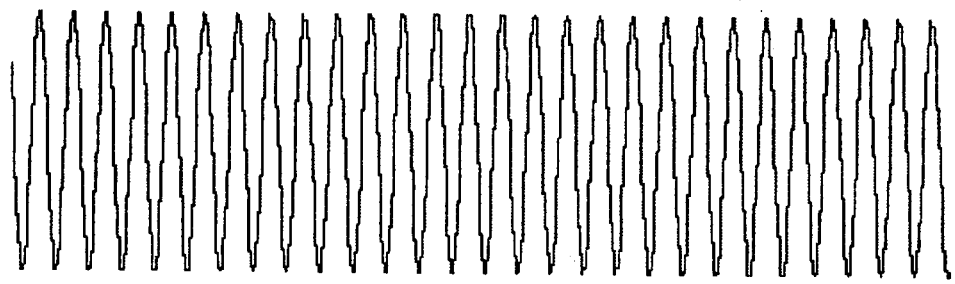
Figure 32:
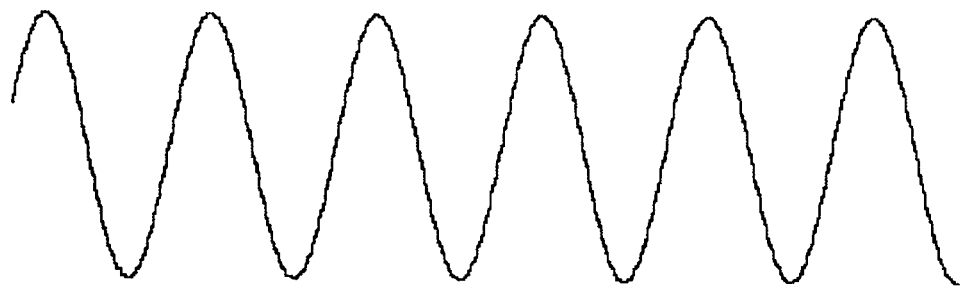
Figure 33:
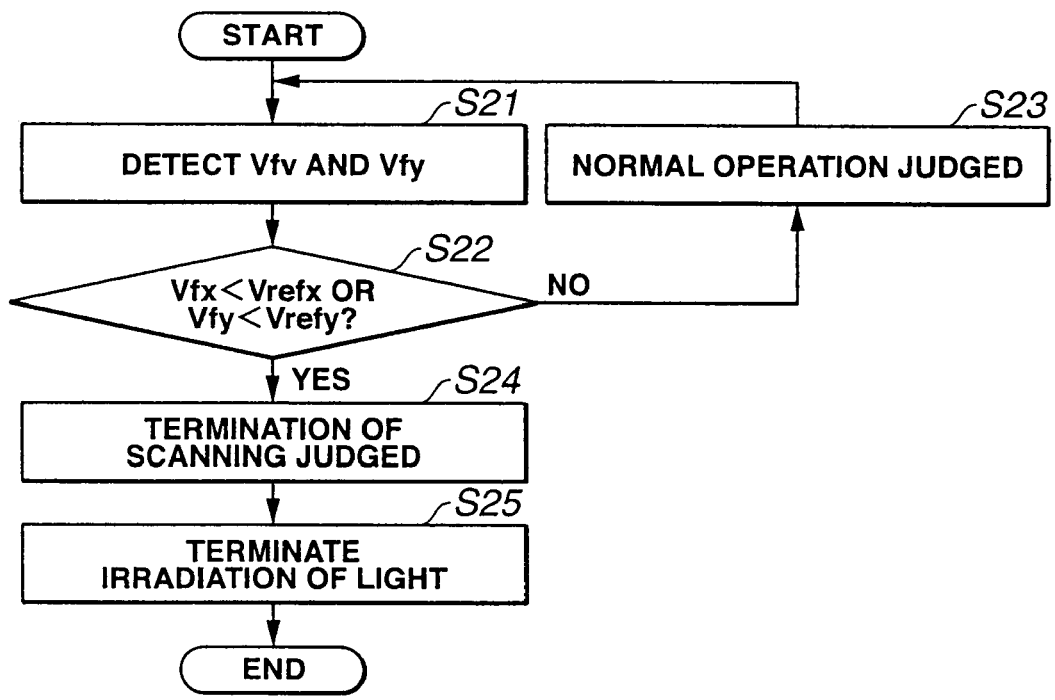

FIGS. 27 to 33 relate to a tenth embodiment of the invention. FIG. 27 is a diagram showing a construction of an internal part of a distal end of an optical scan probe. FIG. 28 is a diagram showing a construction of an XY-scan mirror in FIG. 27. FIG. 29 is a diagram showing a configuration of an optical image pickup apparatus for creating a confocal image by using the optical scan probe in FIG. 27. FIG. 30 is a diagram showing a waveform detected by a photodetector in FIG. 28. FIG. 31 is a diagram showing an X-component waveform of the signal waveform in FIG. 30. FIG. 32 is a diagram showing a Y-component waveform of the signal waveform in FIG. 30. FIG. 33 is a flowchart illustrating an operation of a CPU in FIG. 29.

Figure 34:
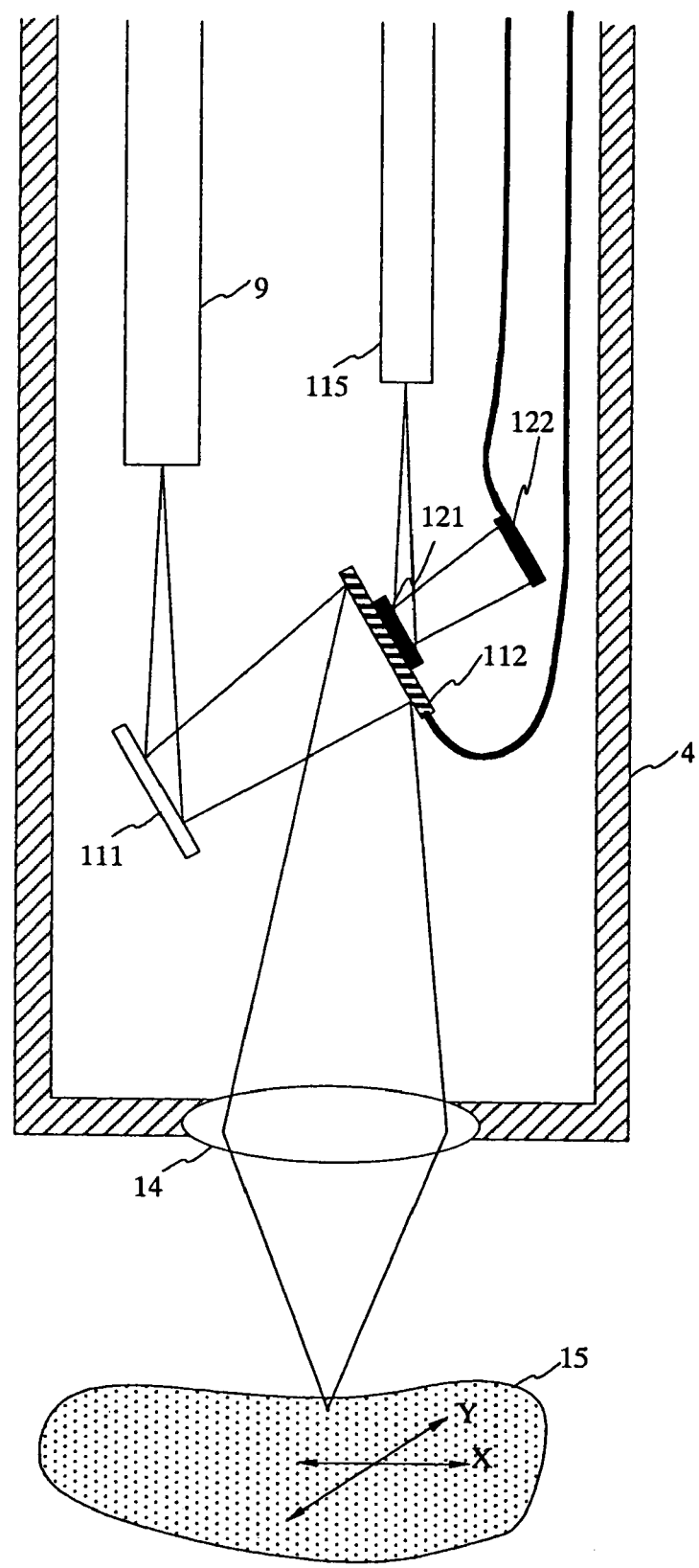
Figure 35:
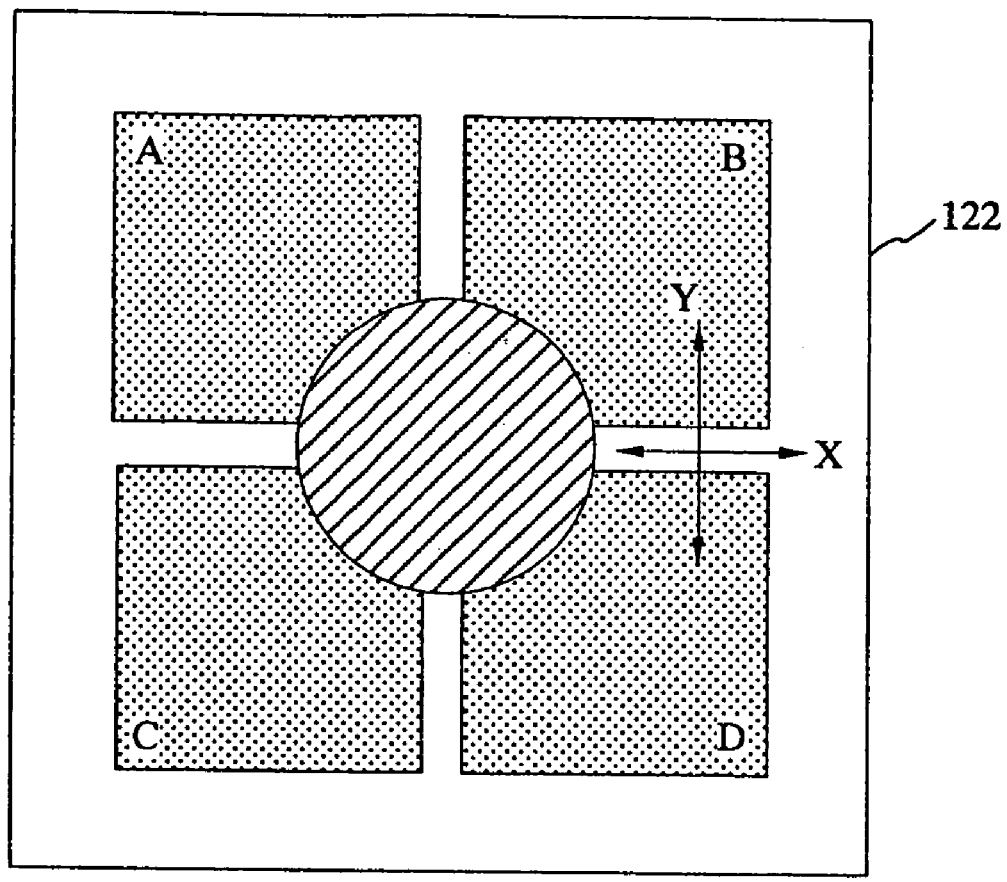
Figure 36:
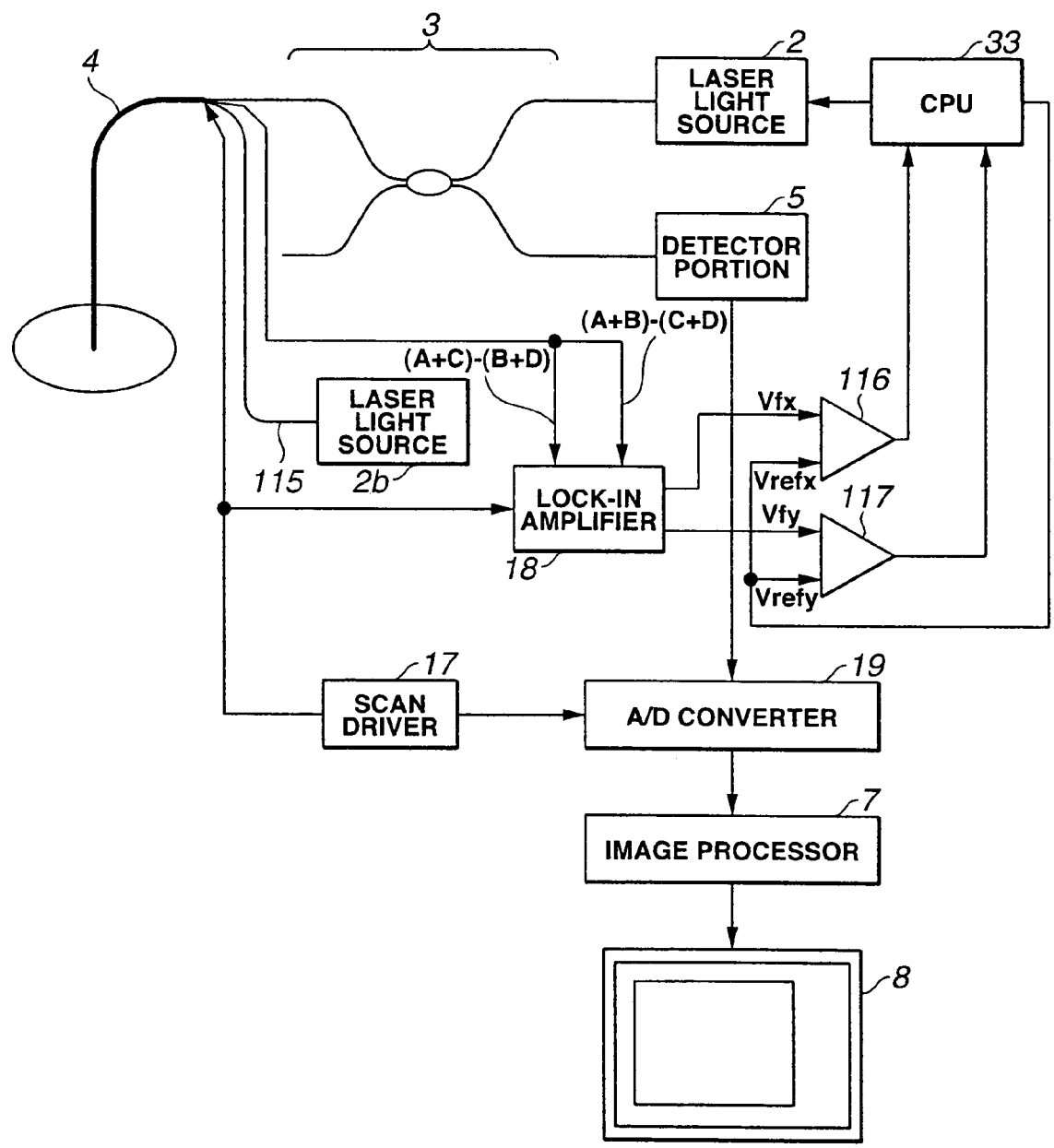
Figure 37:
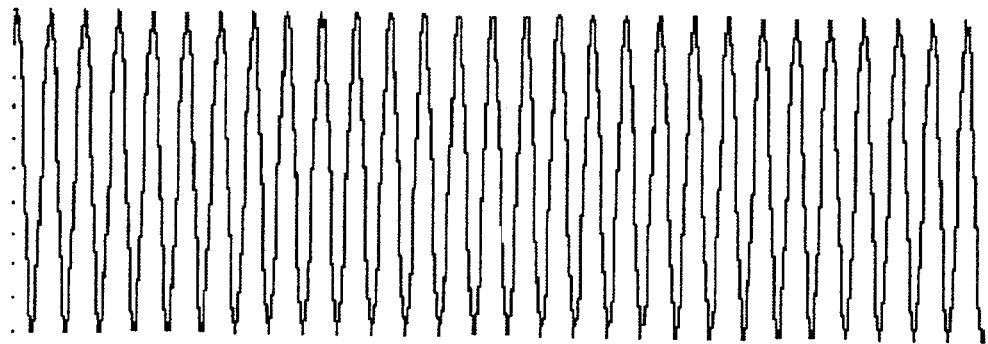
Figure 38:
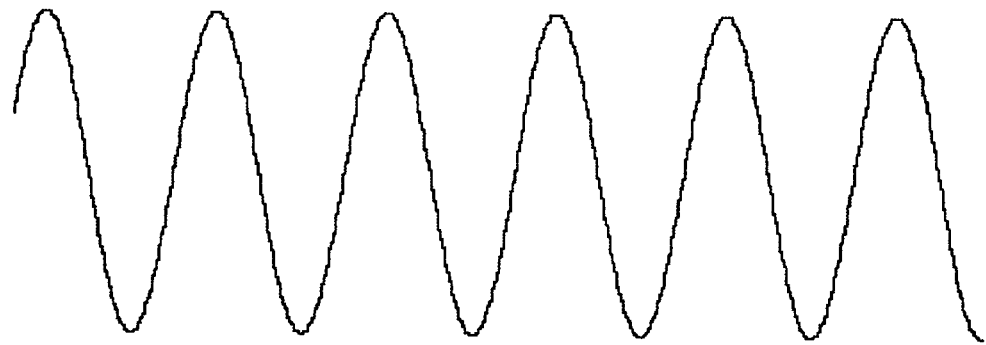
Figure 39:
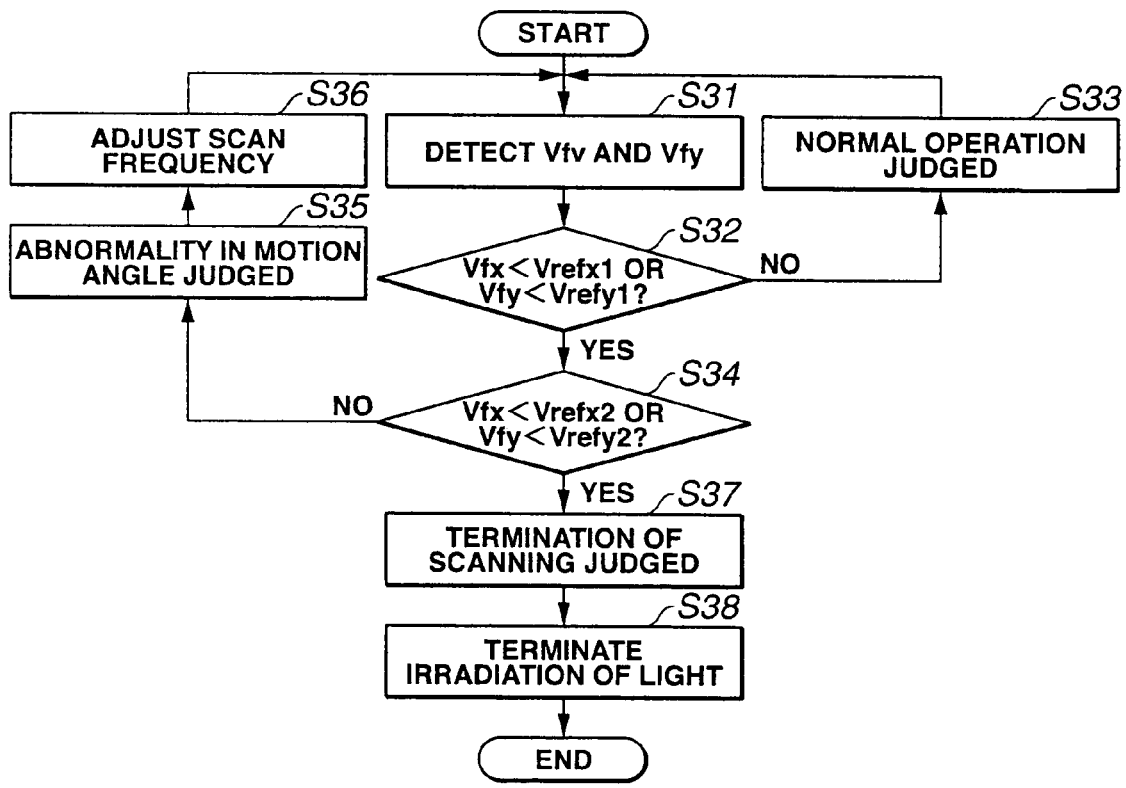

FIGS. 34 to 39 relate to an eleventh embodiment of the invention. FIG. 34 is a diagram showing a construction of an internal part of a distal end of an optical scan probe. FIG. 35 is a diagram showing a construction of four-part split photo-detector in FIG. 34. FIG. 36 is a diagram showing a configuration of an optical image pickup apparatus for creating a confocal image by using an optical scan probe in FIG. 34. FIG. 37 is a diagram showing X-component signals detected by the four-part split photodetector in FIG. 35. FIG. 38 is a diagram showing Y-component signals detected by the four-part split photodetector in FIG. 35. FIG. 39 is a flowchart illustrating operations of a CPU in FIG. 36.

Figure 40:
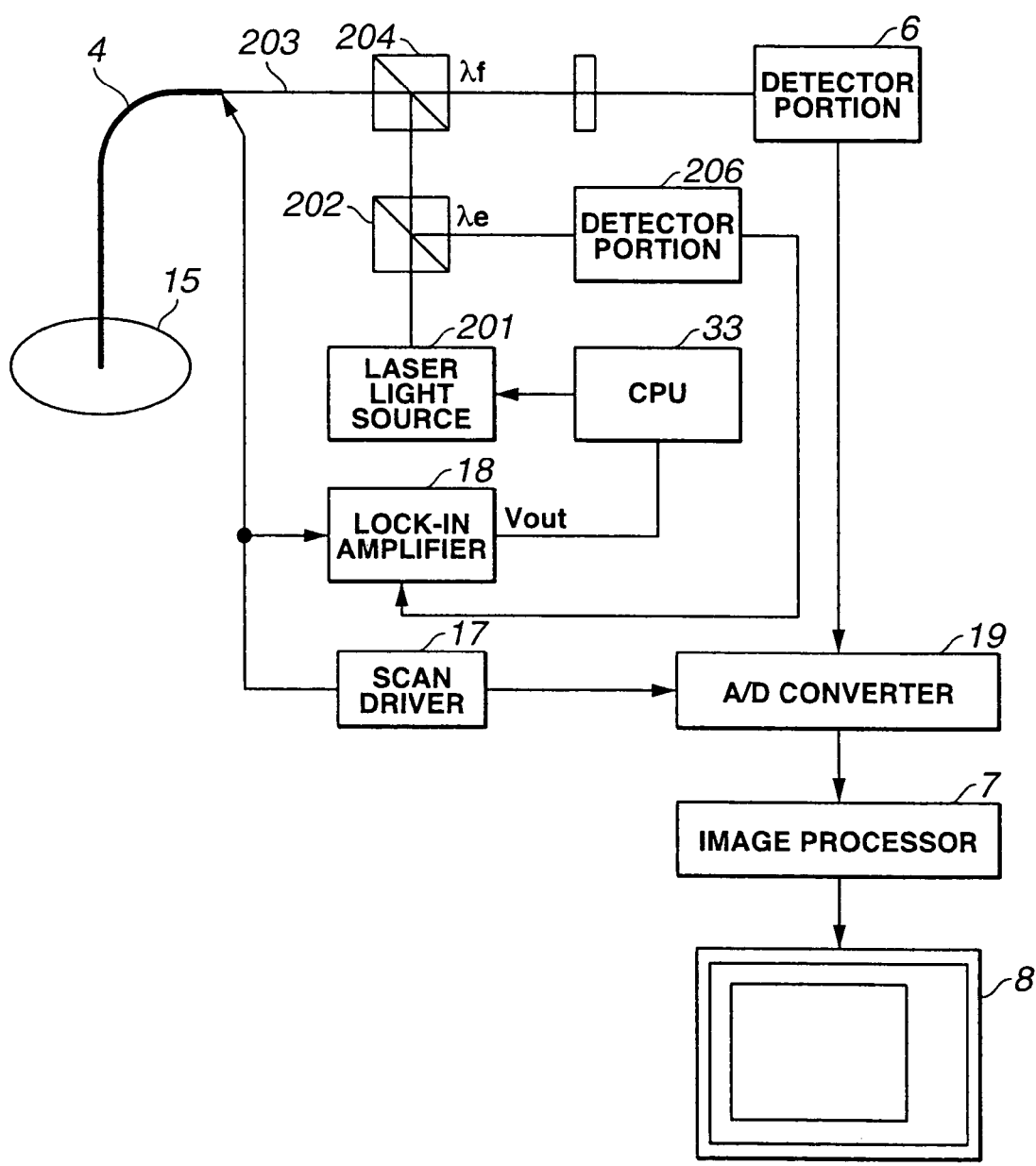

FIG. 40 is a configuration diagram showing a configuration of an optical image pickup apparatus according to a twelfth embodiment of the invention.

Figure 41:
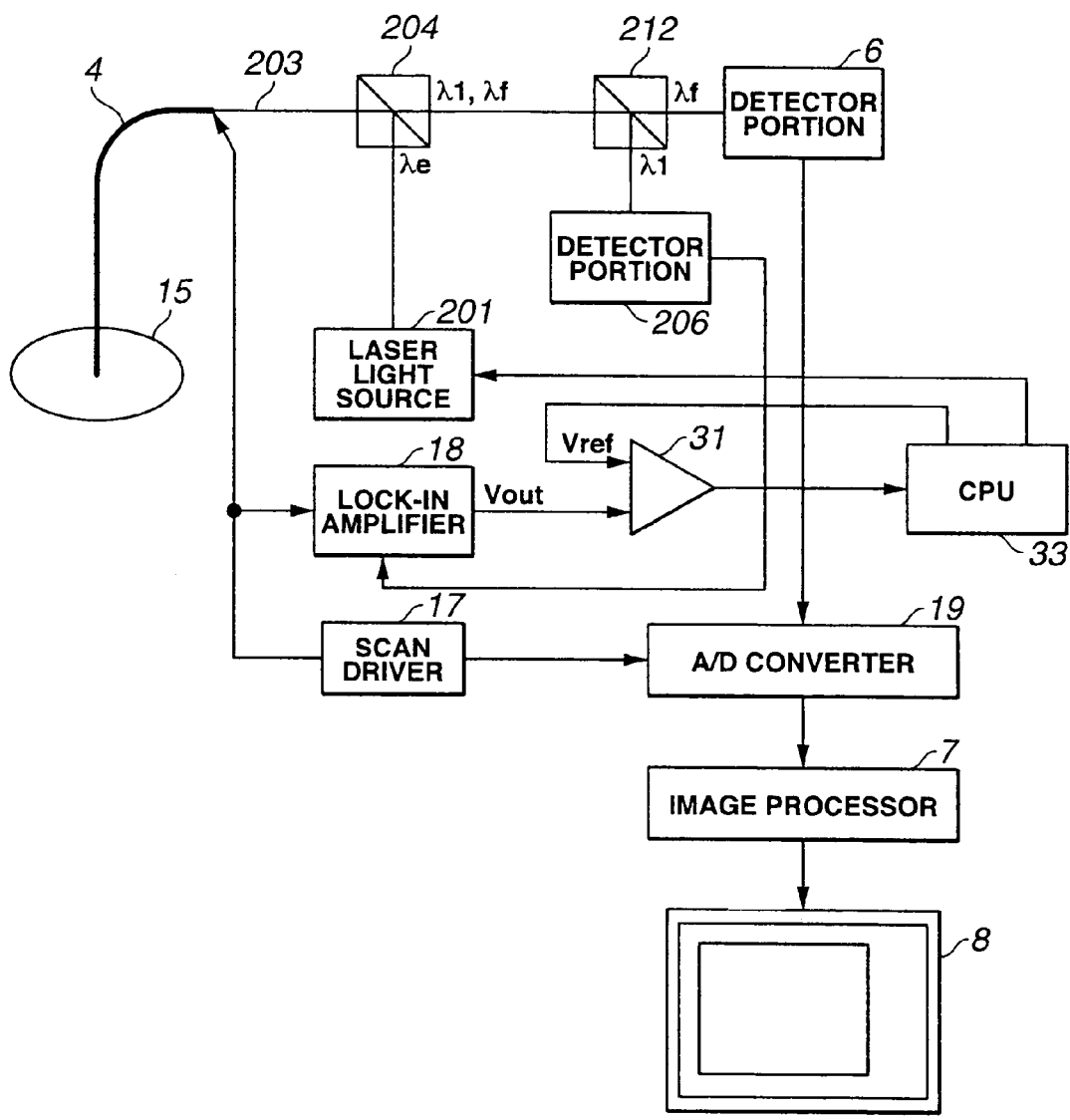
Figure 42:
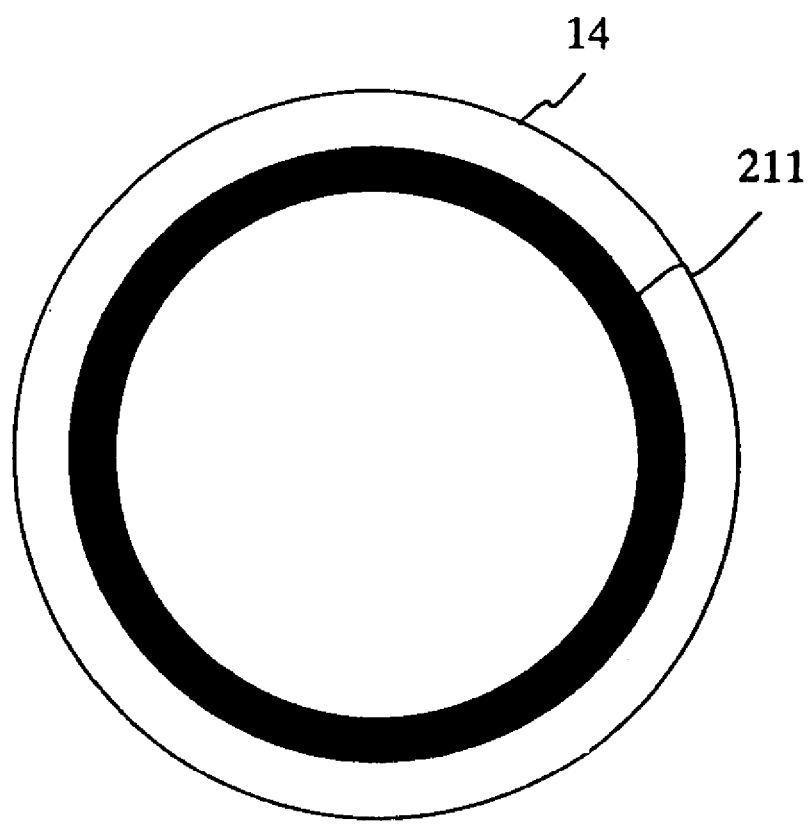

FIGS. 41 and 42 relate to a thirteenth embodiment of the invention. FIG. 41 is a configuration diagram showing a configuration of an optical image pickup apparatus. FIG. 42 is a diagram showing a construction of an objective lens provided at a distal end of an optical scan probe in FIG. 41.

Figure 43:
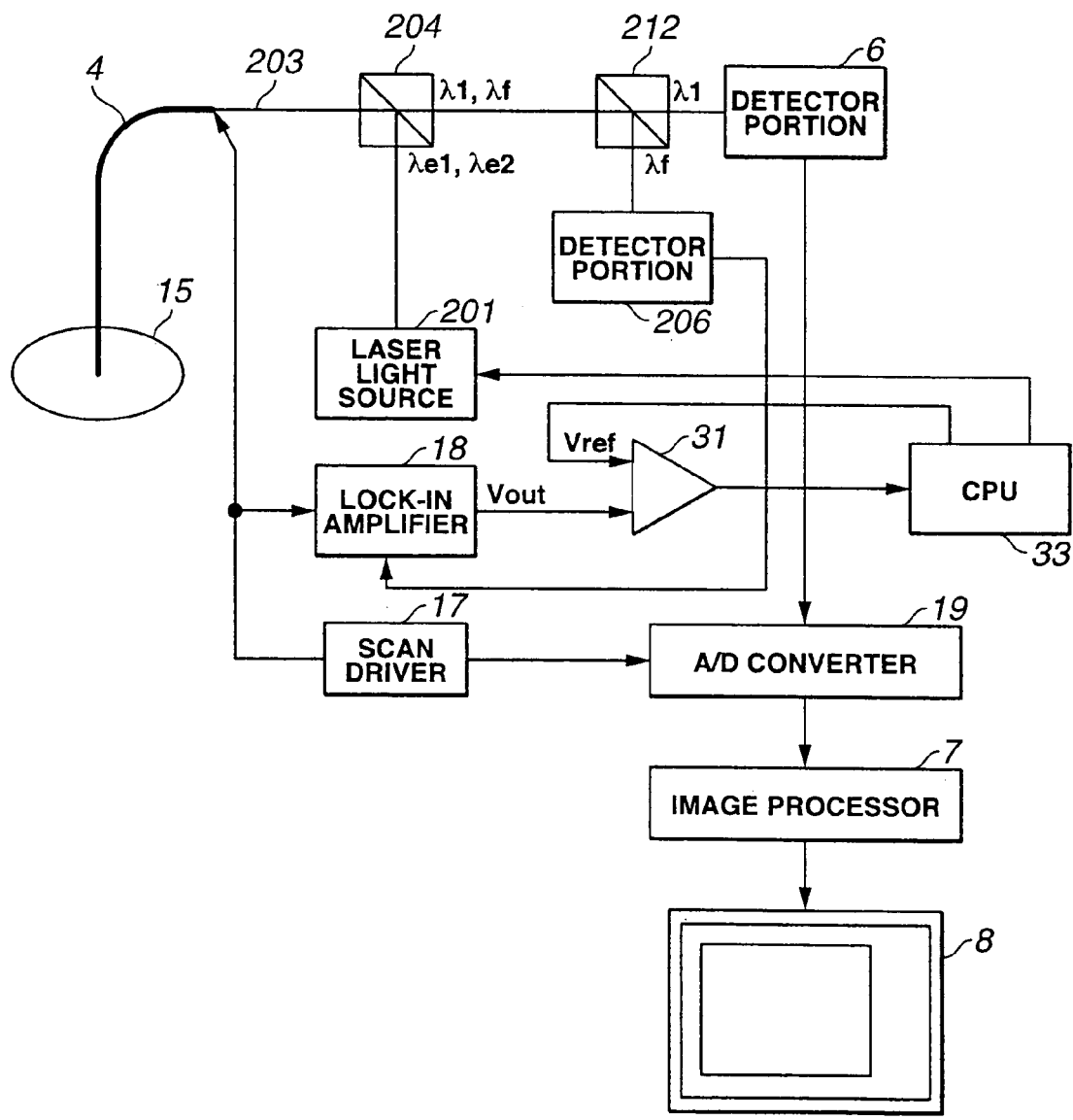

FIG. 43 is a configuration diagram showing a configuration of an optical image pickup apparatus according to a fourteenth embodiment of the invention.

Figure 44:
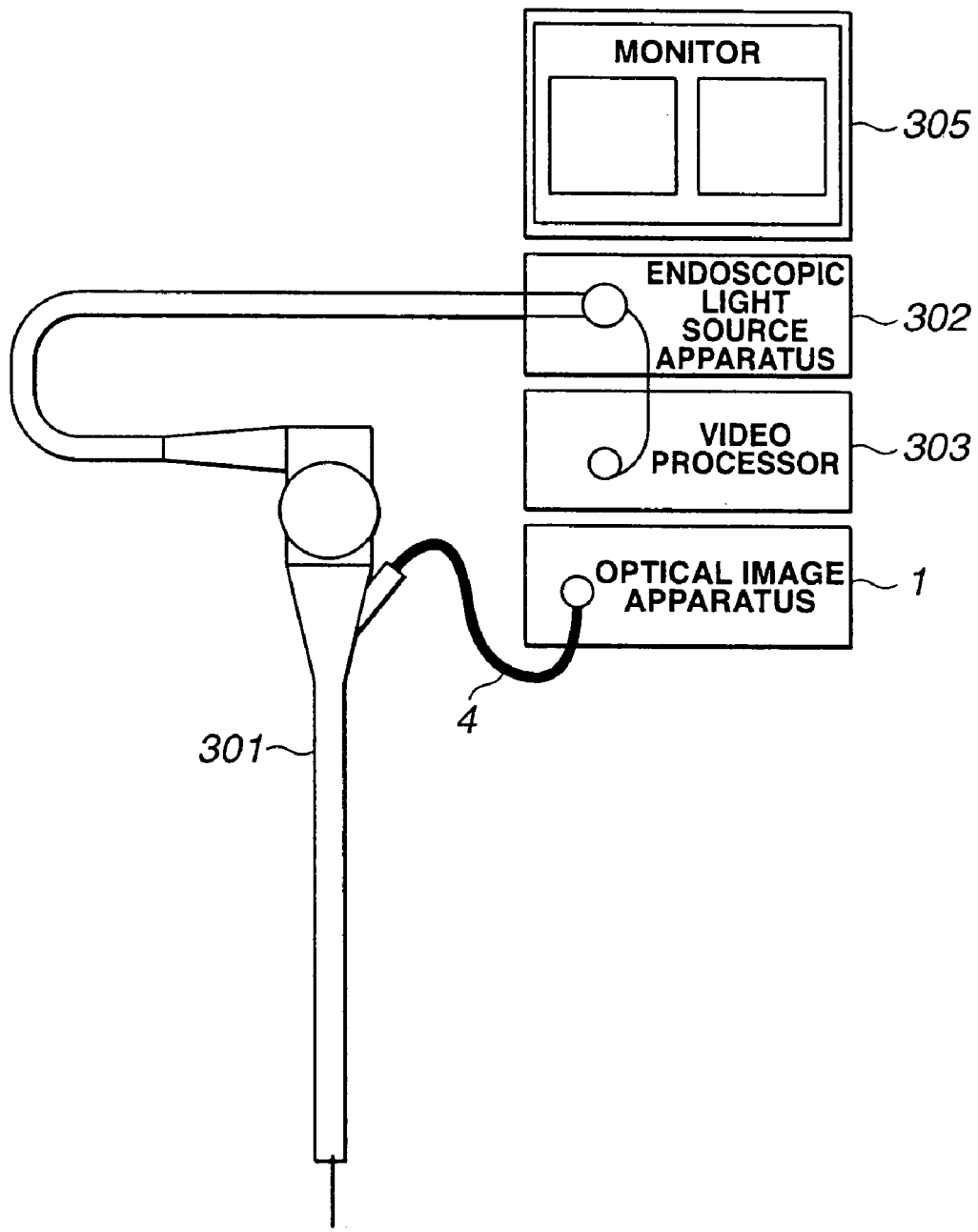

FIG. 44 is a diagram showing an endoscope apparatus as an example of medical equipment, which can use the optical image pickup apparatus according to the first to fourteenth embodiments of the invention.

Figure 45:
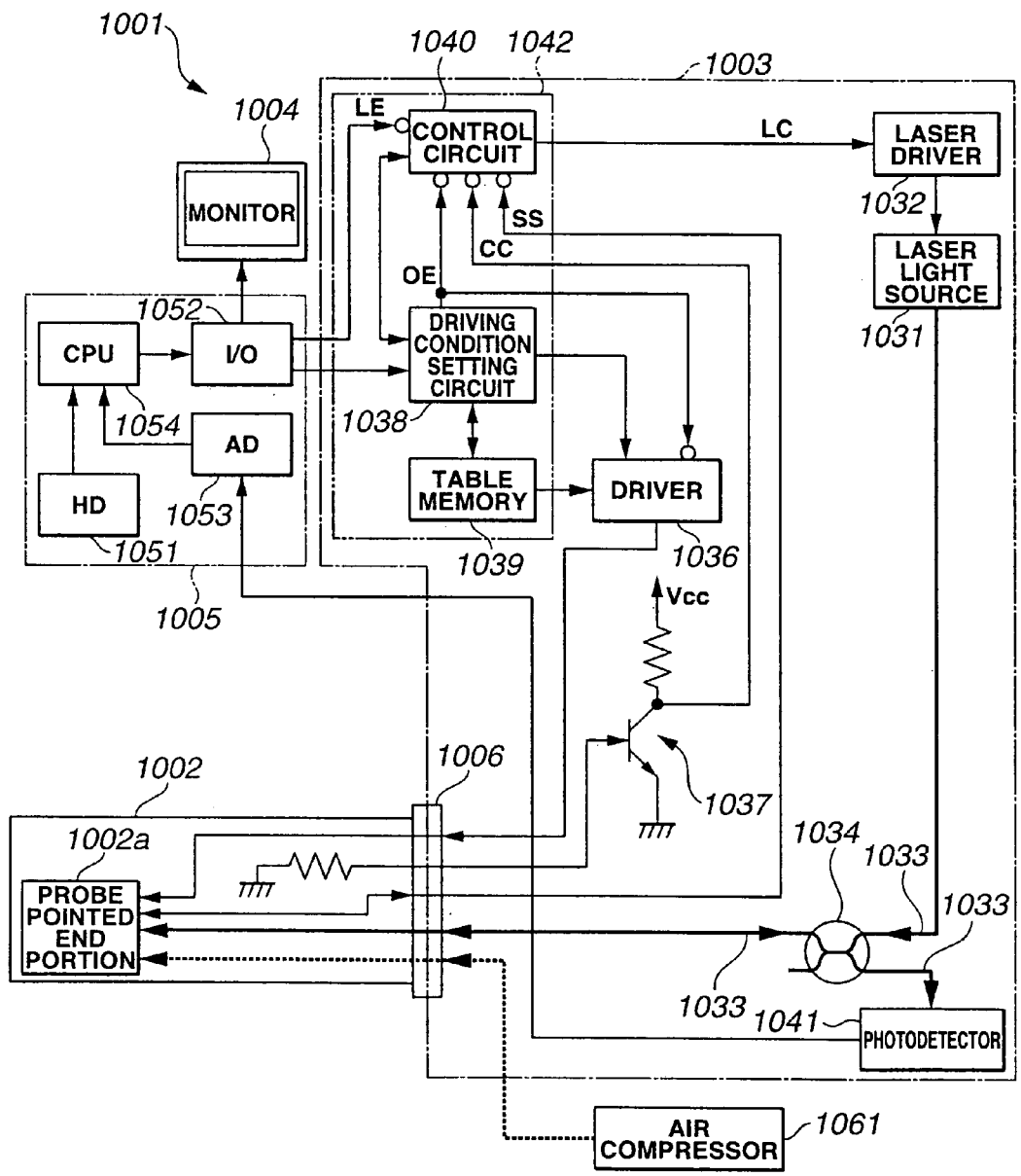
Figure 46:
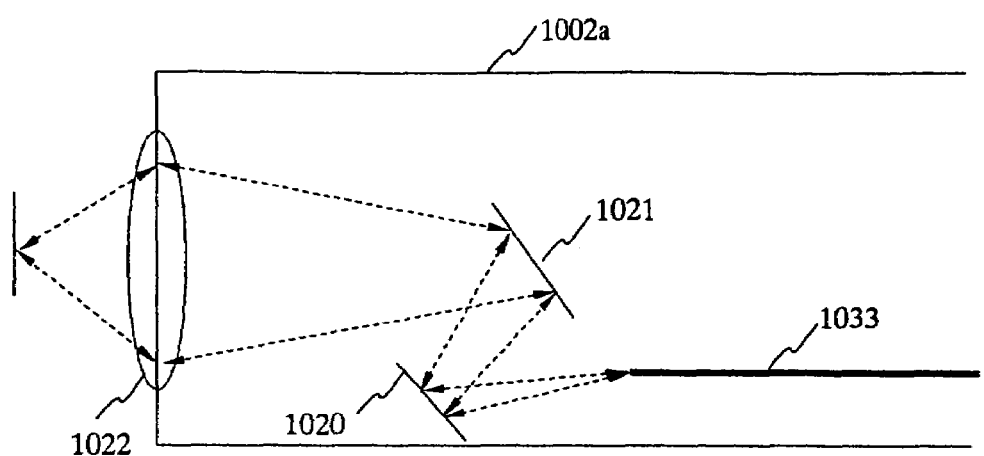
Figure 47:
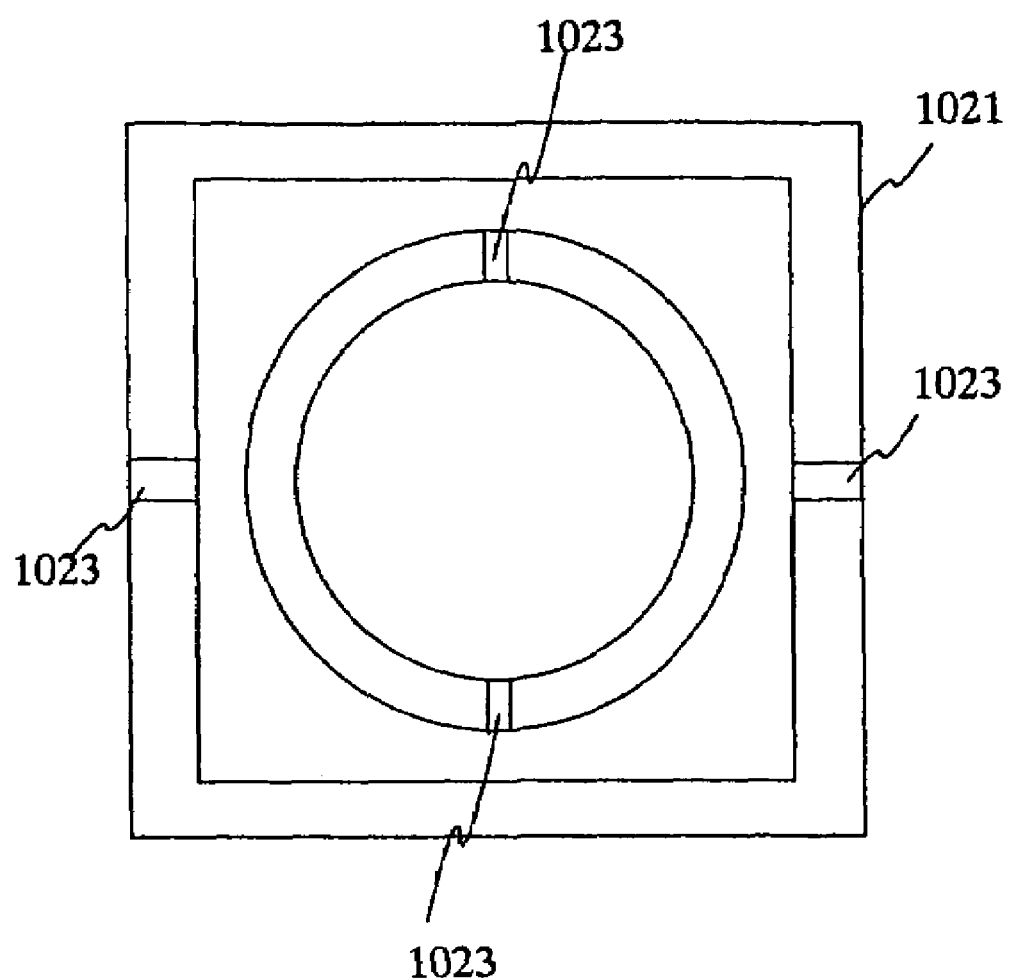
Figure 48:
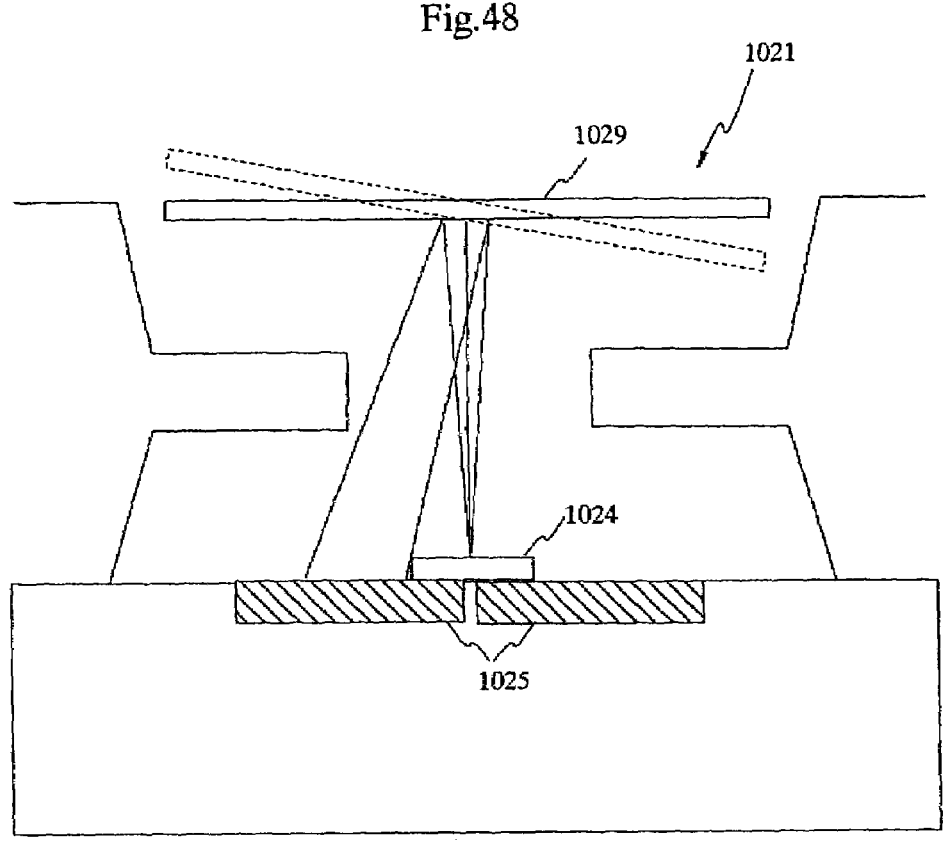
Figure 49:
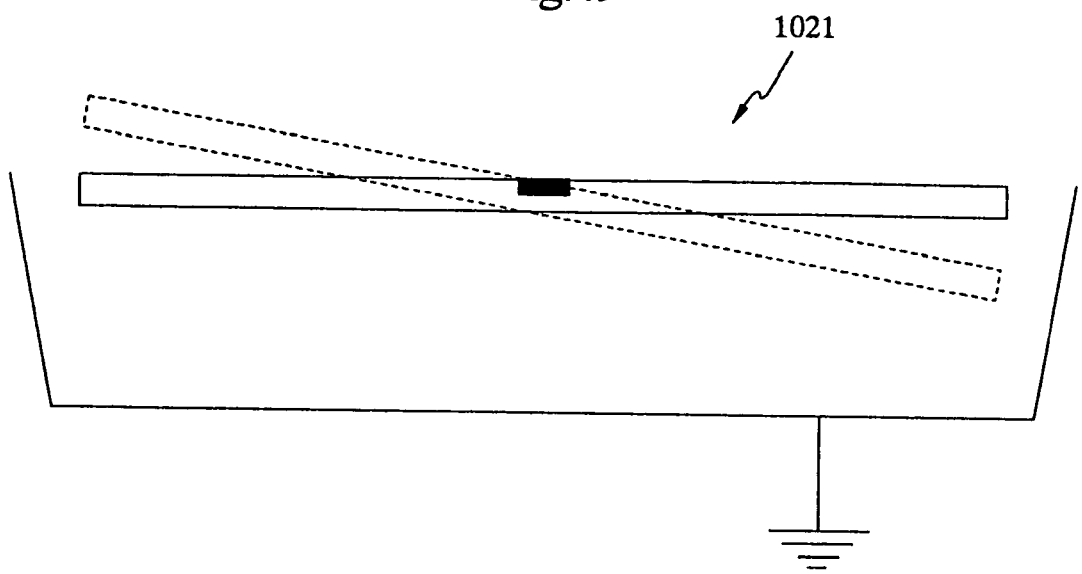
Figure 50:
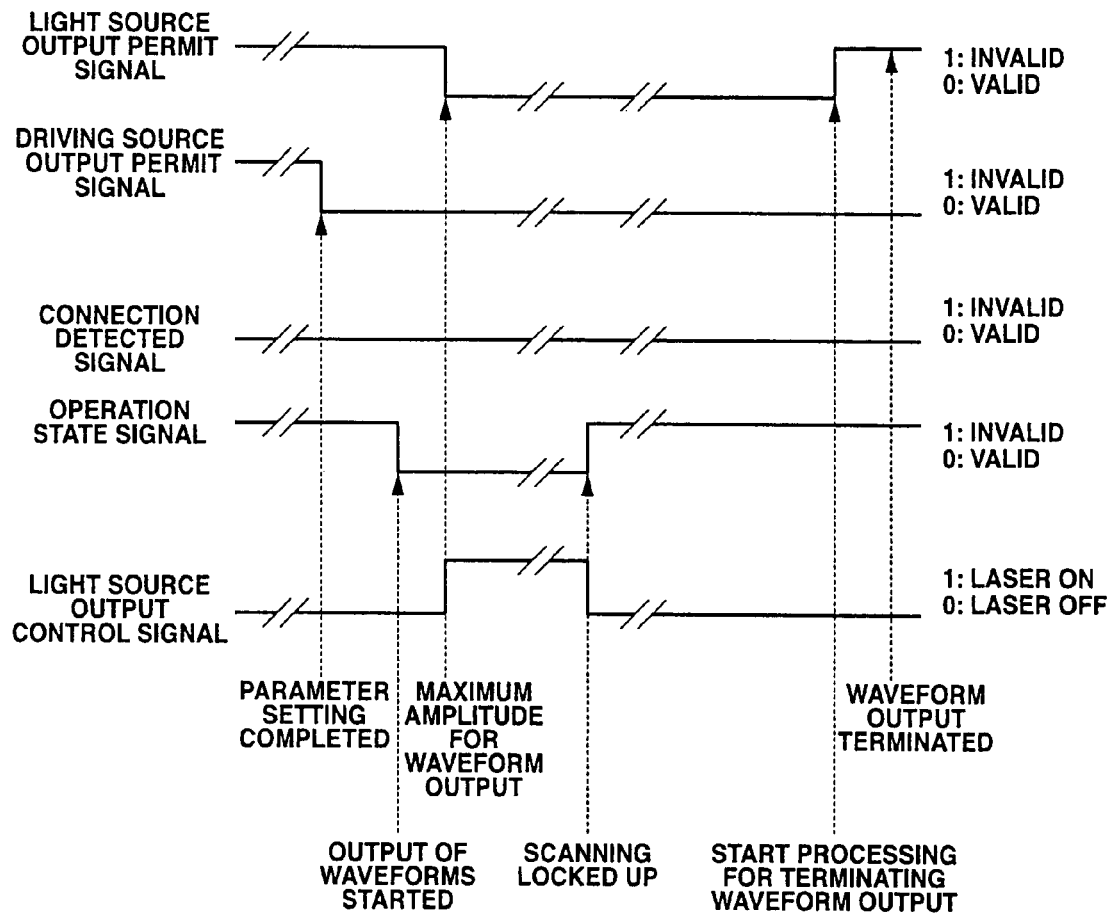
Figure 51:
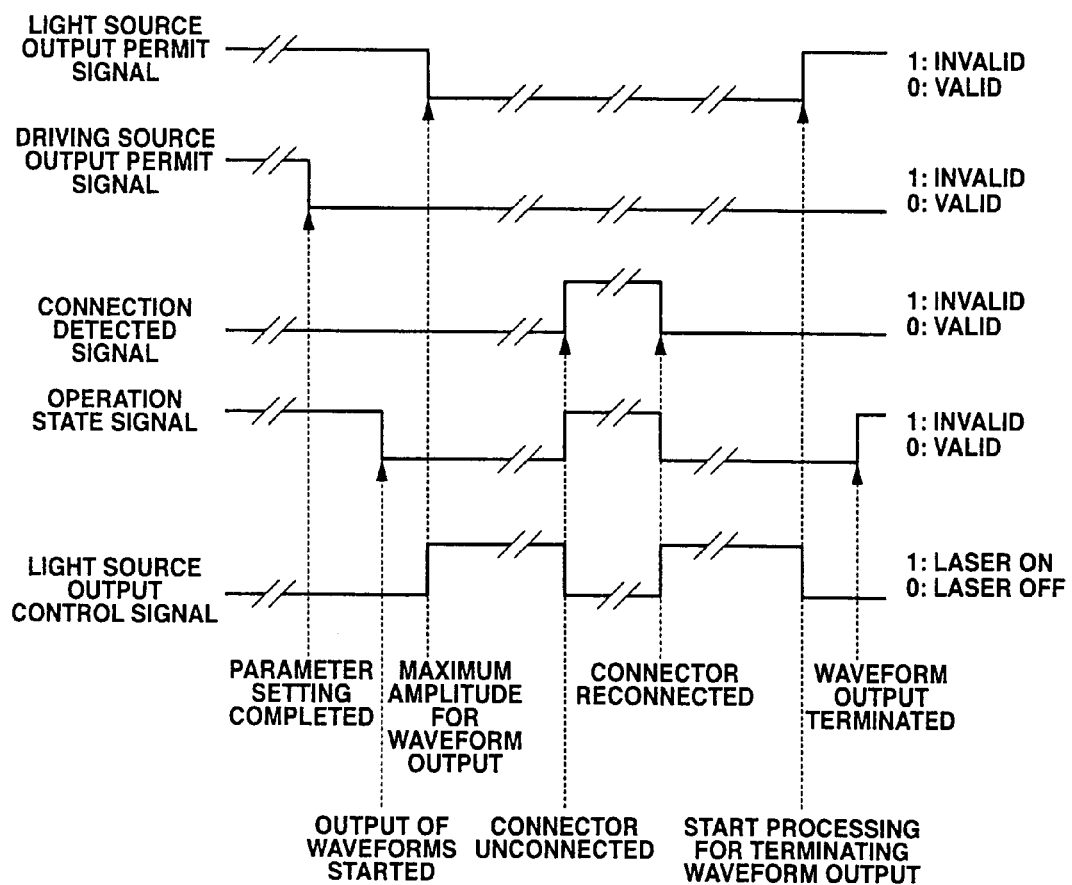
Figure 52:
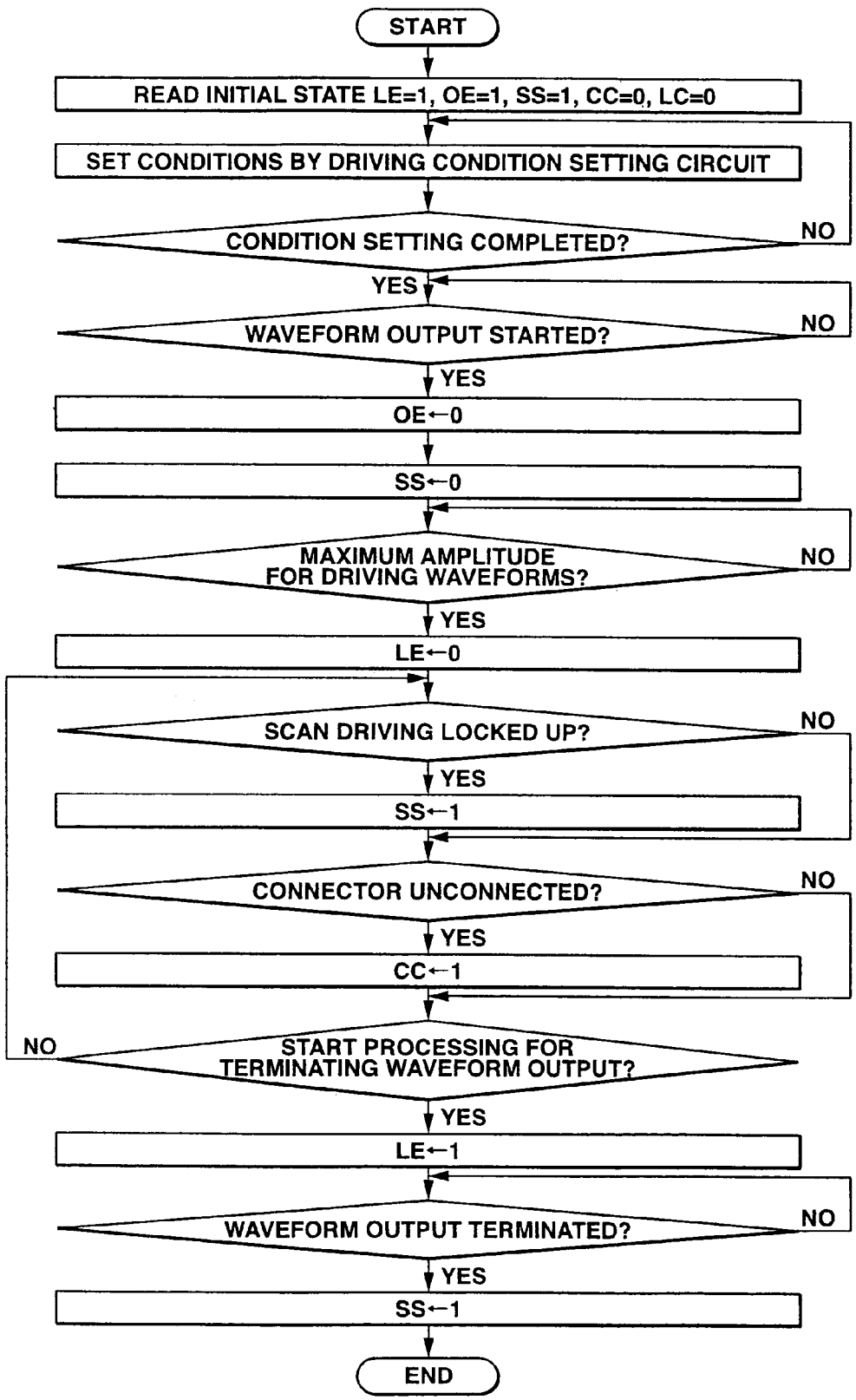
Figure 53:
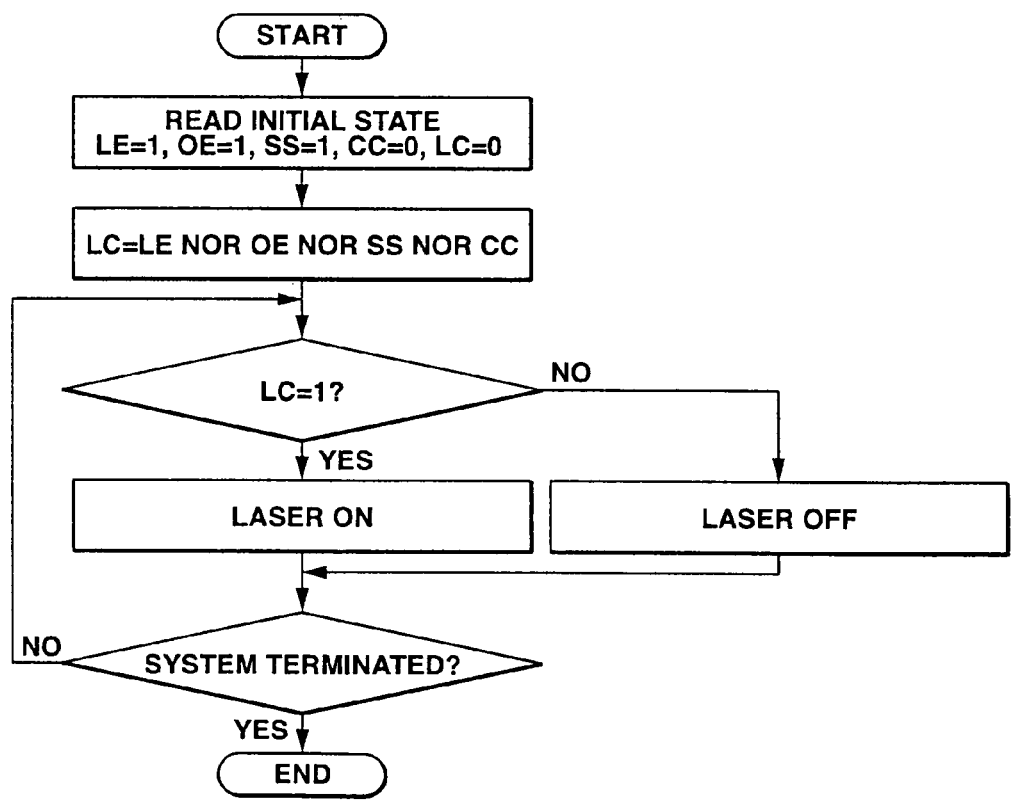
Figure 54:
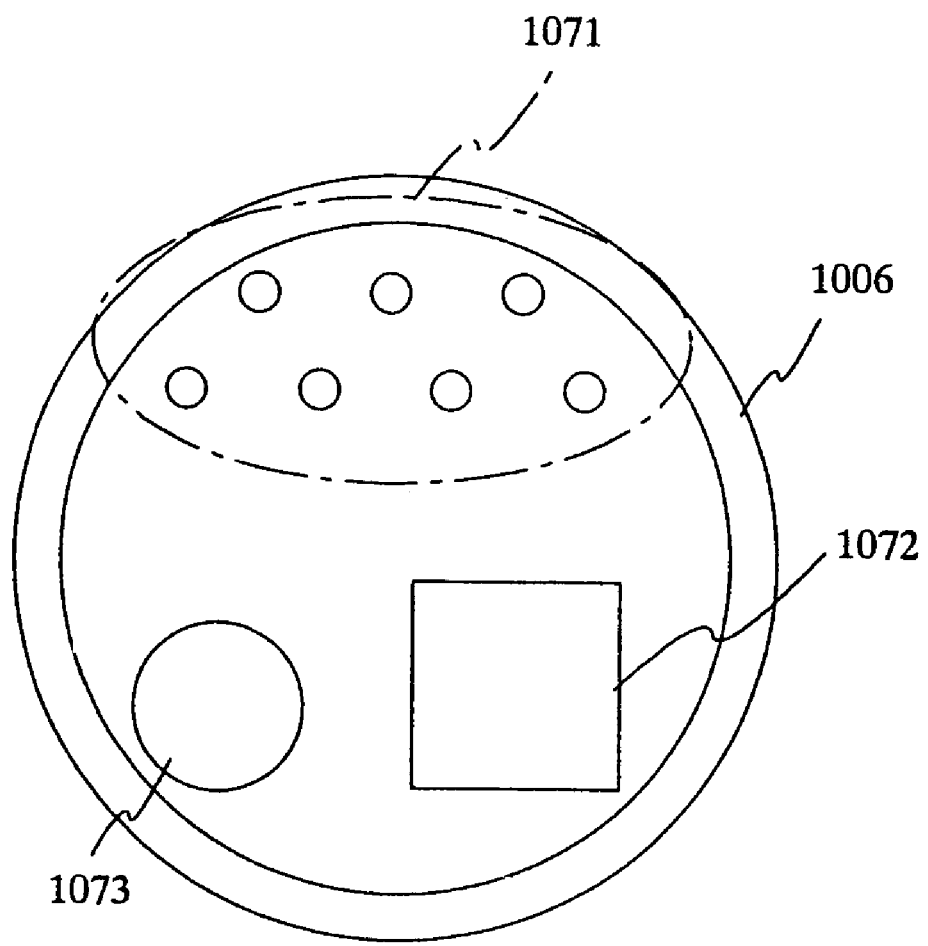
Figure 55:
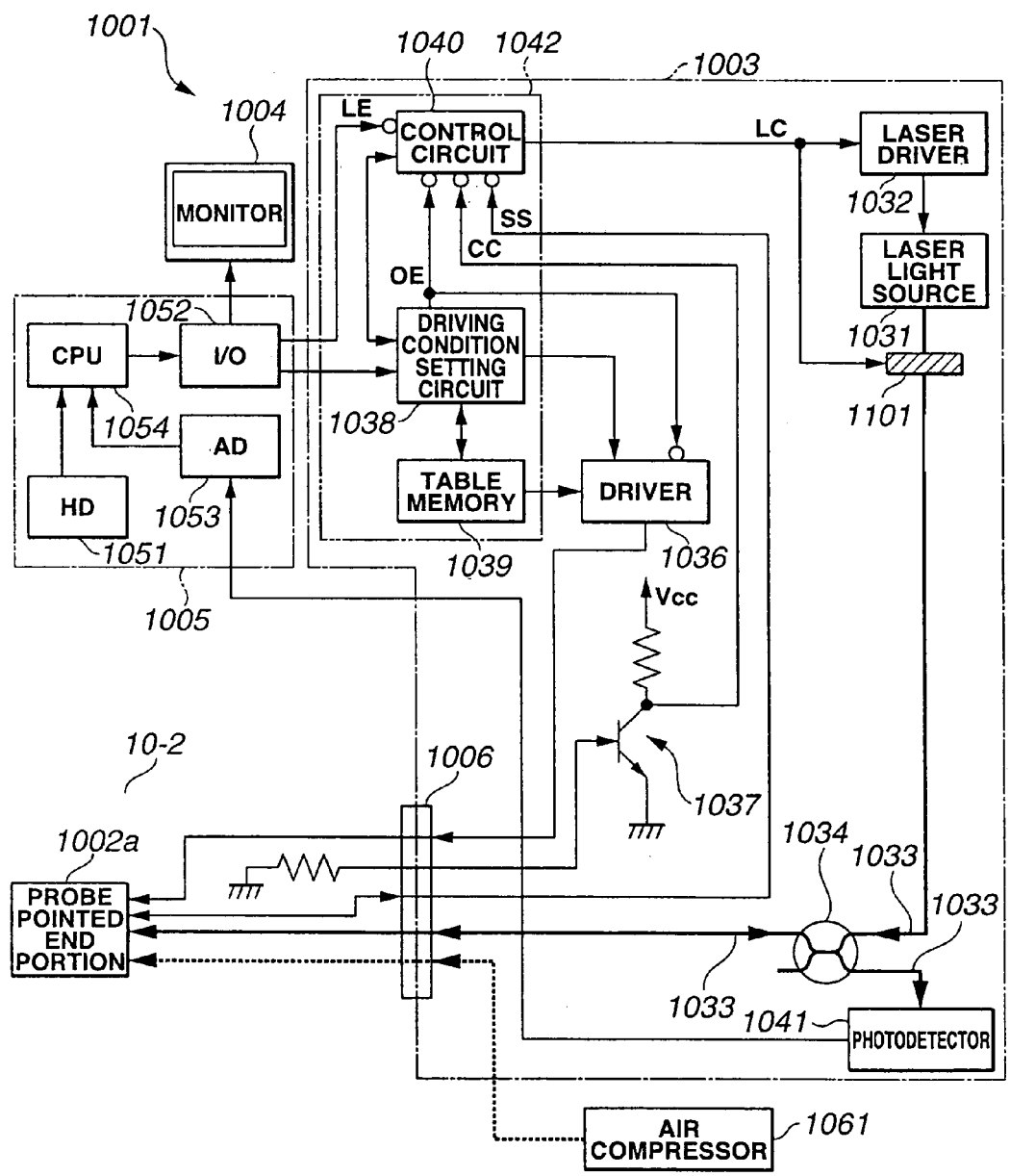
Figure 56:
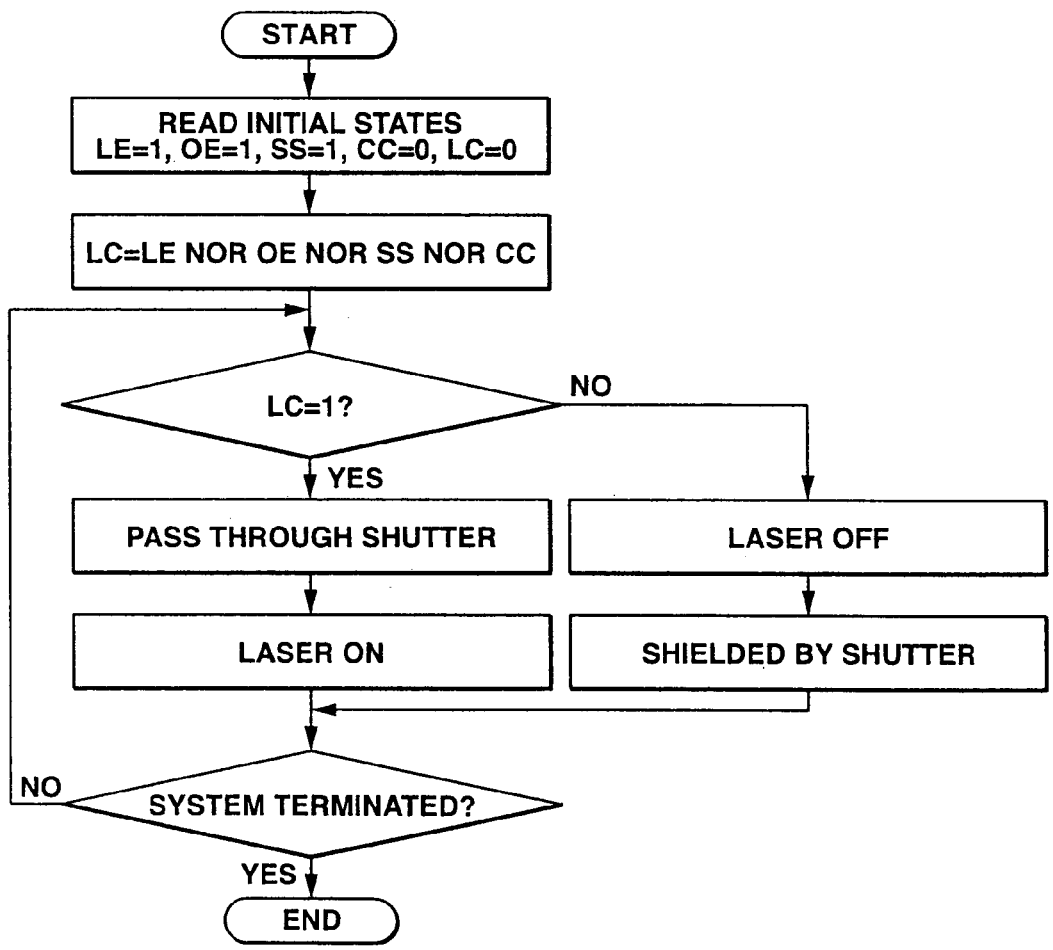

FIGS. 45 to 56 relate to a fifteenth embodiment of the invention. FIG. 45 is a configuration diagram showing a configuration of an optical image pickup apparatus. FIG. 46 is a diagram showing a construction of a probe distal end portion in FIG. 45. FIG. 47 is a first diagram showing a construction of a two-dimensional scanning mirror in FIG. 46. FIG. 48 is a second diagram showing a construction of the two-dimensional scanning mirror in FIG. 46. FIG. 49 is a diagram showing a configuration of a third variation example in which a scanning state of the two-dimensional scanning mirror in FIG. 46 is detected. FIG. 50 is a first diagram showing a relationship of input/output signals of a control circuit in FIG. 45. FIG. 51 is a second diagram showing a relationship of input/output signals of the control circuit in FIG. 45. FIG. 52 is a first flowchart showing a flow of changes in input/output signals of the control circuit in FIG. 45. FIG. 53 is a second flowchart showing a flow of changes in input/output signals of the control circuit in FIG. 45. FIG. 54 is a diagram showing a construction of a connector in FIG. 45. FIG. 55 is a configuration diagram showing a configuration of a variation example of an optical image pickup apparatus in FIG. 45. FIG. 56 is a flowchart showing a flow of changes in input/output signals of a control circuit in FIG. 55.

Figure 57:
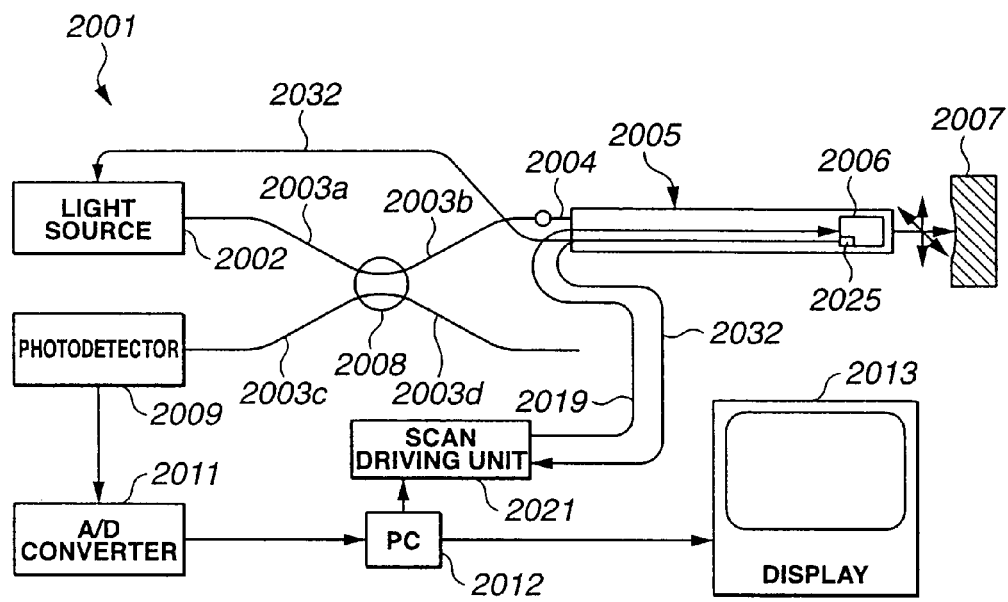
Figure 58:
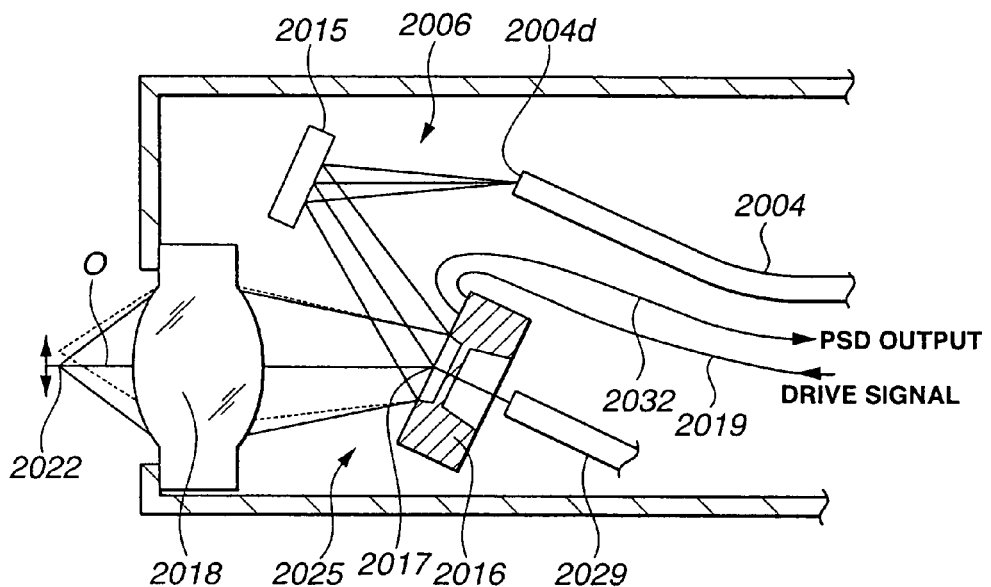
Figure 59A:
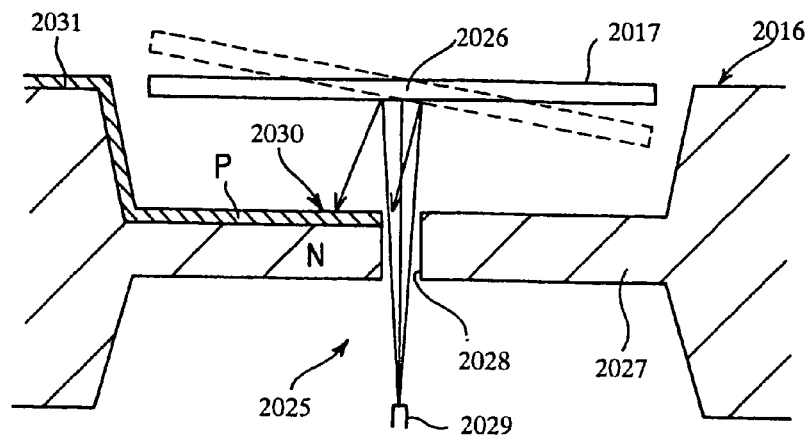
Figure 59B:
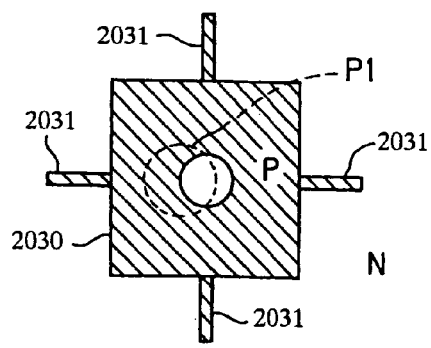
Figure 60:
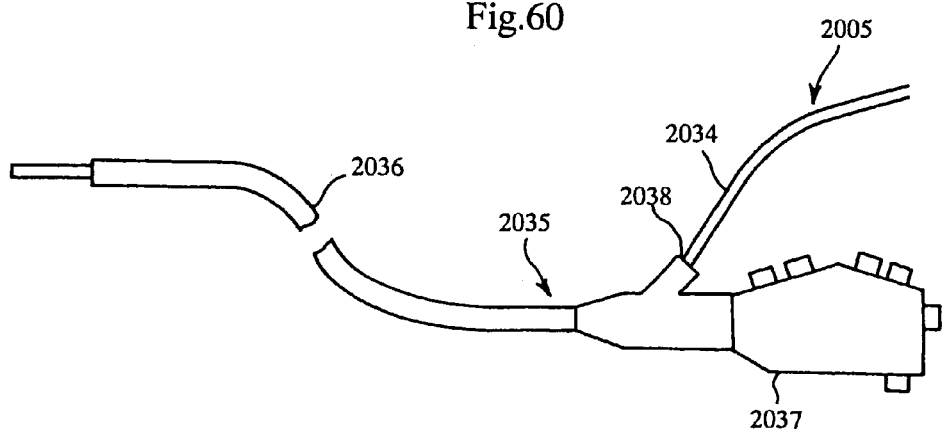

FIGS. 57 to 60 relate to a sixteenth embodiment of the invention. FIG. 57 shows an entire configuration of an optical-image capturing device according to the sixteenth embodiment. FIG. 58 shows a construction of a distal end part of an optical scan probe. FIG. 59A shows a first diagram showing a structure around a mirror portion of a mirror device and a PSD sensor. FIG. 59B shows a second diagram showing the structure around the mirror portion of the mirror device and the PSD sensor. FIG. 60 shows an endoscope having an optical scan probe therethrough.

Figure 61:
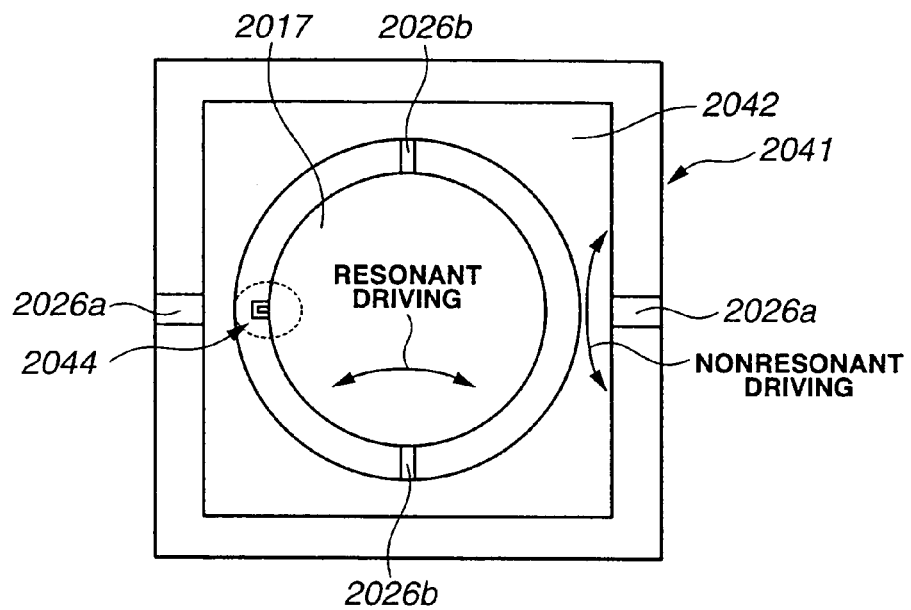
Figure 62A:
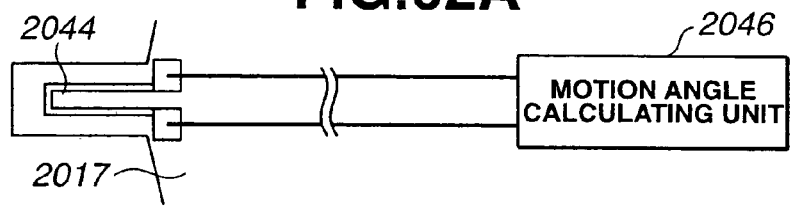
Figure 62B:
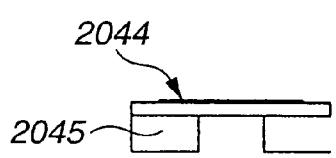
Figure 62C:
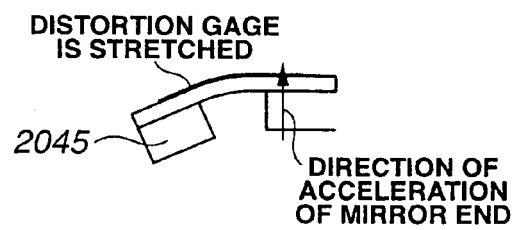

FIGS. 61 to 62C relate to a seventeenth embodiment of the invention. FIG. 61 is a front view of a mirror device according to the seventeenth embodiment. FIG. 62A is a first enlarged diagram showing a strain gauze part provided in a mirror portion in FIG. 61. FIG. 62B is a second enlarged diagram showing the strain gauze part provided in the mirror portion in FIG. 61. FIG. 62C is a third enlarged diagram showing the distorted gauze part provided in the mirror portion in FIG. 61.

Figure 63:
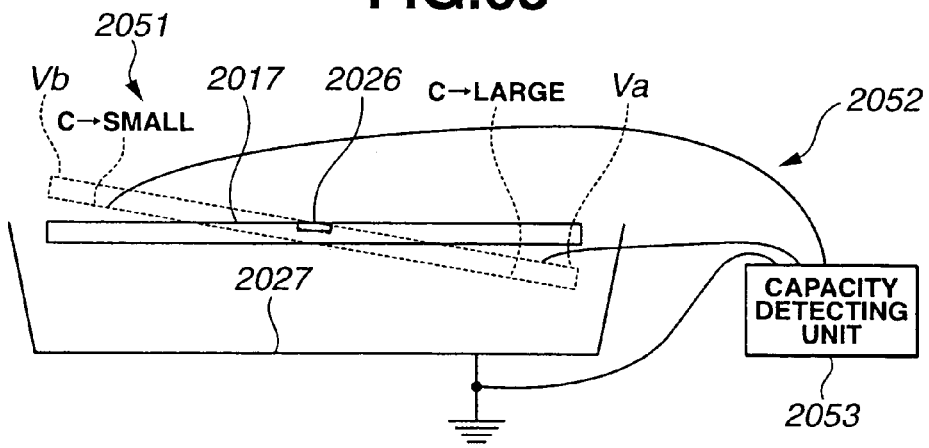

FIG. 63 is a diagram showing a motion-angle detecting mechanism section according to an eighteenth embodiment of the invention.

Figure 64A:
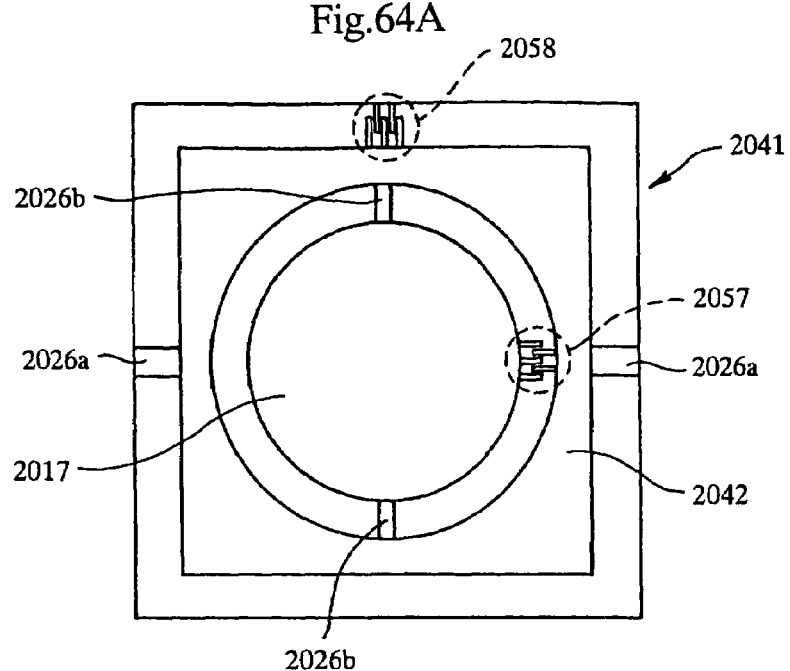
Figure 64B:
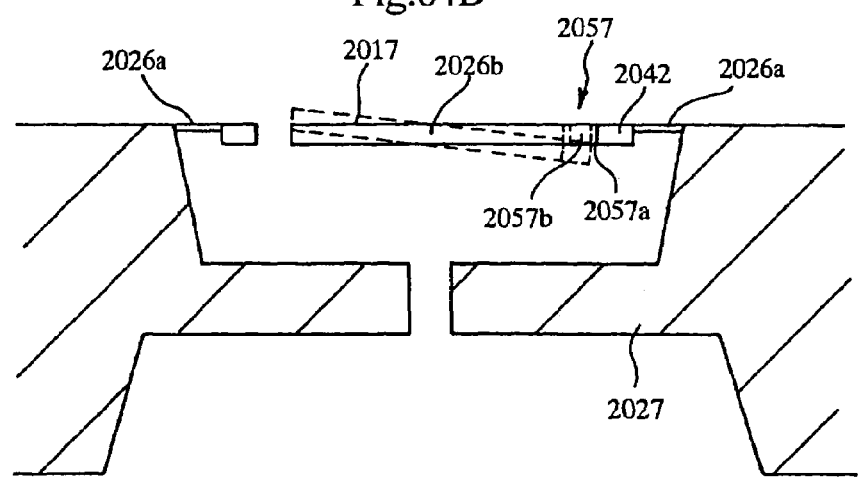

FIGS. 64A and 64B relate to a nineteenth embodiment of the invention. FIG. 64A is a first diagram showing a mirror device having a motion-angle detecting mechanism according to the nineteenth embodiment. FIG. 64B is a second diagram showing the mirror device having the motion-angle detecting mechanism according to the nineteenth embodiment.

Figure 65A:
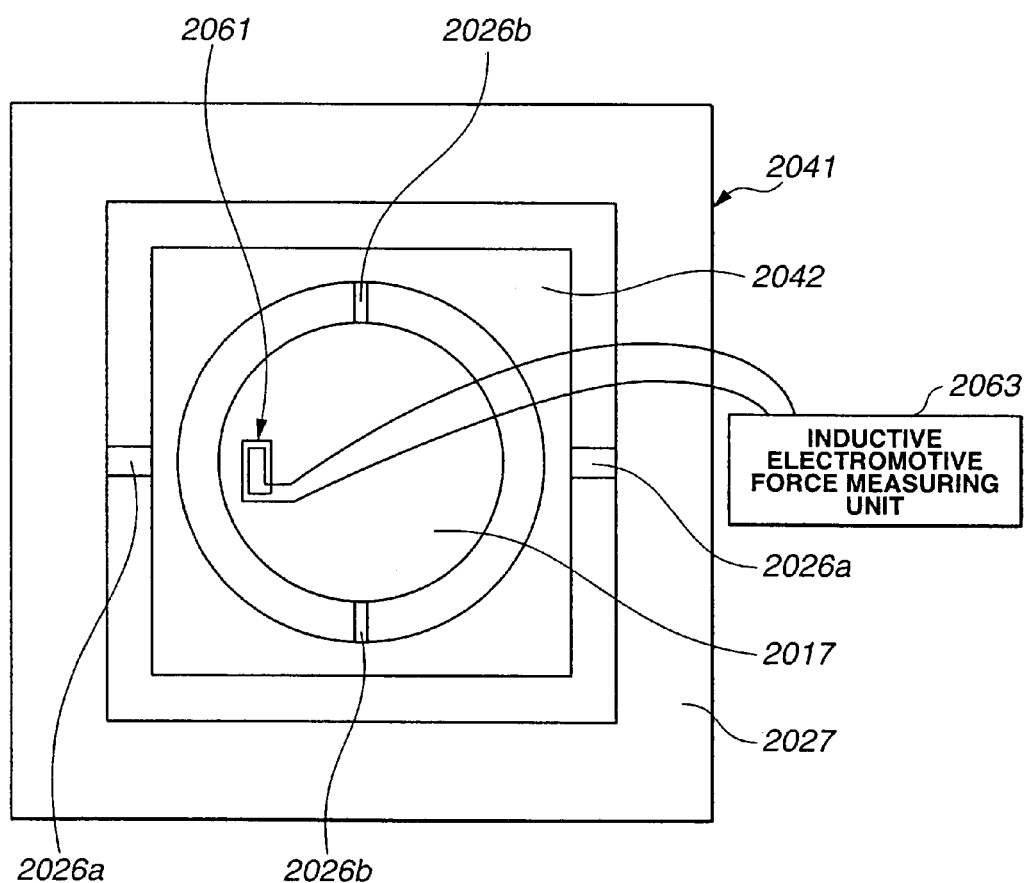
Figure 65B:
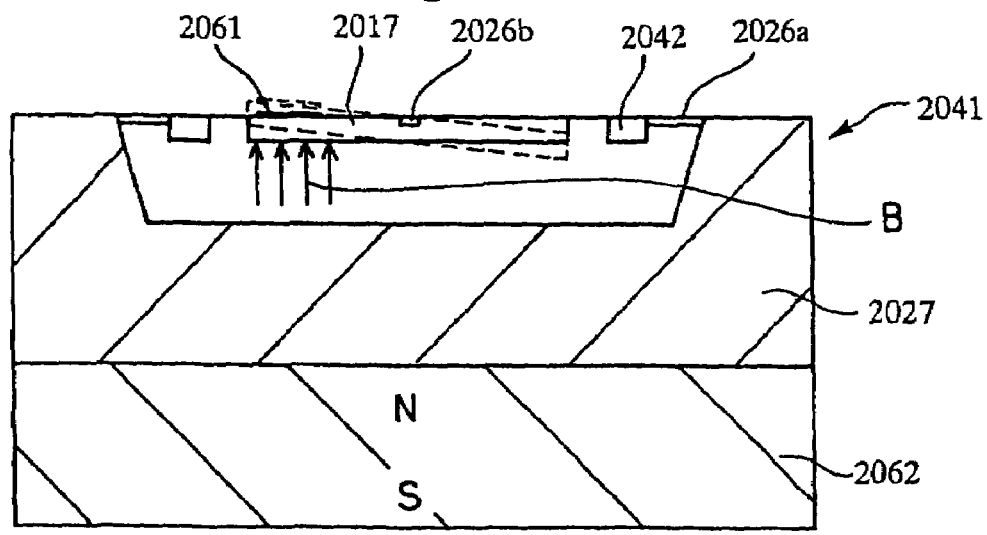

FIGS. 65A and 65B relate to a twentieth embodiment of the invention. FIG. 65A is a first diagram showing a mirror device having a motion-angle detecting mechanism according to the twentieth embodiment. FIG. 65B is a second diagram showing the mirror device having the motion-angle detecting mechanism according to the twentieth embodiment.

Figure 66:
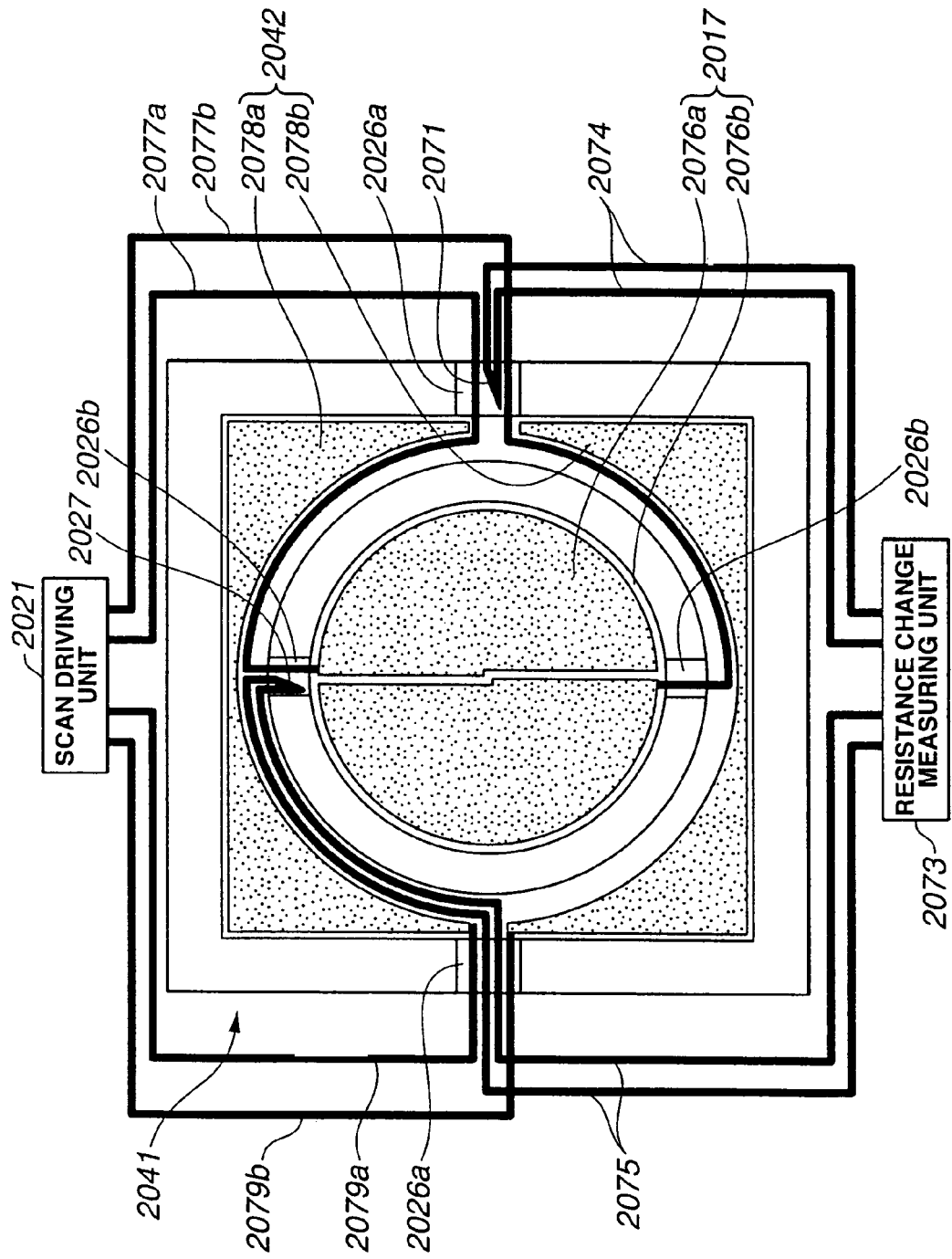

FIG. 66 is a diagram showing a mirror device having a motion-angle detecting mechanism according to a twenty first embodiment of the invention.

Figure 67:
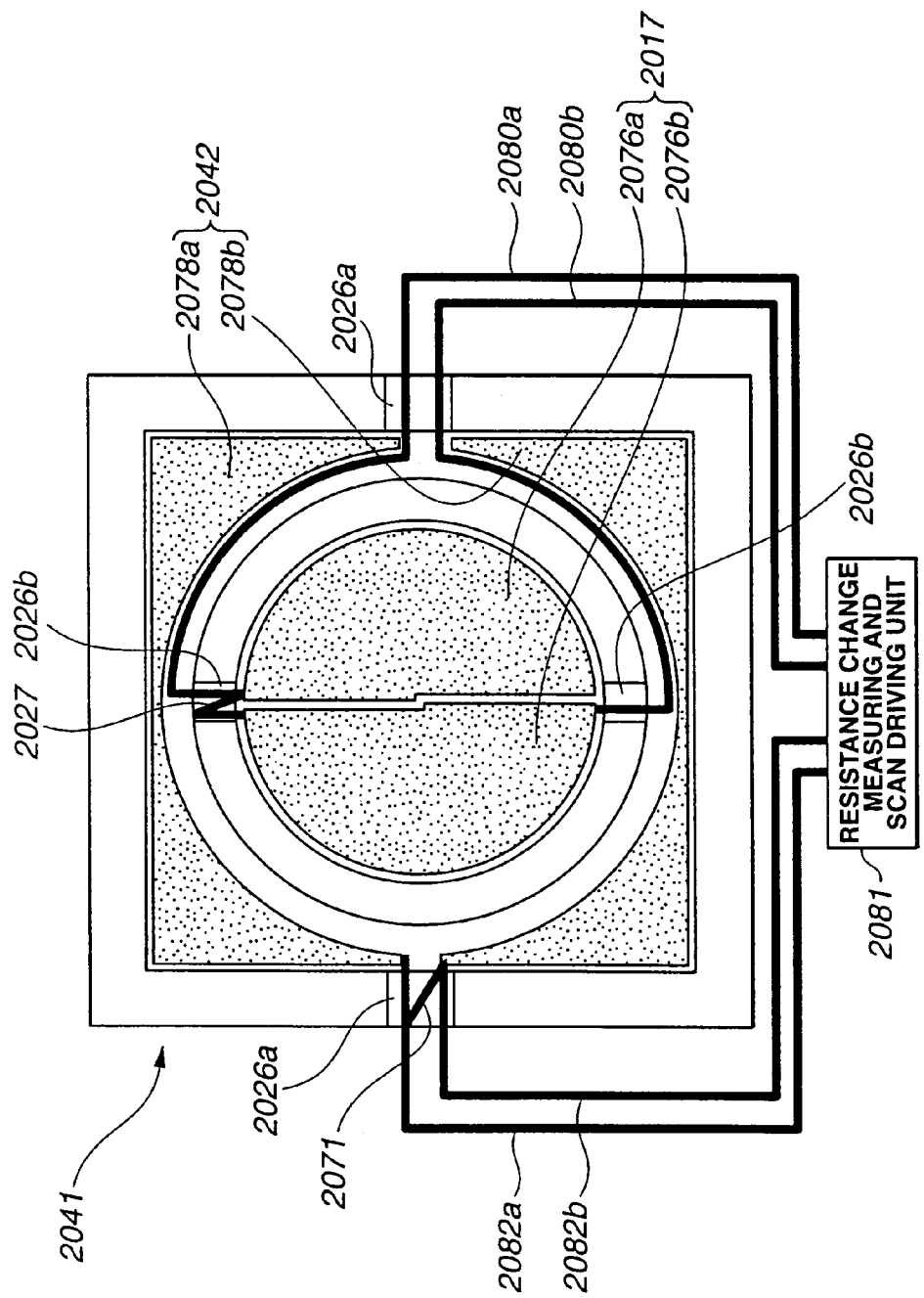

FIG. 67 is a diagram showing a mirror device having a motion-angle detecting mechanism according to a variation example in FIG. 66.

Figure 68A:
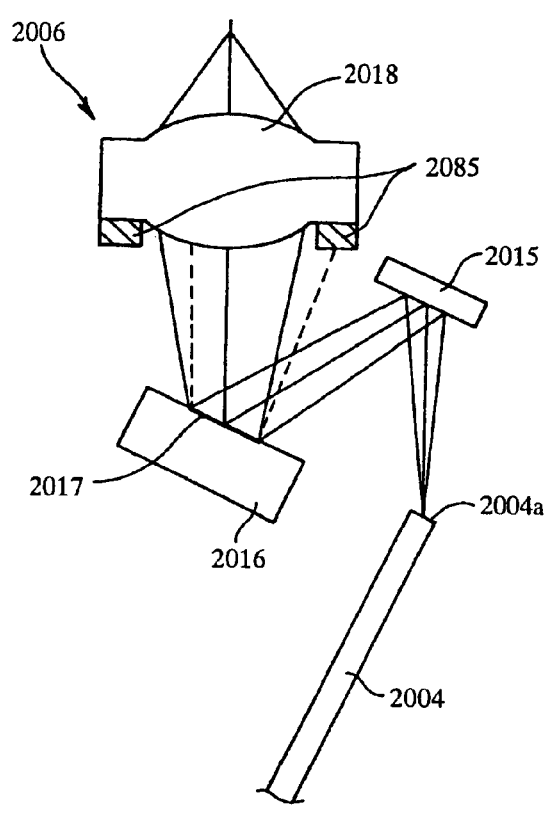
Figure 68B:
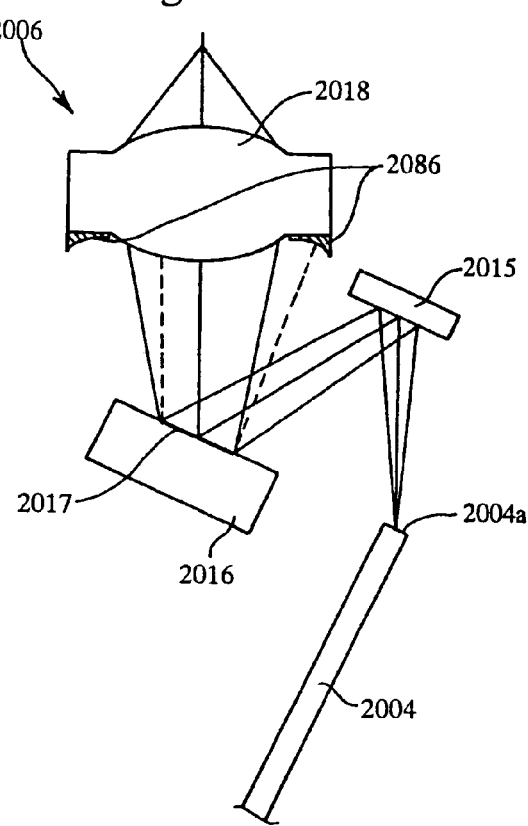

FIGS. 68A and 68B are diagrams showing optical scanning optical systems having motion-angle detecting mechanisms according to a twenty second embodiment and a first variation example of the invention.

Figure 69A:
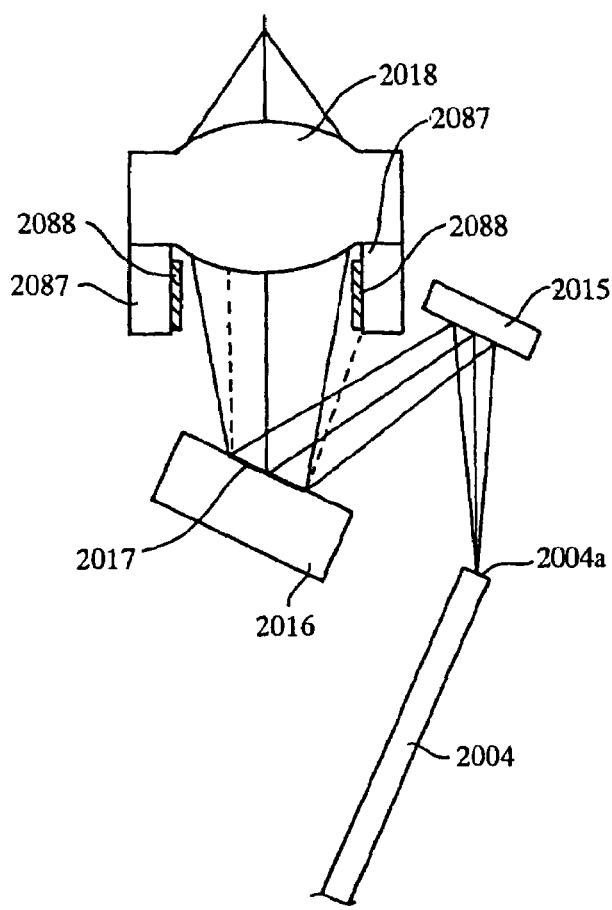
Figure 69B:
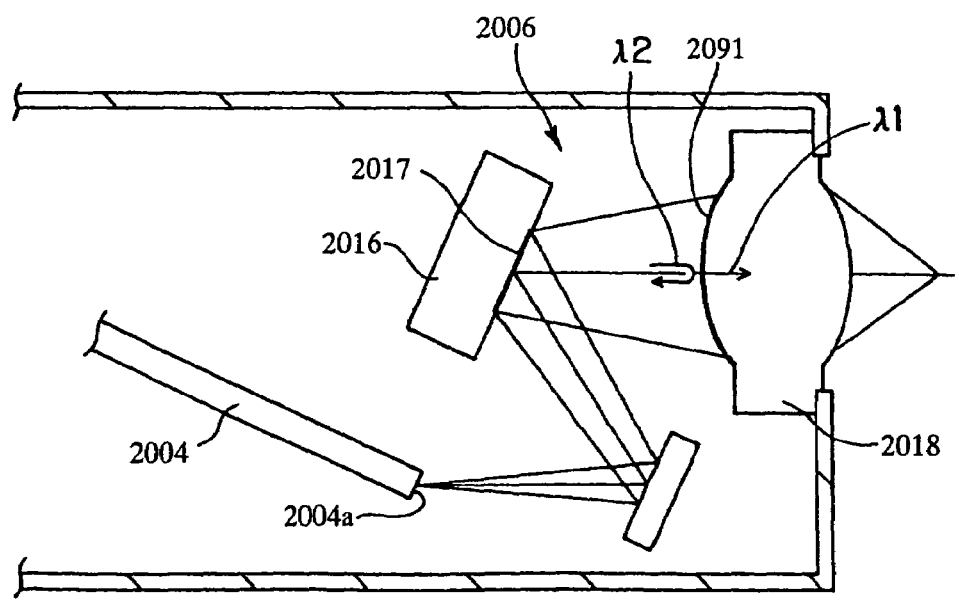

FIGS. 69A and 69B are diagrams showing optical scanning optical systems having a motion-angle detecting mechanism according to second and third variation examples in FIG. 68A.

FIG. 70 is an entire configuration diagram of an optical-image capturing apparatus according to the third variation example in FIG. 68A.

Figure 71:
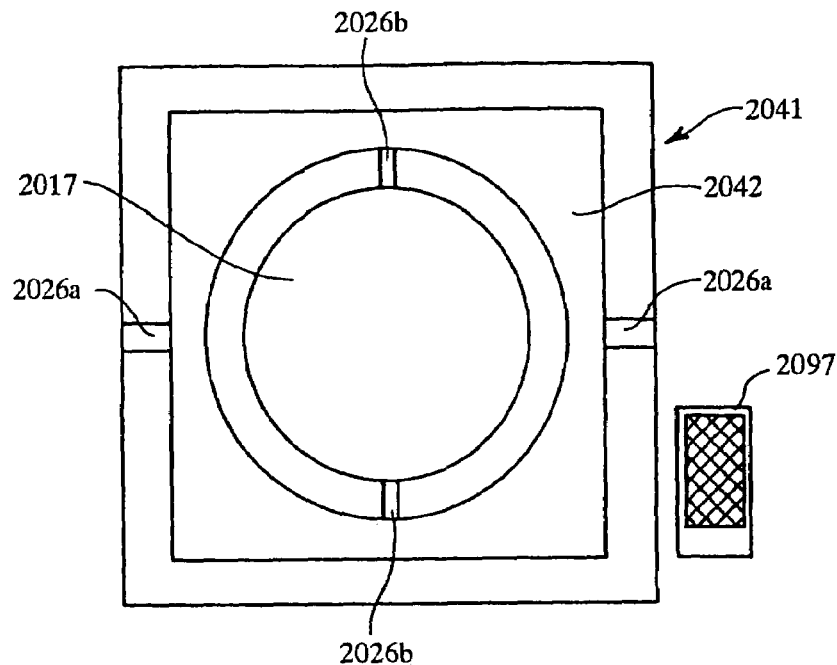

FIG. 71 is a diagram showing motion-angle operation determining means provided in the periphery of a mirror device according to a twenty third embodiment of the invention.

Figure 72:
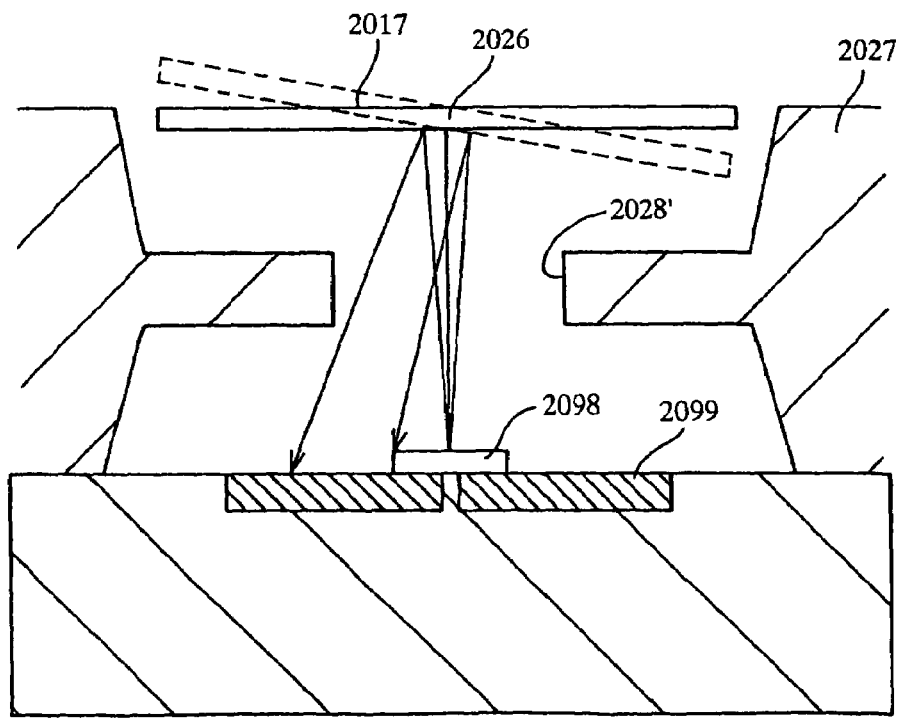

FIG. 72 is a diagram showing a motion-angle detecting mechanism section in a mirror device according to a twenty fourth embodiment of the invention.

Figure 73:
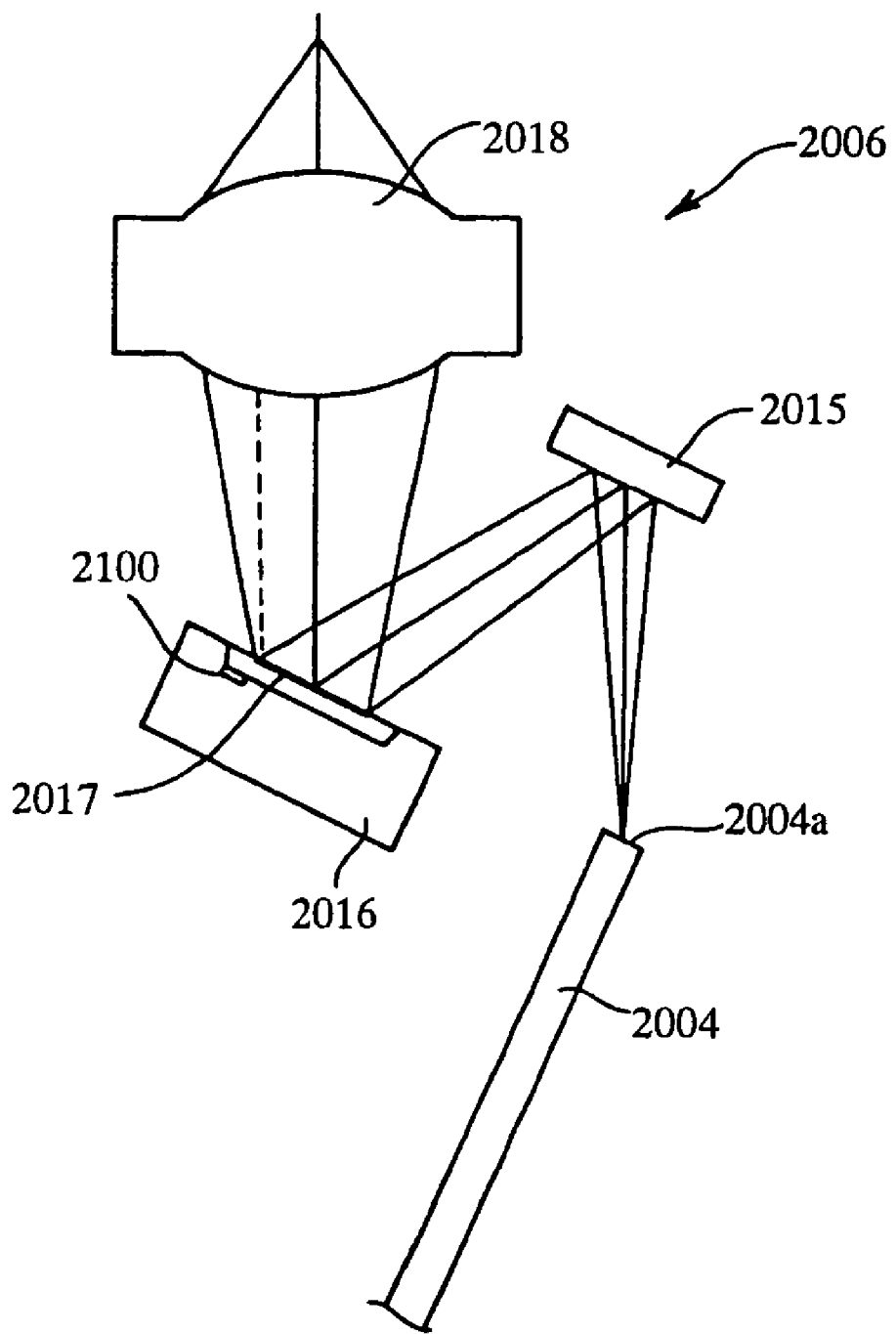
Figure 74B:
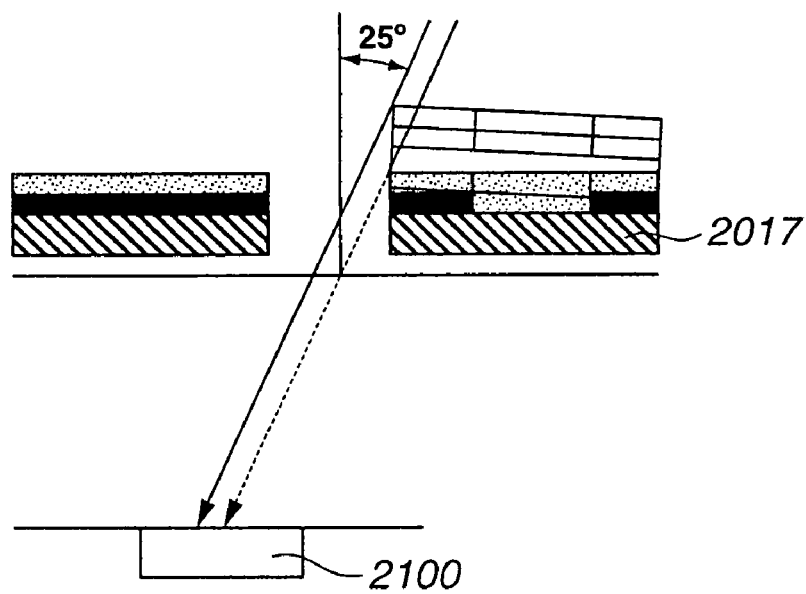
Figure 74A:
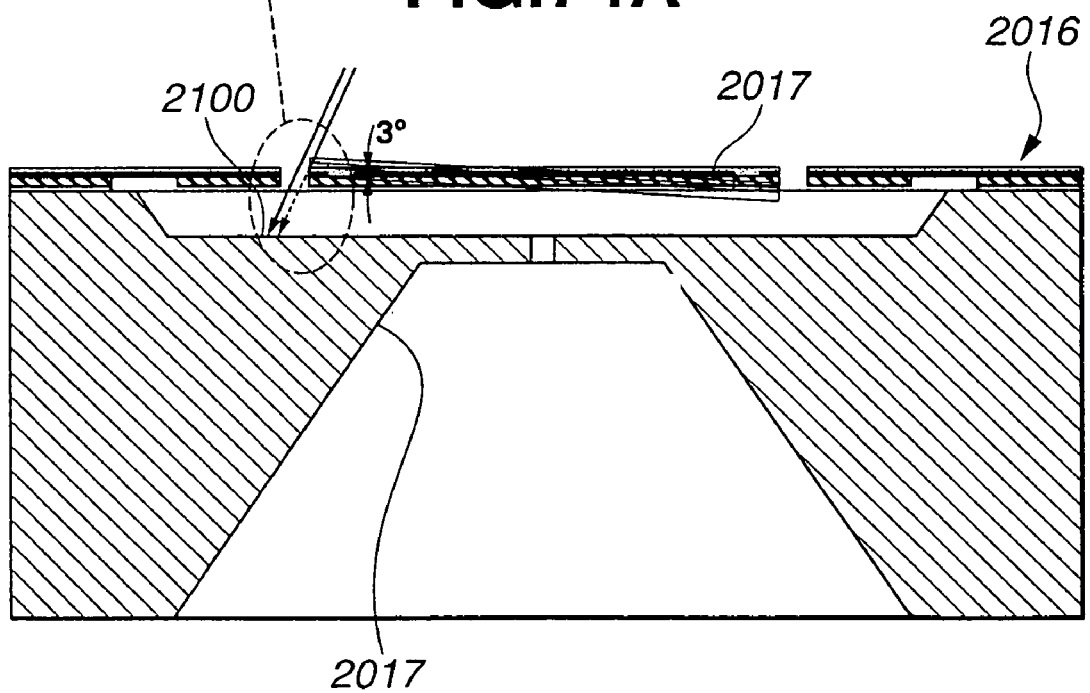

FIGS. 73 to 74B relate to a twenty fifth embodiment of the invention. FIG. 73 is a diagram showing an optical scanning optical system having a motion-angle detecting mechanism according to the twenty fifth embodiment. FIG. 74A is a diagram showing a mirror device in FIG. 73. FIG. 74B is an enlarged diagram showing a part of FIG. 74A.

Figure 75:
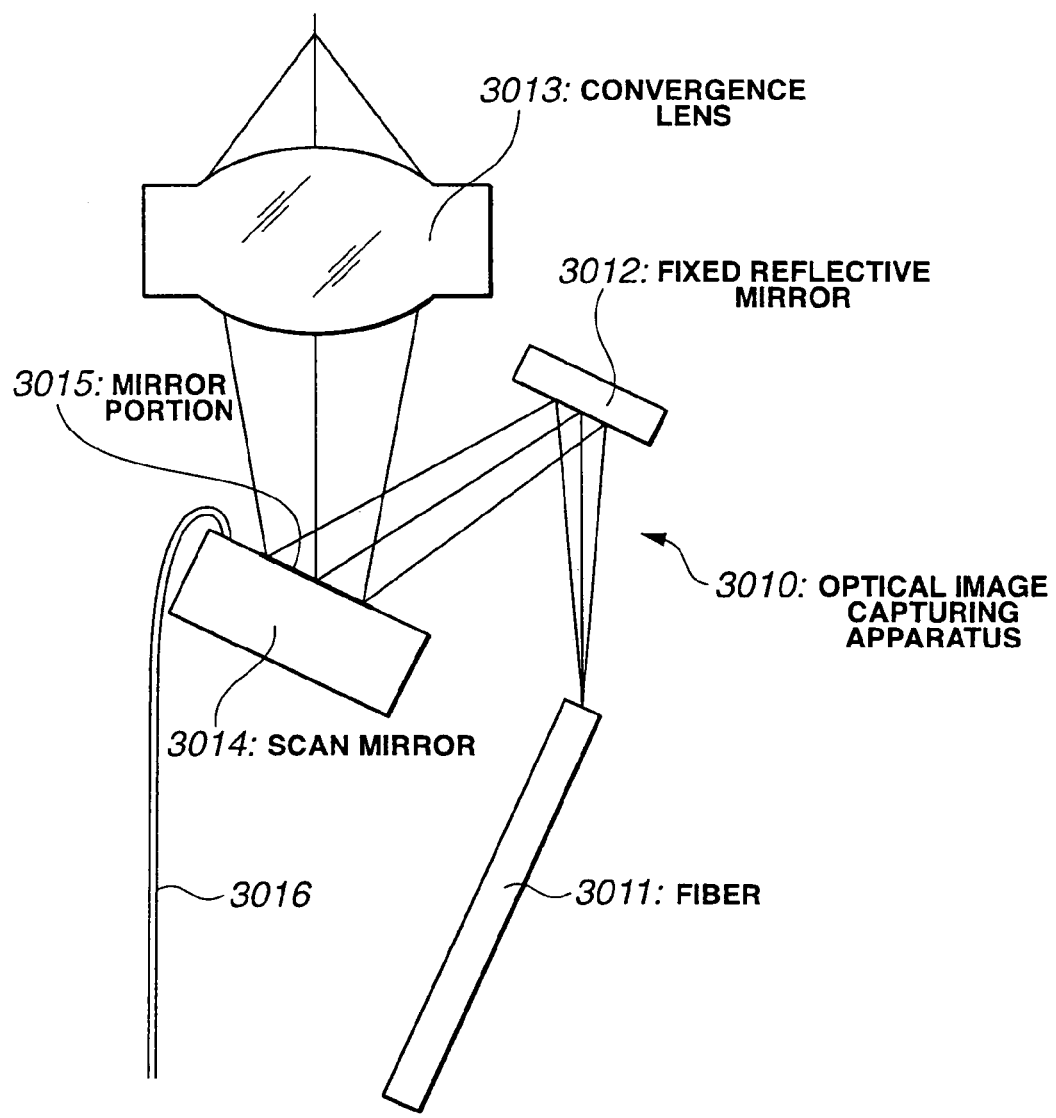
Figure 76:
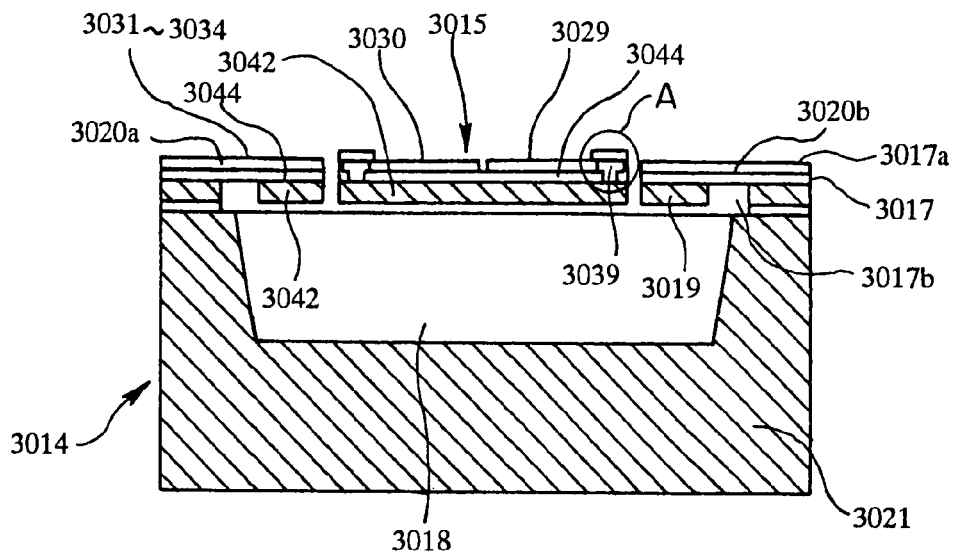
Figure 77:
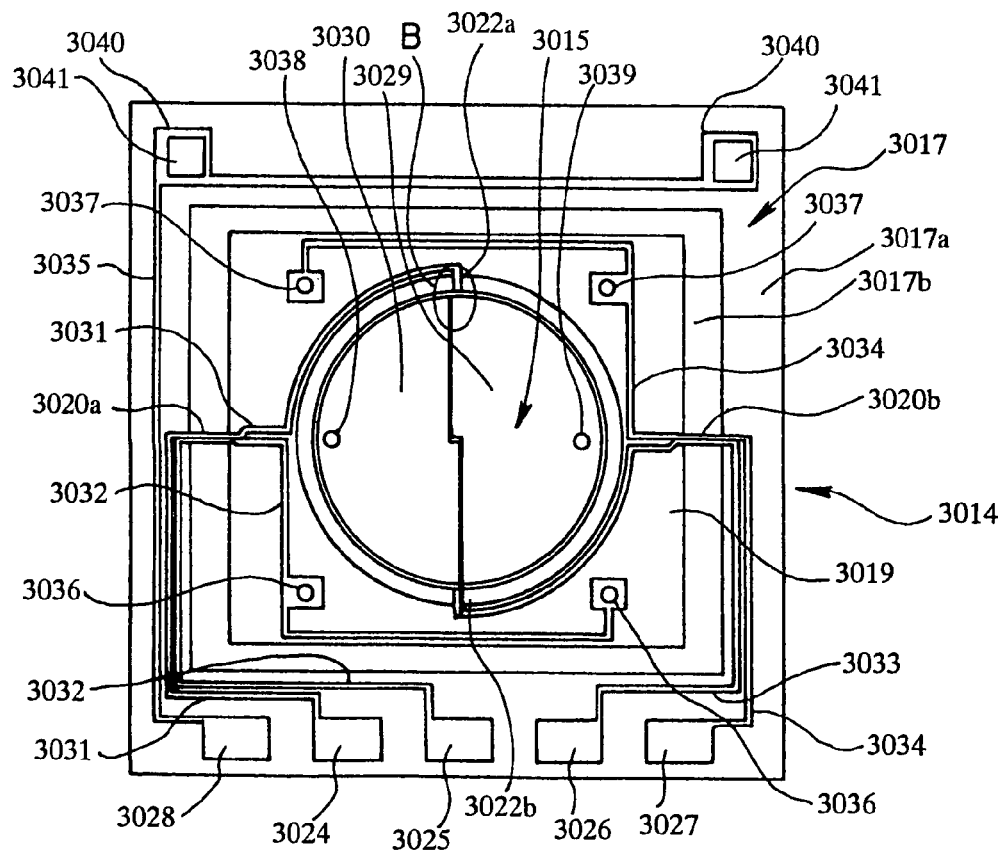

FIGS. 75 to 79 relate to a twenty sixth embodiment of the invention. FIG. 75 is a block diagram showing an entire construction of an optical image capturing apparatus according to the twenty sixth embodiment. FIG. 76 is a section diagram showing a construction of a scan mirror used in the optical image capturing apparatus in FIG. 75. FIG. 77 is a plan view showing a configuration of the scan mirror used in the optical image capturing apparatus in FIG. 75. FIG. 78 is an enlarged diagram showing a construction of a contact portion indicated by an ellipse A in FIG. 77. FIG. 79 is an enlarged diagram showing a construction of a hinge indicated by an ellipse B in FIG. 77.

FIG. 80 is a plan view showing a construction of a scan mirror used in an optical image capturing apparatus according to a twenty seventh embodiment of the invention.

Figure 81:
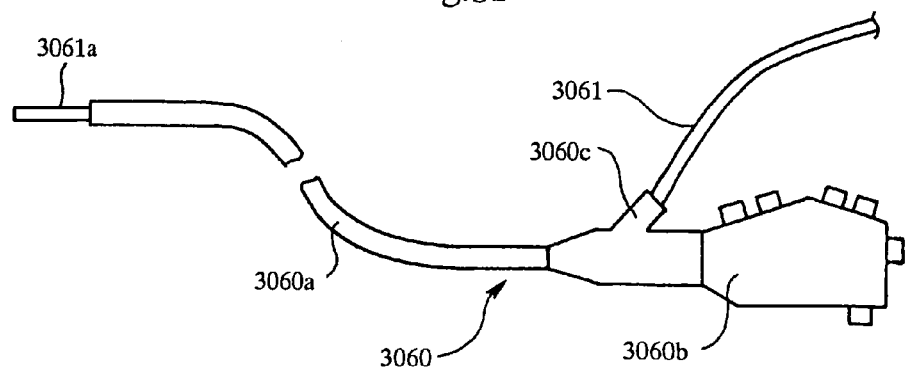

FIG. 81 is an explanatory diagram illustrating a state in which a probe-type optical image capturing apparatus according to the present invention is inserted through a channel of the endoscope.

Figure 82:
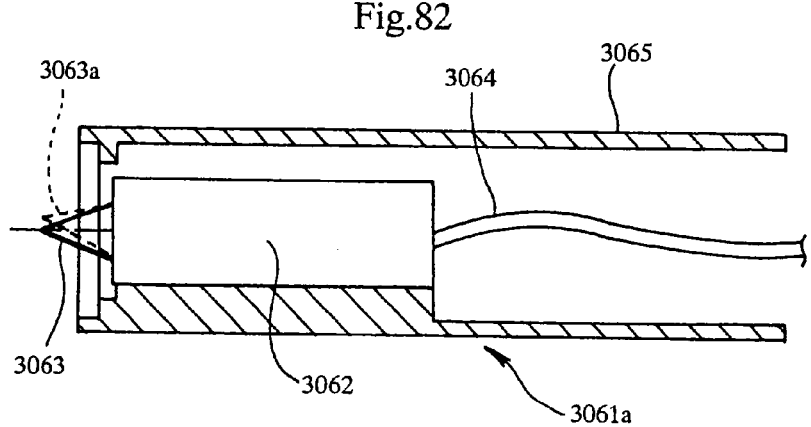
Figure 83:
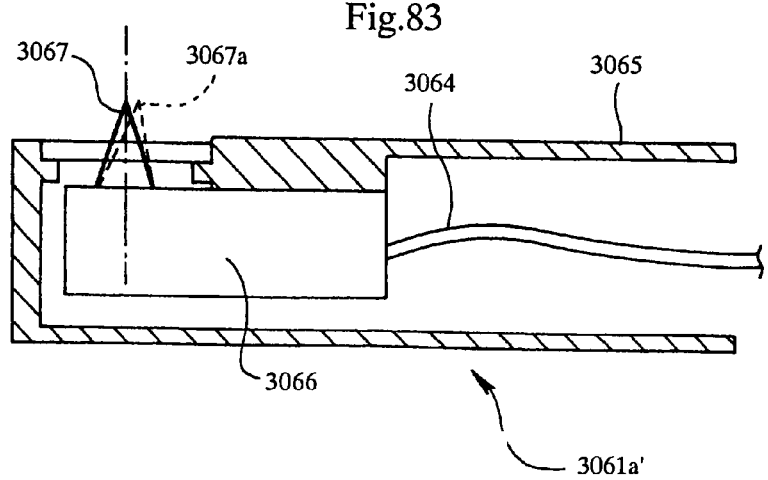

FIG. 82 is a section diagram showing a first construction of a distal end part of the probe-type optical image capturing apparatus according to the invention. FIG. 83 is a section diagram showing a second construction of the distal end part of the probe-type optical image capturing apparatus according to the invention.

Figure 84:
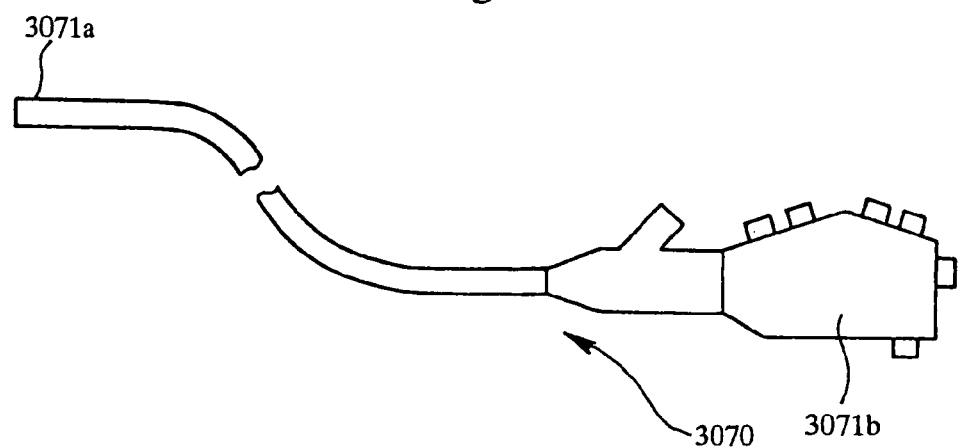

FIG. 84 is a plan view showing an endoscope apparatus of a combination optical image capturing system and endoscope.

Figure 85:
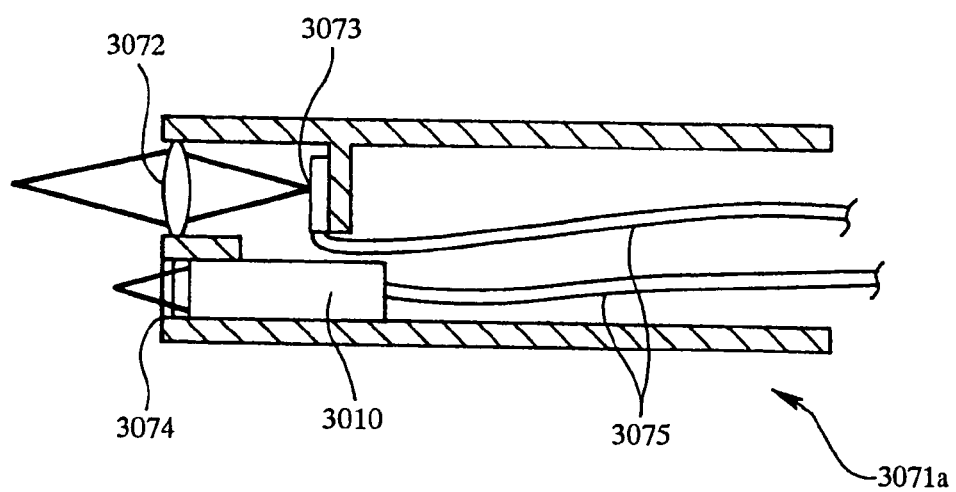

FIG. 85 is a section diagram showing a construction of a distal end of an insert portion of the combination optical image capturing apparatus and endoscope according to the invention.

DETAILED DESCRIPTION OF THE PREFERRED EMBODIMENTS

First Embodiment

Figure 1:
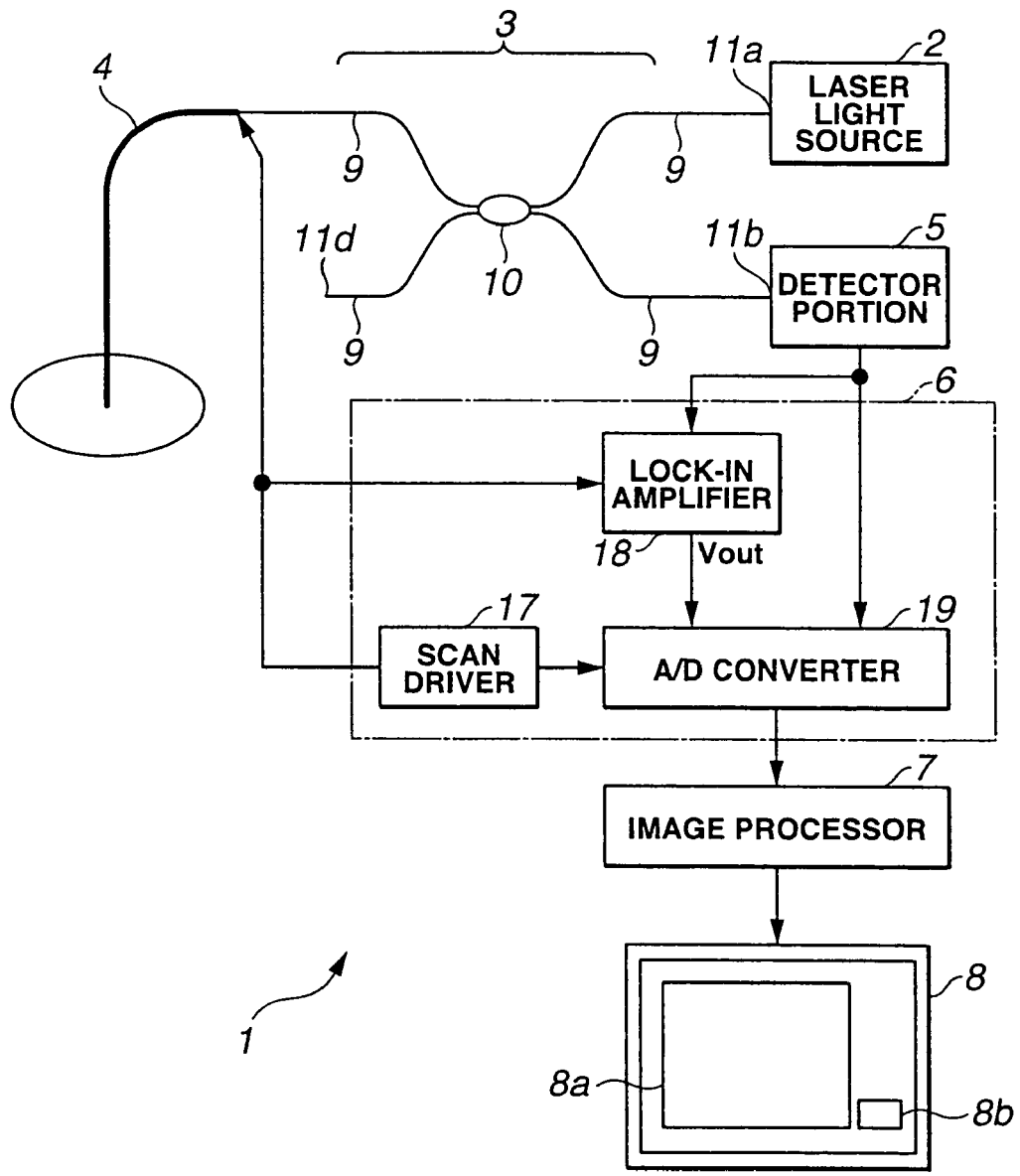

As shown in FIG. 1, an optical image pickup apparatus 1 according to this embodiment includes a laser light source 2, a light transmitter portion 3, an optical scanning probe 4 as an optical scanning portion, a detector portion 5, a control portion 6, an image processor 7 and a monitor 8.

The light transmitter portion 3 includes a four-terminals coupler 10 having a single mode fiber 9 and dividing light bidirectionally. Laser light from the laser light source 2 is launched into one end 11a of four ends of the four-terminals coupler 10. Another end 11c (see FIG. 2) of the four-terminals coupler 10 extends through the optical scanning probe 4. The laser light is transmitted into the inside of the distal end of the optical scanning probe 4. Another end 11d of the ends of the four-terminals coupler 10 is connected to an isolator (not shown), and another end 11b is connected to the detector portion 5.

Figure 2:
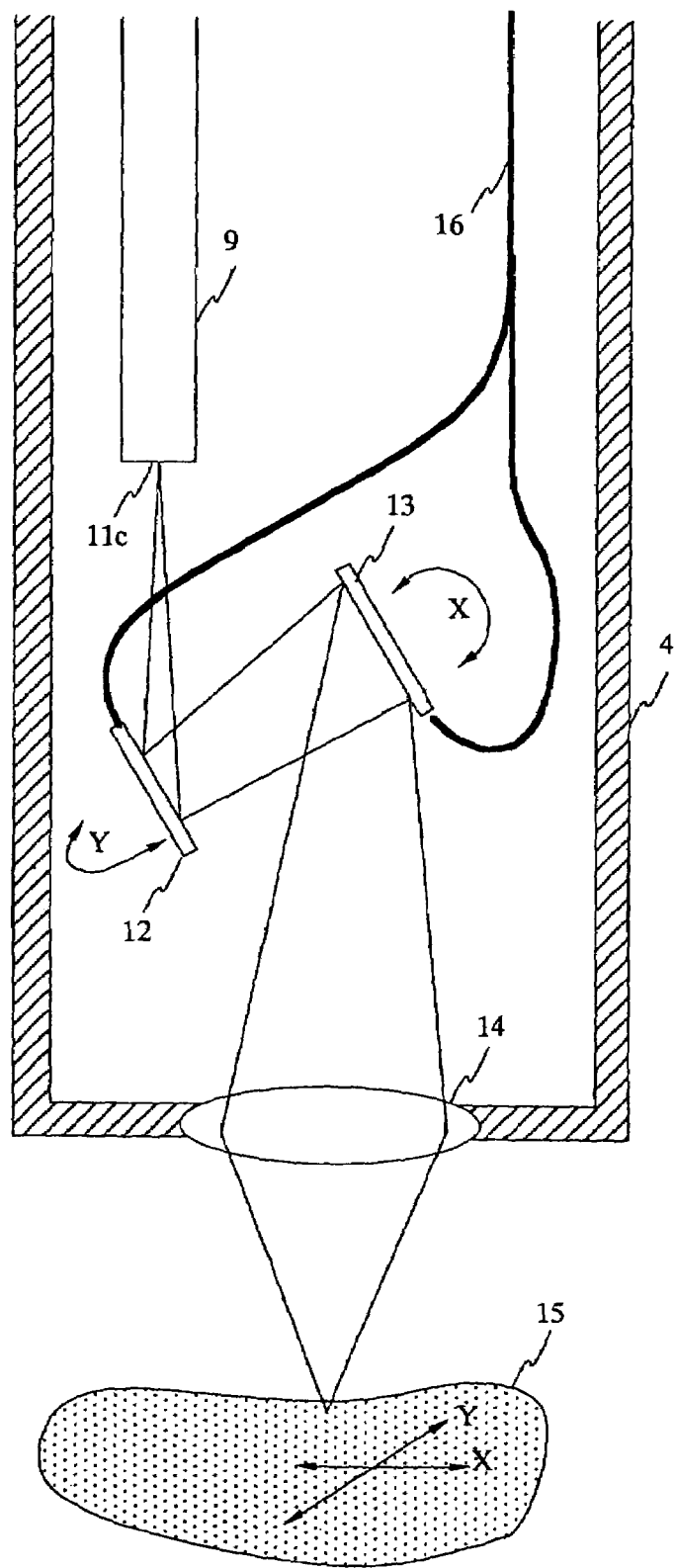

As shown in FIG. 2, the end 11c of the single mode fiber 9 is provided within the distal end of the optical scanning probe 4. Laser light emitted from the end 11c is reflected by a Y-scanning mirror 12 and an X-scanning mirror 13 and is irradiated to a living body tissue 15 through an objective lens 14 at the distal end of the optical scanning probe 4. The Y-scanning mirror 12 and the X-scanning mirror 13 receive predetermined drive signals from the control portion 6 through a signal line 16 so that the Y-scanning mirror 12 and the X-scanning mirror 13 can be pivotably controlled. The rotation of the Y-scanning mirror 12 causes laser light to scan in a Y-direction on the living body tissue 15. The rotation of the X-scanning mirror 13 causes laser light to scan in an X-direction on the living body tissue 15.

The return light from a focal plane of the living body tissue 15 only launches into the end 11c through the objective lens 14, the X-scanning mirror 13 and the Y-scanning mirror 12, is transmitted to the end 11b through the four-terminals coupler 10 shown in FIG. 1 and is detected by the detector portion 5.

In FIG. 1, the control portion 6 includes a scan driver 17, a lock-in amplifier 18 and an A/D converter 19. The scan driver 17 outputs predetermined drive signals to the Y-scanning mirror 12 and the X-scanning mirror 13 and scans the Y-scanning mirror 12 and the X-scanning mirror 13. The lock-in amplifier 18 detects a signal level Vout of a frequency component of the drive signal of the scan driver 17 among signals detected by the detector portion 5. The A/D converter 19 converts signal levels of a signal detected by the detector portion 5 and detected signal of a frequency component of a drive signal detected by the lock-in amplifier 18 to digital signals and outputs the digital signals to the image processor 7.

In the optical image pickup apparatus 1 according to this embodiment with the above-described construction, laser light is transmitted from the laser light source 2 to the end 11c within the distal end of the optical scanning probe 4 through the light transmitter portion 3 and launches into the Y-scanning mirror 12 and the X-scanning mirror 13.

The Y-scanning mirror 12 and the X-scanning mirror 13 are scanned in response to a predetermined drive signal from the scan driver 17. Laser light two-dimensionally scans a focal position of the living body tissue 15 through the objective lens 14. The return light launches into the end 11c through the objective lens 14, the X-scanning mirror 13 and the Y-scanning mirror 12, is transmitted to the end 11b through the four-terminals coupler 10 and is detected by the detector portion 5.

In the control portion 6, the signal detected by the detector portion 5 is sampled by a sampling signal from the scan driver 17 in synchronization with a drive signal for the Y-scanning mirror 12 and the X-scanning mirror 13, is digitized by the A/D converter 19 and is output to the image processor 7. The image processor 7 creates a confocal microscopic image based on the digital signal and displays the confocal microscopic image on an image display area 8a (see FIG. 1) of the monitor 8.

In the control portion 6, the signal detected by the detector portion 5 is input to the lock-in amplifier 18. Since the detected signal has a reflected light component from the surface of the objective lens 14 resulting from scanning of the objective lens 14 by laser light, the detected signal has the same frequency component as that of the drive signal for the Y-scanning mirror 12 and the X-scanning mirror 13. The signal level Vout of the detected signal of the frequency component is detected by the lock-in amplifier 18. The signal level Vout detected by the lock-in amplifier 18 is input to the image processor 7 through the A/D converter 19.

The image processor 7 standardizes and converts the signal level Vout detected by the lock-in amplifier 18 into numbers and displays the result on a level display area 8b (see FIG. 1) of the monitor 8.

By referring to the level value of the level display area 8b, an operator determines that the return light does not have the same frequency component as that of the drive signal and the Y-scanning mirror 12 and the X-scanning mirror 13 are terminated if the level value is equal to or lower than a predetermined value, for example.

In this way, according to this embodiment, since the signal level of the same frequency component as that of the drive signal for the Y-scanning mirror 12 and the X-scanning mirror 13 is detected from the detected signal, the termination of the Y-scanning mirror 12 and the X-scanning mirror 13 can be easily determined. Thus, the emission of laser light from the end of the light scanning probe 4 can be controlled.

The monitor 8 displays the level here, but the invention is not limited thereto. The image processor 7 may compare a predetermined threshold value and a signal level of a detected signal having the same frequency component as that of a drive signal for the Y-scanning mirror 12 and X-scanning mirror 13, and "Normal Scan" or "Scan Stopped" may be displayed as a result thereof.

A signal level having the same frequency component as a drive signal for the Y-scanning mirror 12 and X-scanning mirror 13 may be detected by using a spectrum analyzer instead of the lock-in amplifier.

Second Embodiment

Since a second embodiment is almost the same as the first embodiment, differences therebetween are only described. The same reference numerals are given to the same components, and the descriptions thereof will be omitted.

Figure 3:
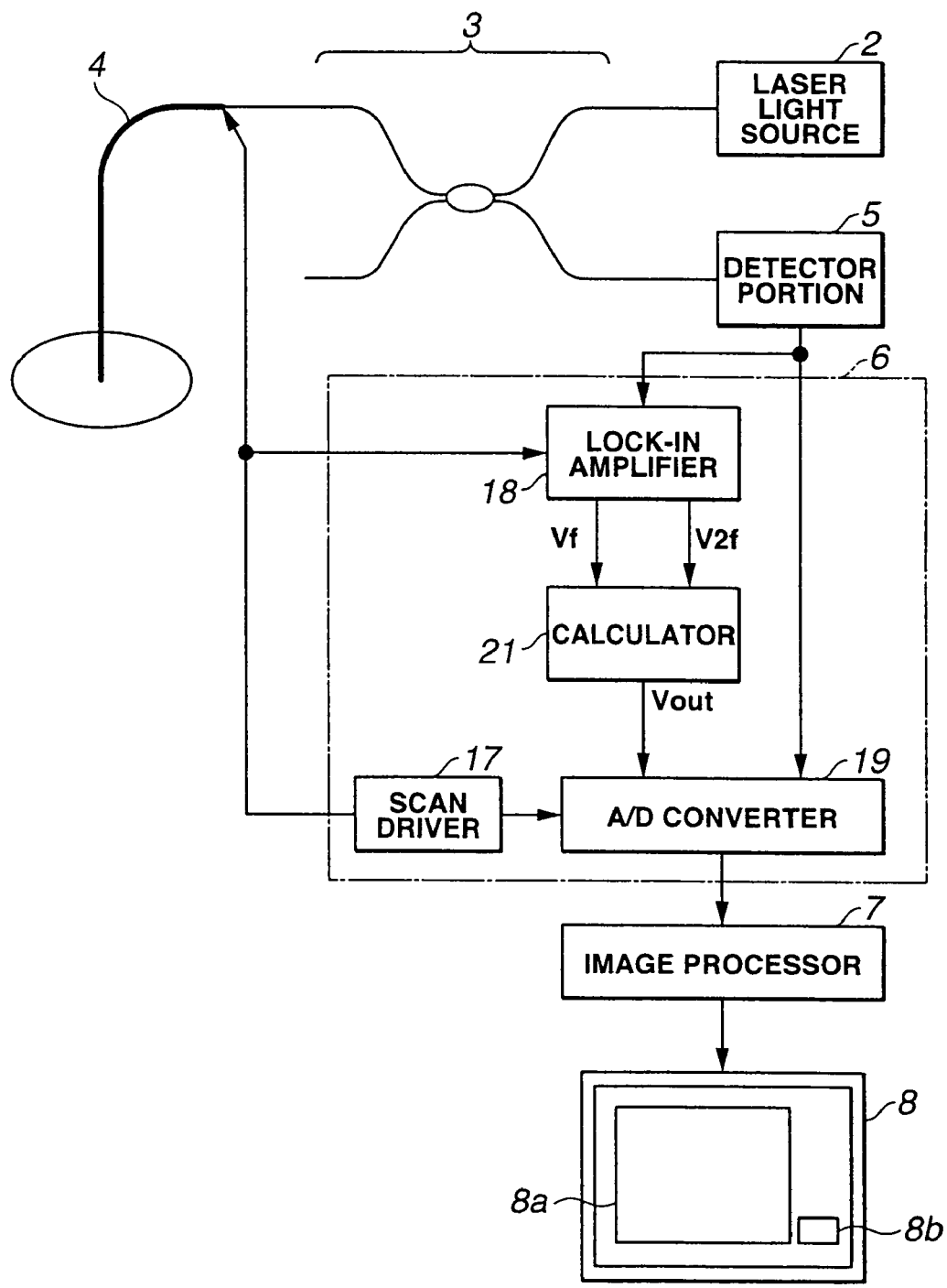
FIG. 3 is a configuration diagram showing a configuration of an optical image pickup apparatus according to a second embodiment of the invention.

According to this embodiment, as shown in FIG. 3, a calculator 21 is provided. A lock-in amplifier 18 detects, from a signal detected by a detector portion 5, a signal level Vf having a same frequency component as that of a drive signal for the Y-scanning mirror 12 and X-scanning mirror 13 and a signal level V2f having a double frequency component of the drive signal for the Y-scanning mirror 12 and X-scanning mirror 13. Then, the calculator 21 performs a calculation, $$V\text{out}=((Vf)^2+(V2f)^2)^{1/2}$$

on the detected signal levels Vf and V2f and outputs the signal level Vout to an A/D converter 19. The other configurations and operations are the same as those of the first embodiment.

According to this embodiment, in addition to the advantages of the first embodiment, signals are output which correspond to a basic wave and a double wave. Therefore, effects due to distortions of a scan driver 17 can be reduced.

Third Embodiment

Since a third embodiment is almost the same as the first embodiment, differences therebetween are only described. The same reference numerals are given to the same components, and the descriptions thereof will be omitted.

Figure 4:
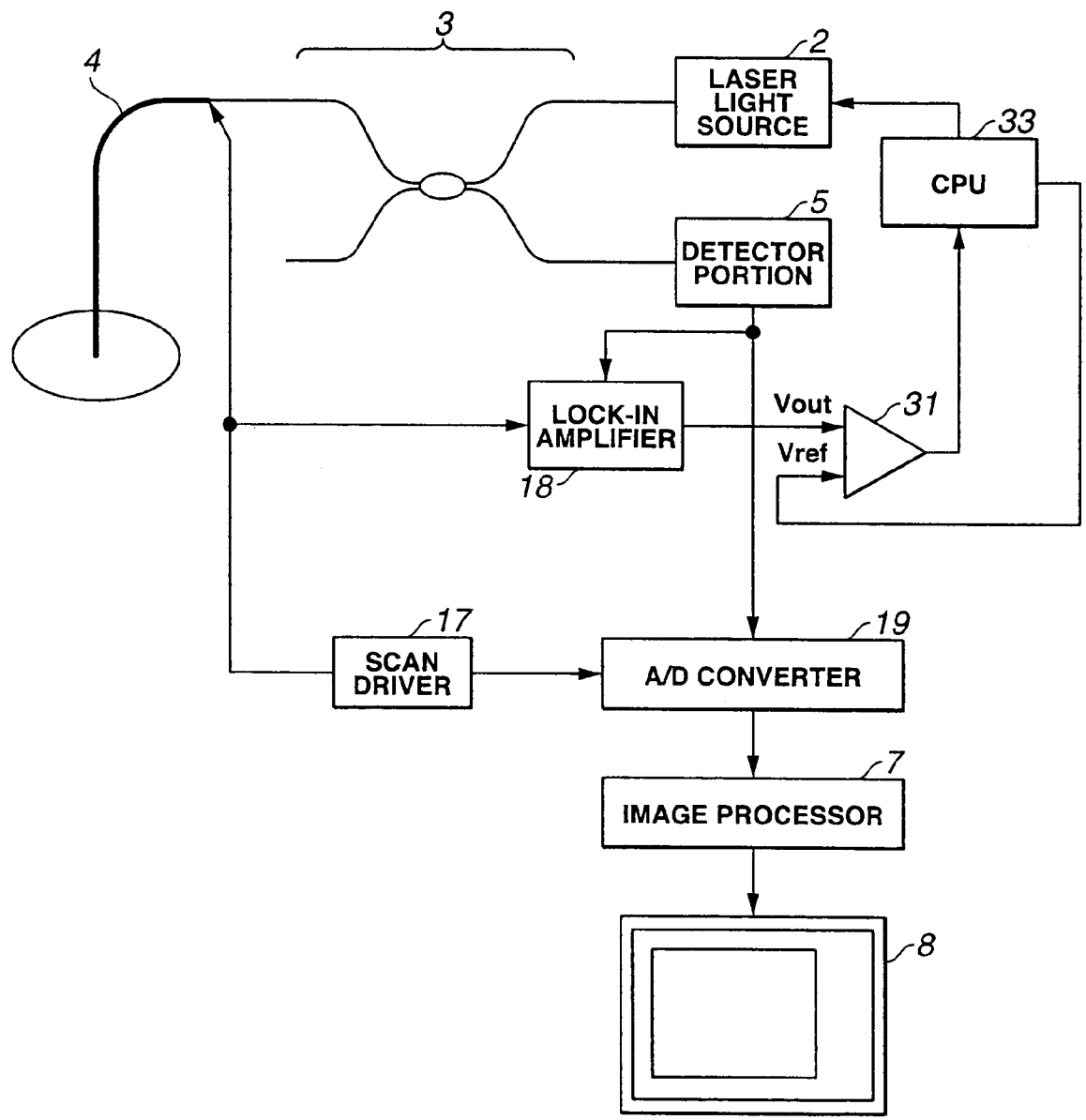
FIG. 4 is a configuration diagram showing a configuration of an optical image pickup apparatus according to a third embodiment of the invention.

According to this embodiment, as shown in FIG. 4, the lock-in amplifier 18 includes a comparator 31 and a CPU 33. The comparator 31 compares a signal level Vout detected by the lock-in amplifier 18 and a predetermined reference voltage Vref. The CPU 33 controls light emission of a laser light source 2 based on an output of the comparator 31. The CPU 33 outputs the reference voltage Vref to the comparator 31. The other configurations and operations are the same as those of the first embodiment.

According to this embodiment, the CPU 33 terminates the light emission of the laser light source 2 when the lock-in amplifier 18 detects a signal level having the same frequency component as that of a drive signal for a Y-scanning mirror 12 and X-scanning mirror 13 and determines that the Y-scanning mirror 12 and X-scanning mirror 13 are terminated as a result of the comparison by the comparator 3. Like the first embodiment, the emission of laser light from the distal end of an optical scanning probe 4 can be controlled, and the deterioration of the laser light source 2 can be prevented.

Fourth Embodiment

Since a fourth embodiment is almost the same as the second embodiment, differences therebetween are only described. The same reference numerals are given to the same components, and the descriptions thereof will be omitted.

Figure 5:
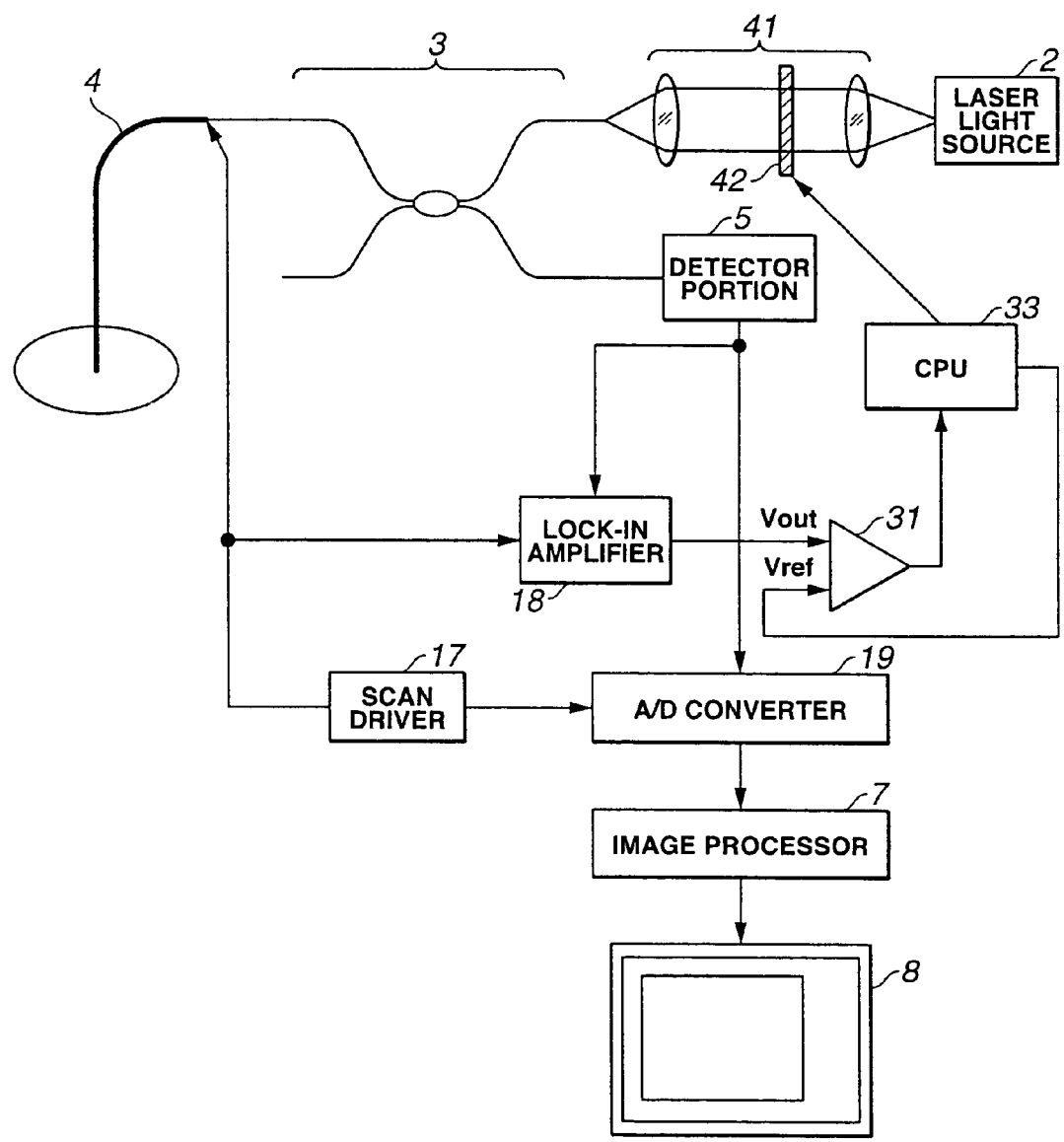
FIG. 5 is a configuration diagram showing a configuration of an optical image pickup apparatus according to a fourth embodiment of the invention.

According to this embodiment, as shown in FIG. 5, a shutter 42 is provided on an optical path 41 from a laser light source 2 to an end 11a of a four-terminals coupler 10. A CPU 33 controls the opening/closing of the shutter 42. The other configurations and operations are the same as those of the third embodiment.

According to this embodiment, the CPU 33 controls the shutter 42 and closes the shutter 42 when the lock-in amplifier 18 detects a signal level having the same frequency component as that of a drive signal for a Y-scanning mirror 12 and X-scanning mirror 13 and determines that the Y-scanning mirror 12 and X-scanning mirror 13 are terminated as a result of the comparison by the comparator 3. Like the third embodiment, the emission of laser light from the distal end of an optical scanning probe 4 can be controlled.

Fifth Embodiment

Since a fifth embodiment is almost the same as the first embodiment, differences therebetween are only described. The same reference numerals are given to the same components, and the descriptions thereof will be omitted.

Figure 6:
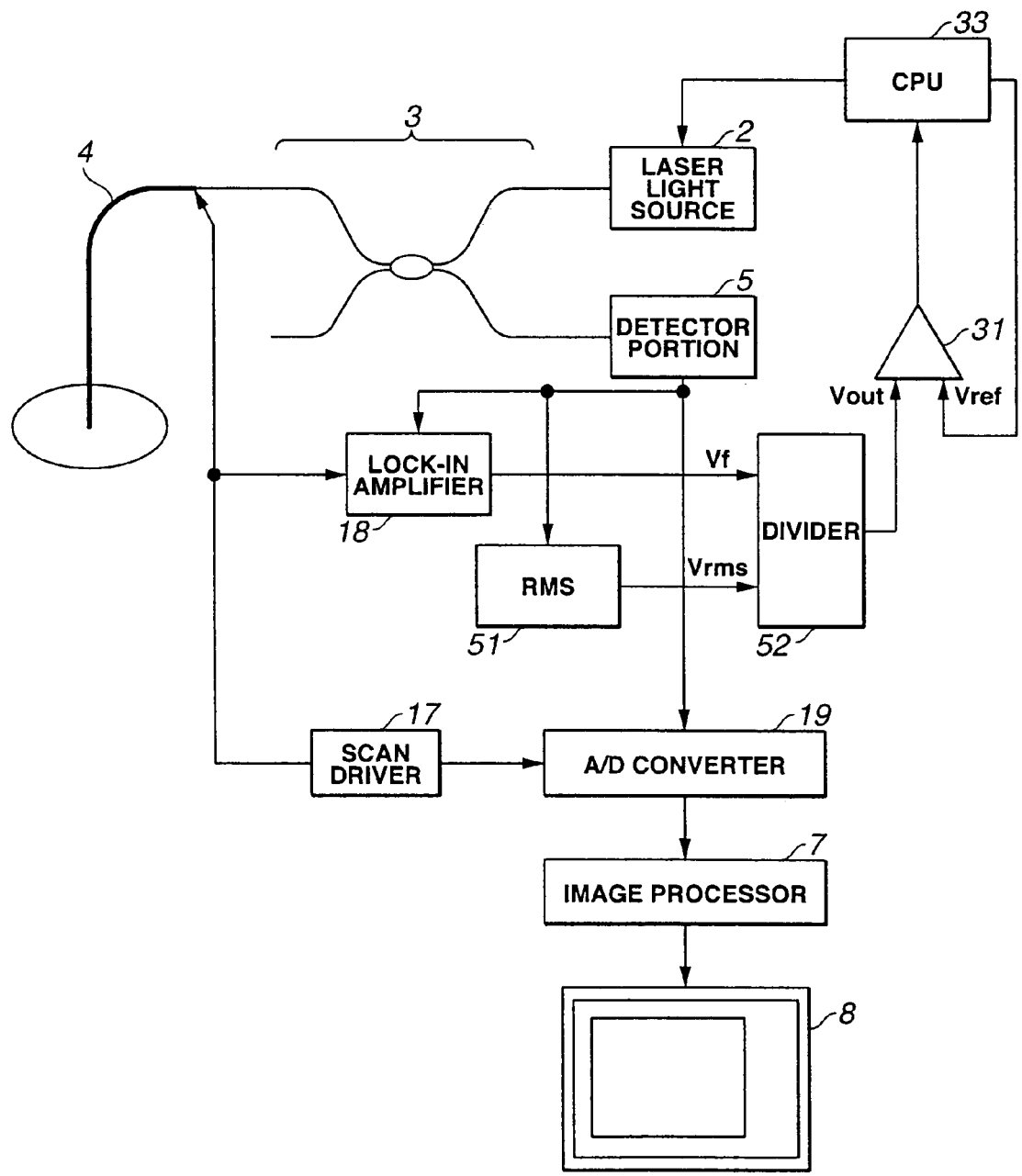
FIG. 6 is a configuration diagram showing a configuration of an optical image pickup apparatus according to a fifth embodiment of the invention.
Figure 7:
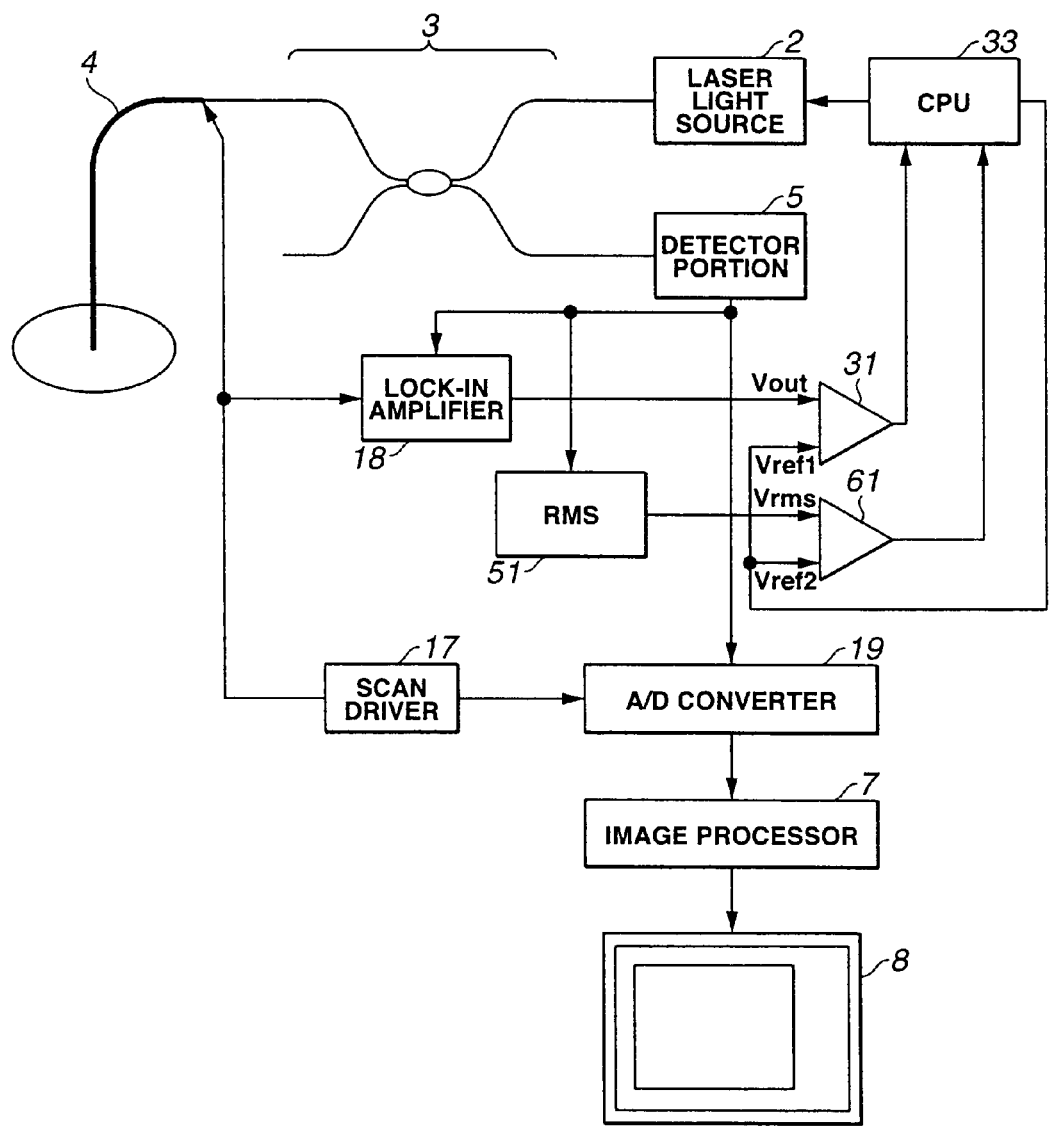
FIG. 7 is a configuration diagram showing a configuration of an optical image pickup apparatus according to a sixth embodiment of the invention.

According to this embodiment, as shown in FIG. 6, an RMS 51 and a divider 52 are provided. The RMS 51 detects a root-mean-square value Vrms of a signal detected by the detector portion 5. The divider 52 divides a signal level Vf having a same frequency component as that of a drive signal from the lock-in amplifier 18 for a Y-scanning mirror 12 and X-scanning mirror 13 by an root-mean-square value Vrms detected by the RMS 51 and outputs the result as a signal level Vout (=Vf/Vrms) to the comparator 31. The other configurations and operations are the same as those of the third embodiment.

According to this embodiment, the divider 52 outputs the value Vout resulting from the division of Vf by Vrms so that a proportion of a size of the component of a scanning frequency to a size of entire signals can be output.

The CPU 33 determines that a Y-scanning mirror 12 and X-scanning mirror 13 are terminated and terminates the light source 2 when Vout<Vref as a result of the comparison by the comparator 31. In other words, when the signal level of the scanning frequency component is smaller than the signal level of the reference voltage, the scanning operation by the mirrors are considered as being terminated.

According to this embodiment, in addition to the advantages of the third embodiment, the operation/termination of the light source can be controlled based on a size of a signal having the scanning frequency component to the size of entire signals. Thus, strength fluctuations (due to strength fluctuations of the light source and/or strength fluctuations of reflected light) of the entire signals do not affect on the control.

Sixth Embodiment

Since a sixth embodiment is almost the same as the fifth embodiment, differences therebetween are only described. The same reference numerals are given to the same components, and the descriptions thereof will be omitted.

A comparator 31 and a second comparator 61 are provided. The comparator 31 compares a signal level Vout of a same frequency component as that of a drive signal from a lock-in amplifier 18 for a Y-scanning mirror 12 and X-scanning mirror 13 and a reference voltage Vref1. The second comparator 61 compares a root-mean-square value Vrms detected by an RMS 51 and a second reference voltage Vref2. The other configurations and operations are the same as those of the fifth embodiment.

According to this embodiment, the CPU 33 determines that the Y-scanning mirror 12 and the X-scanning mirror 13 are terminated when Vout<Vref1 and Vrms>Vref2 and terminates a light source. In other words, "when the scanning frequency component is small though the strength of entire signals is high to some extent", the scanning operation of the mirrors is considered as being terminated.

According to this embodiment, in addition to the advantages of the third embodiment, the light source is not terminated unnecessarily since Vrms>Vref2 is achieved only during observation by a confocal microscope so that the mirror detection cannot be performed (that is, the mirror is considered as being terminated) when a scanning operation by the mirror does not have to be checked (when an observation is not performed).

Seventh Embodiment

Since a seventh embodiment is almost the same as the third embodiment, differences therebetween are only described.

The same reference numerals are given to the same components, and the descriptions thereof will be omitted.

According to this embodiment, as shown in FIG. 8, a lock-in amplifier 18 detects a signal level V2f of a double frequency component of that of a drive signal for a Y-scanning mirror 12 and X-scanning mirror 13 from a signal detected by a detector portion 5 and outputs the signal level V2f to a CPU 33.

As shown in FIGS. 9 and 10, a reflector 71 is provided in the vicinity of the rim of an objective lens 14 within the distal end of an optical scanning probe 4. The reflector 71 contains a circular-ring-shaped scattering material or fluorescent material symmetrical to an optical axis. The other configuration is the same as the third embodiment.

As shown in FIG. 11, if V2f is detected at a step S1, the CPU 33 judges whether V2f is smaller than a reference value Vref2 at a step S2. Light reflected from the ring-shaped reflector 71 in the vicinity of the rim of the objective lens 14 within the distal end is reflected light having a double frequency of a drive frequency while the Y-scanning mirror 12 and X-scanning mirror 13 are normally scanning. Thus, if V2f is equal to or larger than the reference value Vref2 (FIG. 12) at a step S3, the scanning is determined as being performed with a normal amplitude. Then, the processing returns to the step S1. If V2f is smaller than the reference value Vref2 (FIG. 13), the scanning is not performed with a desired amplitude. Thus, the scanning by the mirrors is determined as being terminated at a step S4, and the light source is terminated at a step S5.

According to this embodiment, not only the same advantages as those of the third embodiment can be obtained but also a signal having a frequency corresponding to a drive frequency can be detected when the reflector 71 is provided outside of an observation area by the scan mirrors and while the mirrors are performing a scanning operation normally. Thus, when light reflected from the lens surface is weak and a scanning frequency component of the mirrors cannot be detected easily, the scanning operation by the mirrors can be detected by detecting return light from the reflector 71. Furthermore, since the reflector 71 is provided outside of the area to be observed by the scan mirrors, the observation of a subject is not prevented.

As shown in FIGS. 14 and 15, the reflector 71 may be evaporated onto a place around the rim of the objective lens 14. In this case, an additional part is not necessary for the probe assembly.

Eighth Embodiment

Since an eighth embodiment is almost the same as the seventh embodiment, differences therebetween are only described. The same reference numerals are given to the same components, and the descriptions thereof will be omitted.

According to this embodiment, as shown in FIGS. 16 and 17, a reflector 71 is provided in the vicinity of the rim of an objective lens 14 within the distal end of an optical scanning probe 4. The reflector 71 contains an oval-ring-shaped scattering material or fluorescent material asymmetrical to an optical axis. As shown in the drawings, a positional relationship between the optical axis and the reflector 71 is R1<R2 where R1 is a distance between one end of the reflector 71 and the optical axis and R2 is a distance between the other end of the reflector 71 and the optical axis and the distances R1 and R2 differ from each other.

According to this embodiment, a lock-in amplifier 18 detects, from a signal detected by the detector portion 5, a signal level Vf having a frequency component of a drive signal for a Y-scanning mirror 12 and X-scanning mirror 13 and a signal level V2f having the double frequency component and outputs the signal levels Vf and V2f to the CPU 33. The other configurations are the same as that of the seventh embodiment.

As shown in FIG. 18, if V2f is detected at a step S11, the CPU 33 judges at a step S12 whether V2f is smaller than a reference value Vref2 or not. When the Y-scanning mirror 12 and X-scanning mirror 13 scan normally, reflected light from the ring-shaped reflector 71 in the vicinity of the rim of the objective lens 14 within the distal ends scans with the scan range (amplitude) of 2×R2. The reflected light has the double frequency of a drive frequency. Thus, if V2f is equal to or larger than the reference value Vref2 (FIG. 19) at a step S13, the scanning is determined as being performed with a normal amplitude. Then, the processing returns to the step S11. If V2f is smaller than the reference value Vref2 (FIG. 20 or 21), the scanning is not performed at a normal amplitude. Therefore, Vf is detected at a step S14, and it is determined whether Vf is smaller than a reference value Vref2 at a step S15.

If it is determined that Vf is equal to or larger than the reference value Vref2 (FIG. 20), it is determined that the scanning is performed with a narrower amplitude range (abnormality in motion angle) at a step S16. The scan frequency is adjusted at a step S17, and the processing returns to the step S11. By adjusting the scan frequency, a displacement of the resonant frequency due to a temperature and the like is corrected. Thus, the scanning is automatically adjusted to scanning with the normal amplitude.

If it is determined that Vf is smaller than the reference value Vref2 (FIG. 21), it is determined at a step S18 that the scanning by the mirrors is terminated. Then, at a step S19, the light source is terminated.

According to this embodiment, in addition to the advantages of the seventh embodiment, the automatic adjustment to the scanning with a normal amplitude can be performed.

Ninth Embodiment

Since a ninth embodiment is almost the same as the third embodiment, differences therebetween are only described. The same reference numerals are given to the same components, and the descriptions thereof will be omitted.

According to this embodiment, as shown in FIG. 22, in addition to a laser light source 2, a light transmitter portion 3 and a detector portion 5, which are included in a confocal optical system for an optical scanning probe 4 as an optical scanning portion, a laser light source 2a, light transmitter portion 3a, and detector portion 5a, which are included in an optical system for detecting scanning by mirrors, are provided. As shown in FIG. 23, one end of a single mode fiber 9a included in the light transmitter portion 3a is disposed at the distal end of the optical scanning probe 4. For example, a scatterer 101 is provided on the back of an X-scanning mirror 13.

Like the confocal optical system, laser light from the laser light source 2a is reflected by the scatterer 101 in the optical system for detecting the scanning by the mirrors. The reflected light is detected by the detector portion 5a, and the CPU 33 controls the laser light source 2 based on the detection result by the detector portion 5a.

The positions of the single mode fiber 9a and scatterer 101 are adjusted such that the strength of reflected light from the scatterer 101 can be maximum (point B in FIG. 25) when the X-scanning mirror 13 is at a neutral position (point A in FIG. 24).

Also according to this embodiment, the same advantages can be obtained as those of the third embodiment.

As shown in FIG. 26, a distal end processed lens 102 may be provided at an emission end of the single mode fiber 9a at the distal end of the optical scanning probe 4. By providing the distal end processing lens 102, return light from the scatterer 101 provided at the back surface of the X-scanning mirror 13 can be efficiently gathered.

Tenth Embodiment

Since a tenth embodiment is almost the same as the third embodiment, differences therebetween are only described. The same reference numerals are given to the same components, and the descriptions thereof will be omitted.

According to this embodiment, as shown in FIG. 27, laser light emitted from a single mode fiber 9 at the distal end of an optical scanning probe 4 is transmitted to an XY scan mirror 112 through a fixed mirror 111. Then, the laser light is two-dimensionally scanned on an XY surface by the XY scan mirror 112 and is irradiated to a living body tissue 15 through an objective lens 14. As shown in FIG. 28, the XY scan mirror 112 is held by four hinge portions 113. A photodetector 114 for detecting light is provided on the back surface of the XY scan mirror 112. An emitting end face of a fiber 115, which is different from the single mode fiber 9, is disposed at a position opposed to the photodetector 114 (see FIG. 27).

According to this embodiment, as shown in FIG. 29, a laser light source 2b is provided for supplying laser light to the fiber 115. A lock-in amplifier 18 extracts a signal Vfx having an X-scan component and signal Vfy having a Y-scan component in the XY scan mirror 112 from a detected signal from the photodetector portion 114. More specifically, detected signals from the photodetector portion 114 are signals including X-scan and Y-scan components as shown in FIG. 30. The lock-in amplifier 18 extracts a signal having the X-scan component as shown in FIG. 31 and a level signal corresponding to a signal having the Y-scan component as shown in FIG. 32 from these detected signals.

The signals Vfx and Vfy extracted by the lock-in amplifier 18 are compared with reference values Vrefx and Vrefy by comparators 116 and 117, and the comparison result is output to the CPU 33.

As shown in FIG. 33, if Vfx and Vfy are detected at a step S21, the reference values Vrefx and Vrefy are compared by the comparators 116 and 117. The CPU 33 determines Vfx<Vrefx or Vfy<Vrefy at a step S22 and, if No, determines that the scanning is being performed with a normal amplitude at a step S23. Then, the processing returns to the step S21. If Yes, the scanning is not performed with a desired amplitude. Thus, it is determined at a step S24 that the scanning by the mirrors is terminated. At a step S25, the light source is terminated.

Thus, also according to this embodiment, the same advantages can be obtained as those of the third embodiment.

Eleventh Embodiment

Since an eleventh embodiment is almost the same as the tenth embodiment, differences therebetween are only described. The same reference numerals are given to the same components, and the descriptions thereof will be omitted.

According to this embodiment, as shown in FIG. 34, a fixed mirror 121 instead on the photodetector 114 is provided on the back surface of an XY scan mirror 112. Laser light irradiated from an emission end face of a fiber 115 is detected by a light detector 122. As shown in FIG. 35, the photodetector 122 includes four-part split light detecting element. Add/subtract signals of elements including add/subtract signals (A+B)−(C+D) and (A+C)−(B+D) are output to a lock-in amplifier 18 where output signals of shown elements A, B, C and D are A, B, C and D.

As shown in FIG. 36, the lock-in amplifier 18 extracts a signal level Vfx of an X-scan component (see FIG. 37) at a mirror scanning frequency of the XY scan mirror 112 from (A+B)−(C+D). The lock-in amplifier 18 further extracts a signal level Vfy of a Y-scan component (see FIG. 38) at the mirror scanning frequency of the XY scan mirror 112 from (A+C)−(B+D).

According to this embodiment having the above-described construction, the same advantages can be obtained from the same operation (see the flowchart in FIG. 33) as that of the tenth embodiment.

Furthermore, according to this embodiment, processing as shown in FIG. 39 can be performed. More specifically, when Vfx and Vfy are detected at a step S31, the comparators 116 and 117 compare the Vfx and Vfy with reference values Vrefx and Vrefy. The CPU 33 judges Vfx<Vrefx1 or Vfy<Vrefy1 at a step S32. If No, it is determined at a step S33 that the scanning is performed with a normal amplitude. Then, the processing returns to the step S21.

If Yes, the scanning is not performed at a desired amplitude, it is determined at a step S34 that Vfx<Vrefx2 (Vrefx1>Vrefx2) or Vfy<Vrefy2 (Vrefy1>Vrefy2). If No, it is determined at a step S35 that the scanning is performed without the normal amplitude. Therefore, it is determined at a step S36 that the scanning is performed with a narrower amplitude range (abnormality in motion angle). At a step S37, the scan frequency is adjusted, and the processing returns to the step S31. By adjusting the scan frequency, a displacement of the resonant frequency due to a temperature and the like, for example, is corrected. Thus, the scanning is automatically adjusted to scanning with the normal amplitude.

If Vfx<Vrefx2 (Vrefx1>Vrefx2) or Vfy<Vrefy2 (Vrefy1>Vrefy2), it is determined at a step S38 that the scanning by the mirrors are terminated. At a step S39, the light source is terminated.

Twelfth Embodiment

Since a twelfth embodiment is almost the same as the third embodiment, differences therebetween are only described. The same reference numerals are given to the same components, and the descriptions thereof will be omitted.

As shown in FIG. 40, according to this embodiment, a light source 201, a half mirror 202 and a dichroic mirror 204 are provided. The light source 201 generates exciting light with a wavelength $\lambda e$ for exciting fluorescence to a living body tissue 15. The half mirror 202 allows the exciting light to pass through. The dichroic mirror 204 guides exciting light through the half mirror 202 to an end face of incident of a fiber 203 for guiding light to the distal end of an optical scanning probe 4.

Then, the exciting light is scanned within the distal end of the optical scanning probe 4 and is irradiated to the living body tissue 15. The return light is launched into the fiber 203 again and is guided to the dichroic mirror 204. The return light from the living body tissue 15 contains fluorescence with a wavelength $\lambda f$ and return exciting light with a wavelength $\lambda e$. The fluorescence with the wavelength $\lambda f$ passes through dichroic mirror 204 and is detected by a detector portion 6. A confocal image is created in accordance with a signal detected by the detector portion 6.

On the other hand, the return exciting light with the wavelength $\lambda e$ does not pass through the dichroic mirror 204. The return exciting light is guided to the half mirror 202, is reflected by the half mirror 202 and is detected by a detector portion 206, which is different from the detector portion 6. A signal detected by the detector portion 206 is output to the lock-in amplifier 18, and a signal level Vout of a scan frequency component is extracted in the lock-in amplifier 18. The other configurations and operations are the same as those of the third embodiment.

Thus, also according to this embodiment, the same advantages as those of the third embodiment can be obtained. Furthermore, according to this embodiment, scanning operations can be detected more accurately since different detectors are provided for detecting light to be used for imaging and light to be used for detecting scanning operations.

Thirteenth Embodiment

Since a thirteenth embodiment is almost the same as the twelfth embodiment, differences therebetween are only described. The same reference numerals are given to the same components, and the descriptions thereof will be omitted.

According to this embodiment, as shown in FIG. 41, exciting light with a wavelength $\lambda e$ from a light source 201 is directly guided to a dichroic mirror 204 and is launched into an end face of incident of a fiber 203 by the dichroic mirror 204.

As shown in FIG. 42, a fluorescent material 211 generating fluorescence with a wavelength $\lambda 1$ for exciting light with a wavelength $\lambda e$ is coated on the outer ring of the internal surface of an objective lens 14. As a result, return light to the fiber 203 includes fluorescence with a wavelength $\lambda f$ from the living body tissue 15 and fluorescence with a wavelength $\lambda 1$ from the fluorescence material 211.

The dichroic mirror 204 selectively allows these wavelengths $\lambda f$ and $\lambda 1$ to pass through. The fluorescence with the wavelengths $\lambda f$ and $\lambda 1$ having passed through the dichroic mirror 204 is guided to the dichroic mirror 212, as shown in FIG. 41. The dichroic mirror 212 separates the fluorescence with the wavelength $\lambda f$ and the fluorescence with the wavelength $\lambda 1$ and emits the fluorescence with the wavelength $\lambda f$ to the detector portion 6 and the fluorescence with the wavelength $\lambda 1$ to the detector portion 206. The other configurations and operations are the same as those of the twelfth embodiment.

According to this embodiment, scanning operations by the mirrors are detected by using fluorescence with the wavelength $\lambda 1$ from the fluorescent material 211 on the surface of the objective lens 14. Then, the fluorescence with the wavelength $\lambda f$ from the living body tissue 15 is used for imaging.

According to this embodiment, in addition to the advantages of the twelfth embodiment, the misdetection due to noise light in reflected light and/or scattering light (such as stray light in an optical system in the middle) independent from the scanning operations by the mirrors can be prevented since fluorescence is also used for detection of scanning operations.

Fourteenth Embodiment

Since a fourteenth embodiment is almost the same as the thirteenth embodiment, differences therebetween are only described. The same reference numerals are given to the same components, and the descriptions thereof will be omitted.

According to this embodiment, as shown in FIG. 43, a light source 201 generates exciting light with a wavelength $\lambda e1$ and exciting light with a wavelength $\lambda e2$. The exciting light with the wavelength $\lambda e1$ excites fluorescence with a wavelength $\lambda f$ from the living body tissue 15. The exciting light with the wavelength $\lambda e2$ excites fluorescence with a wavelength $\lambda 1$ from a fluorescent material 211. The other configurations and operations are the same as those of the thirteenth embodiment.

According to this embodiment, the wavelengths of exciting light to a subject and exciting light to a fluorescent material are differentiated so that the difference between $\lambda f$ and $\lambda 1$ can be compared and be controlled freely (the difference can be increased). Thus, in addition to the advantages of the thirteenth embodiments, the separation precision of light of the wavelengths can be improved, and the detection power for scanning operations can be improved.

The first to fourteenth embodiments can be used together with an endoscope apparatus 304 including an electronic endoscope 301, an endoscopic light source device 302 and a video processor 303 and so on as shown in FIG. 44. With an optical scanning probe 4 inserted within a forceps insert channel of the electronic endoscope 301, an endoscopic image and a confocal image can be displayed on a monitor 305.

Fifteenth Embodiment

When a probe is inserted into a body cavity, the states of the inside and surrounding of the probe cannot be viewed. Even when optical scanning means fails for some reason or even when an abnormality occurs in a resulting image due to the decreased scan width, for example, it is significantly difficult for an operator to judge whether the cause is the failure of the optical scanning means, the cause is the falling out of focus due to a change in distance between the probe and an subject, or the cause is a failure in the probe itself.

In other words, while an abnormality occurs in an image due to the failure in the optical scanning means, the operator may misunderstand that the cause is the falling out of focus. Then, by further continuing the observation, the operator may misinterpret the resulting image. This may cause the wastes of the observation time and/or life of laser.

Therefore, like this embodiment, which will be described below, the introduction of means for detecting an operational condition of the optical scanning means into a probe-type optical image pickup apparatus is significantly meaningful.

As shown in FIG. 45, an optical image pickup apparatus 1001 according to this embodiment includes an optical scanning probe 1002, a confocal observation apparatus 1003 and a personal computer 1005. The optical scanning probe 1002 irradiates laser light to a living body tissue by performing optical scanning two-dimensionally. The optical scanning probe 1002 is removably connected to the confocal observation apparatus 1003 through a connector 1006. The confocal observation apparatus 1003 irradiates laser light to the optical scanning probe 1002 and detects a confocal optical image. The personal computer 1005 controls the confocal observation apparatus 1003 and displays a confocal image on the monitor 1004.

The personal computer 1005 includes an HD 1051, an I/O portion 1052, an A/D portion 1053 and a CPU 1054. The HD 1051 stores an OS and an image processing software. The I/O portion 1052 exchanges control signals and image signals with the confocal observation apparatus 1003 and the monitor 1004. The A/D portion 1053 converts signals of a confocal optical image, which are detected by the confocal observation apparatus 1003 to digital signals. The CPU 1054 controls these components.

The confocal observation apparatus 1003 includes a laser light source 1031, a laser driver 1032, a light transmitter portion 1035, a driver 1036, a connection detecting portion 1037, a driving condition setting circuit 1038, a table memory 1039, a control circuit 1040, and a photodetector 1041. The laser light source 1031 supplies laser light to the optical scanning probe 1002. The laser driver 1032 drives the laser light source 1031. The light transmitter portion 1035 includes a single mode fiber 1033 for transmitting laser light from the light source 1031 and a four-terminals coupler 1034 for dividing light bidirectionally. The driver 1036 drives a two-dimensional scanning mirror provided within a probe distal end portion 1002a of the optical scanning probe 1002 for two-dimensionally scanning laser light, as described later. The connection detecting portion 1037 detects a connection state of the optical scanning probe 1002 to the connector 1006. The driving condition setting circuit 1038 sets a driving condition of the driver 1036, for example, in response to a control signal from the personal computer 1005. The table memory 1039 stores data for the driving condition setting circuit 1038 to read drive waveform data of the driver 1036 based on a driving condition. The control circuit 1040 controls the laser driver 1032. The photodetector 1041 detects return light from the optical scanning probe 1002 and outputs the result to the A/D portion 1053.

The driving condition setting circuit 1038, the table memory 1039 and the control circuit 1040 may be an FPGA 1042. Here, instead of an FPGA, an ASIC or other combinations of general ICs may be used as far as the driving condition setting circuit 1038, the table memory 1039 and the control circuit 1040 can be achieved.

The control circuit 1040 is a NOR circuit for activating a light source output control signal LC and allowing outputs of the laser driver 1032 only when a light source output permitting signal LE from the personal computer 5, a drive waveform output permitting signal OE from the driving condition setting circuit 1038, a scanning state signal SS indicating a scanning state of a two-dimensional scanning mirror from the probe distal end portion 1002a and a connection detection signal CC detected by the connection detecting portion 1037 are all "0" (valid).

While the validity is determined when the light source output permitting signal LE, the drive waveform output permitting signal OE, a scanning state signal SS and the connection detection signal CC are all "0", a digital circuit may be adopted which determines the validity at "1".

The laser driver 1032 electrically controls such that laser can be turned on at "1" and be turned off at "0" by using a relay circuit, for example, (not shown) in accordance with a state of the light source output control circuit LC. While the laser is turned on when the light source output control circuit LC is "1" here, laser may be turned on at "0".

The drive waveform output permitting signal OE is "0" (Valid) when the setting of parameters and waveform data of the driving condition setting circuit 1038 of the confocal observation apparatus 3 has completed.

The light source output permitting signal LE is controlled by image processing software to be "0" (valid) immediately after the laser driver 1032 starts outputting a drive waveform and the amplitude becomes maximum.

As shown in FIG. 46, a fixed mirror 1020, a two-dimensional scanning mirror 1021 and an objective lens 1022 are provided within the probe distal end portion 1002a. Light passing through the single-mode fiber 1033 and reflected by the fixed mirror 1020 and the two-dimensional scanning mirror 1021 is two-dimensionally scanned by a two-axial hinge 1023, which is shown in FIG. 47, in the two-dimensional scanning mirror 1021.

A scanning state signal SS is obtained as follows. As shown in FIG. 48, light is irradiated by another light source (LED or plane light emitting laser) 1024 from the back surface side of a mirror surface 1029 of the two-dimensional scanning mirror 1021. The reflected light from the back surface of the two-dimensional scanning mirror 1021 is detected by a two-part split photodetector (two-part split array form PD) 1025.

Here, light hits the two-part split photodetector 1025 only when the two-dimensional scanning mirror 1021 is moved by a predetermined angle. A scan width can be calculated by detecting the left end and right end of the two-part split photodetector 1025 in FIG. 48. The light is received by the two-part split photodetector 1025, and electric signals output by the two-part split photodetector 1025 are detected by an electric circuit (not shown). Since the light detected by the two-part split photodetector 1025 passes through the other light source periodically, electric signals output by the two-part split photodetector 1025 include a scan frequency component of the two-dimensional scanning mirror 1021. The scan frequency component can be detected by Fourier conversion, for example. The scan width and scan frequency are compared with respective predetermined values in a comparator, for example (not shown). If the scan width and scan frequency are equal to or lower than the predetermined values, "0" is output as a scanning state signal SS. If the scan width and scan frequency are higher than the predetermined values, "1" is output as a scanning state signal SS.

Instead of the light source (LED or plane light emitting laser) 1024, a hole for guiding light may be provided in the two-dimensional scanning mirror 1021 and a scanning state may be detected thereby. Thus, laser light from the light source (laser light source 1031) for scanning can be detected by the two-part split photodetector 1025.

Alternatively, as shown in FIG. 49, due to the inclination caused by the driving of the two-dimensional scanning mirror 1021, an electrostatic capacity between the back surface of the two-dimensional scanning mirror 1021 and the GND decreases as the distance therebetween increases. On the other hand, an electrostatic capacity between the back surface of the two-dimensional scanning mirror 1021 and the GND increases as the distance therebetween decreases. By detecting the varying electrostatic capacity by using this fact and detecting the amplitude and frequency as a scan width and scan frequency, respectively, the scanning state may be detected.

One pin of the connector 1005 of the optical scanning probe 1002 is grounded through a resister, and the optical scanning probe 1002 is connected with the confocal observation apparatus 1003 so as to be switched by a switching transistor within the confocal observation apparatus 3. If the optical scanning probe 1002 is connected to the confocal observation apparatus 1003, the connection detection signal CC is "0" (valid). If not connected or if out of connection, the connection detection signal CC is "1" (invalid).

The switching transistor is shown in FIG. 45 while the invention is not limited thereto. Any switching device may be used.

FIG. 50 shows a timing chart of light source output control signals LC for a light source output permitting signal LE, drive waveform output permitting signal OE, scanning state signal SS and connection detection signal CC when the driving of the scanner of the probe distal end portion 1002a is terminated for some reason, for example. In this way, when the termination of the scanner is recognized as a result of the detection of a scanning state of the scanner, the system is terminated thereafter. Then, another probe is connected thereto, and processing for starting the driving is performed.

For example, the connector 1006 may be connected in advance but the connector 1006 becomes out of connection for some reason in the middle. In this case, the connector 1006 may be connected thereto again, and the driving may be terminated thereafter. FIG. 51 shows a timing chart of light source output control signals LC in this case for a light source output permitting signal LE, drive waveform output permitting signal OE, scanning state signal SS and connection detection signal CC.

FIG. 52 shows a flow of a change of each of the light source output permitting signal LE, drive waveform output permitting signal OE, scanning state signal SS and connection detection signal CC. FIG. 53 shows a flow of a change of a light source output control signal LC for each of the light source output permitting signal LE, drive waveform output permitting signal OE, scanning state signal SS and connection detection signal CC.

In processing based on the flowchart in FIG. 53, changes in states of the light source output permitting signal LE, drive waveform output permitting signal OE, scanning state signal SS and connection detection signal CC in the processing shown in FIG. 52 are constantly monitored. In accordance therewith, a light source output control signal LC for ON/OFF of the laser is output.

The connector 1006 connecting the optical scanning probe 1002 and the confocal observation apparatus 1003 integrally includes an electric connector portion 1071, a photoconnector portion 1072 and an air outlet 1073. The electric connector portion 1071 transmits a drive waveform and connection detection signals as shown in FIG. 54. The photoconnector portion 1072 transmits laser light. The air outlet 1073 supplies air (or possibly fluid) from an air compressor 1061 (see FIG. 45).

The other side of the photoconnector portion 1072 has optical fiber. The photoconnector portion 1072 is securely fixed to the connector 1006 with resin or adhesive such that the folding of the optical fiber can be prevented at a part connecting the connector 1006 and the optical fiber.

A valve (not shown) thereof is opened in accordance with the connection of the air outlet 1073 so that the air outlet 1073 can supply to the probe. An O-ring (not shown) is provided on the rim of the connecting part of the connector 1006, and a watertight structure can be obtained by the connection.

The arrangement of the connector 1006 in FIG. 54 is just one example. The arrangement of the electric connector portion 1071, the photoconnector portion 1072 and the air outlet 1073 may be different therefrom.

In FIG. 54, the air compressor 1061 for air supply is independent from the confocal observation apparatus 1003. The air compressor 1061 can be removably attached to the connector 1006 through the confocal observation apparatus 1003 but may be integrated with the confocal observation apparatus 1003. The air compressor 1061 may be controlled by the confocal observation apparatus 1003 and/or software.

As shown in FIG. 55, a shutter 1101 may be provided on the axis of emitted light of the laser light source 1031. Thus, the laser driver 1032 may perform light-emission control of the laser light source 1031 and control the opening/closing of the shutter 1101 in accordance with a light source output control signal LC.

The shutter 1101 may be a mechanical shutter, which opens and closes mechanically. The shutter 1101 may be a rotatable polarizer. The shutter 1101 may rotate in accordance with a state of the light source output control signal LC and may allow the light to pass through or shield the light.

The shutter 1101 may includes an AOM (acoustooptic modulator), which is adjusted to diffract and shield light by applying voltage thereto in accordance with a state of the light source output control signal LC and to allow light to pass through by terminating the application of voltage.

In FIG. 55, the shutter 1101 is provided between the laser light source 31 and the signal mode fiber 1033 (four-terminals coupler 1034). However, the shutter 1101 may be provided between the four-terminals coupler 1034 and the connector 1006. The shutter 1101 may be integrated with the connector 1006. Then, when the connector 1006 is inserted, the shutter 1101 may be pressed and is moved while, when the connector 1006 is removed, the shutter 1101 may be returned by a spring so as to shield light.

FIG. 56 shows a flow of changes of light source output control signal LC for changes of a light source output permit signal LE, drive waveform output permit signal OE, scanning state signal SS and connection detection signal CC in the construction shown in FIG. 55.

According to this embodiment, the laser light source is controlled in accordance with ON/OFF. Instead of powering off the laser, the same effect can be obtained even when the laser light source is controlled by decreasing the output strength of laser.

In this case, since laser is not powered off, a load on laser can be further reduced. Thus, the life of laser can be extended, and the start on driving laser again can be achieved fast, which is an advantage.

Sixteenth Embodiment

As shown in FIG. 57, an optical image capturing apparatus 2001 according to a sixteenth embodiment of the invention includes a light source 2002, optical fibers 2003$a$ and 2003$b$ and an optical scanning probe 2005. The light source 2002 generates light such as laser light. The optical fibers 2003$a$ and 2003$b$ transmit the light. The light is transmitted to the distal end side of the optical scanning probe 2005 through an optical fiber 2004 connecting to the optical fiber 2003$b$. Light is scanned on a subject 2007 by the optical scanning probe 2005 through an optical scanning optical system 2006 on the distal end side of the optical scanning probe 2005. The optical image capturing apparatus 2001 further includes means for capturing and imaging optical information by receiving the return light, transmitting the light to the optical fiber 2003$b$ side through the opposite optical path of the incident path, and receiving light guided to another optical fiber 2003$c$ side by a photocoupler 2008. An optical fiber 2003$d$ is closed, for example, at the ends so as to decrease light reflection at the ends.

Light guided to the optical fiber 2003$c$ is received by the photodetector 2009, is optoelectronically converted and is output to the A/D converter 2011. Digital signals resulting from the conversion from analog signals by the A/D converter 2011 are captured by a personal computer (abbreviated to PC, hereinafter) 2012, undergo signal processing for imaging and are output to a display 2013 as video signals. An image from return light resulting from optical scanning by the optical scanning optical system 6 is displayed on a display screen of the display 2013.

FIG. 58 shows a configuration of an optical scanning optical system 2006 on the distal end side of the optical scanning probe 5.

Light transmitted by the optical fiber 2004 is emitted from a distal end surface 2004$a$ in a minute size, is reflected by an opposed fixed mirror 2015, is reflected by a mirror portion 2017 in a scan mirror device (simply abbreviated to mirror device, hereinafter) 2016 opposing to the reflected light side, is launched and gathered into a convergence lens 2018 having a large number of aperture provided on the reflected light side and is irradiated to a subject 2007 side.

A drive signal is applied to the mirror device 2016 by optical scanning driving means 2021 in FIG. 57 through a drive signal line 2019. The mirror portion 2017 is tilt-driven by the drive signal such that the motion angle of the mirror surface can vary two-dimensionally. With this, a light beam launched into the convergence lens 2018 is two-dimensionally scanned in the direction orthogonal to the optical axis O of the convergence lens 2018. Thus, light irradiated to the subject 2007 side through the convergence lens 2018 is two-dimensionally scanned.

In this case, the light gathered to the subject 2007 side is focused at a position of a focal point 2022 in a spot manner. The light reflected at the position of the focal point 2022 follows the reverse optical path and is launched into the minute distal end surface 2004a of the optical fiber 2004. The reflected light at a different position from the focal point 2022 is not launched into the distal end surface 2004a of the optical fiber 2004.

In other words, the distal end surface 2004a of the optical fiber 2004 has a confocal relationship or near relationship thereto with the focal point 22 with respect to the optical scanning optical system 2006 including the fixed mirror 2015, the mirror device 2016 and the convergence lens 2018.

As shown in FIG. 57, the PC 2012 controls an operation for driving optical scanning by the optical scanning driving means 2021.

According to this embodiment, means 2025 for detecting a mirror motion angle in the optical scanning optical system 2006 as shown in FIGS. 58 and 59A is provided in the optical scanning optical system 2006.

The mirror device 2016 includes a mirror portion 2017 having a gimball structure resulting from etching of the other part than the hinge 2026 in the direction orthogonal to the center part of the plate. The upper plane or surface is used to reflect and scan light from the optical fiber 2004 as shown in FIG. 58.

In this case, the mirror portion 2017 on both sides of the hinge 2026 (of the hinge pair having the other hinge in the vertical direction in FIGS. 59A and 59B) and a substrate 2027 opposing thereto function as electrodes. A most part of the area of the substrate 2027 opposing to the mirror portion 2017 is N-type GND and an opposed electrode for driving the mirror portion 2017 by using electrostatic gravity. By applying a drive signal in a sinusoidal or sawtooth drive signal between the substrate 2027 and the mirror portion 2017, the mirror portion 2017 is tilted to a state indicated by a dashed line from a state indicated by a solid line in FIG. 59A.

As shown in FIG. 61 and so on, another hinge pair is provided in the direction orthogonal to the hinge 2026, and the mirror portion 2017 is tilted to the directions of both sides of the hinge. In other words, the mirror portion 2017 is two-dimensionally tilted in the direction orthogonal to the optical axis O of the convergence lens 18 in FIG. 58. Thus, light reflected by the mirror portion 2017 and gathered by the convergence lens 2018 is two-dimensionally scanned in the direction orthogonal to the optical axis O.

According to this embodiment, as shown in FIG. 58 and FIG. 59A, the center of the substrate 2027 opposing to the center part of the mirror portion 2017 has a hole 2028. Light from the optical fiber 2029, for example, is guided to the back face of the mirror portion 2017 through the hole 2028 and is reflected at the center of the back face of the mirror portion 2017.

As a result of P-scattering, a PN junction part is provided in an N-type semiconductor part of the substrate 2027 opposing to the vicinity of the center on the back face of the mirror portion 2017. Thus, a PSD sensor 2030 is provided therein. FIG. 59B shows the PSD sensor 2030 and four terminals 2031.

As shown in FIG. 59B, the PSD sensor 2030 is connected to the four terminals 2031 extending in four directions. The four terminals 2031 are reverse-biased with a same amount of voltage in use. Furthermore, the optical scanning driving means 2021 monitors a current value among the terminals through a sensor signal line 2032.

For example, when mirror portion 2017 is tilted by the application of a drive signal, the reflected light is displaced from the center of the back face. The position of a light spot P1 that the reflected light hits the PSD sensor 2030 is displaced from the center to the periphery. Most of charges generated at the hit part largely flow into the terminal side close to the light spot P1. Thus, based on the current ratio, the tilting angle (motion angle) of the mirror portion 2017 can be detected.

In the case shown in FIGS. 59A and 59B, the position where light spot P1 hits varies in the direction of the both sides of the part held by the hinge 2026, that is, in the horizontal direction. However, like the seventeenth embodiment, in reality, the outer part of the mirror portion 2017 is tiltably held by another hinge, and the mirror portion 2017 is two-dimensionally tilted thereby.

In other words, the mirror portion 2017 may be tilted in the vertical direction of FIG. 59A. Thus, the position where the light spot P1 hits varies in the vertical direction of FIG. 59B. The variation can be also detected by the PSD sensor 2030.

An output signal of the PSD sensor 2030 is transmitted to the scanning driving means 2021 through the sensor signal line 2032 and is compared with a reference value corresponding to a predetermined angle of motion in the scanning driving means 21. In accordance with the error signal, gain control is performed on a gain control amplifier, which is drive signal output means, for amplifying drive signals.

The amplitude of a drive signal applied from the gain control amplifier to the mirror device 2016 through the drive signal line 2019 is automatically controlled. Thus, the motion angle of the mirror portion 2017 is controlled so as to be a certain motion angle. Automatic control is performed such that a state for capturing an image can be kept at a state that the mirror portion 2017 is at a certain motion angle, that is, a state that the scanning range of the optical scanning optical system 2006 is a certain scanning range.

The output signal of the PSD sensor 2030 is also transmitted to the light source 2002 through the sensor signal line 2032. If the output signal is equal to or lower than a predetermined threshold value, that is, a slight motion angle, which does not need two-dimensional imaging, the light emission by the light source 2002 is terminated. Then, the wasteful light irradiation can be prevented. Thus, the life of the laser diode as the light source 2002 can be increased.

An output signal of the PSD sensor 2030 is transmitted to the scanning driving means 2021 and the light source 2002 through the sensor signal line 2032 here. However, the output signal may be transmitted to the scanning driving means 2021, for example, and it is judged whether or not the output signal is higher than a predetermined first threshold value (which is a reference value for judging whether it is a small motion angle not requiring two-dimensional imaging). If larger than the first threshold value, the signal may be compared with a second threshold value for controlling to obtain a certain motion angle. In accordance with the error signal, the amplitude of the drive signal may be controlled.

In this case, if equal to or lower than the first threshold value, a signal for terminating the light emission of the light source 2002 may be transmitted from the scanning driving means 2021 to the light source 2002. Then, the light emission may be terminated.

According to this embodiment, the scanning driving means 2021 or the like monitors an output signal from the PSD sensor 2030, which is the motion angle detecting means 2025, and judges whether or not the output signal is a motion angle equal to or lower than a threshold value, which is a reference for judging the necessity for two-dimensional imaging. Based on the judgment result, if the motion angle is equal to or lower than the threshold value, the light emission by the light source 2002 is terminated. If a motion angle, which allows two-dimensional imaging, is detected, the amplitude of a drive signal is automatically controlled such that the detected motion angle can be a certain motion angle. Thus, an image for a certain scanning range (that is an image at a certain magnification) may be displayed, and the image may be stored in the PC 2012.

As shown in FIG. 60, the optical scanning probe 2005 is covered by a long and thin and flexible sheath 2034 and can be inserted through a channel of an endoscope 2035. The endoscope 2035 has a long and narrow insert portion 2036 and an operating portion 2037 provided at the rear end of the insert portion 2036. A treating device insert opening 2038 is provided in the vicinity of the front end of the operating portion 2037. The treating device insert opening 2038 is linked to a channel within the insert portion 36. The optical scanning probe 2005 can be inserted through the treating device insert opening 2038.

In order to check whether a subject is a lesion tissue or not under observation by the endoscope 2035, the distal end of the optical scanning probe 2005 projects from the end of the channel. Then, the end face is set near the surface of the subject 2007 to be checked, and optical scanning is performed thereon by the optical scanning probe 2005. By capturing and imaging the optically scanned signal, the lesion tissue is enlarged and is observed. Thus, a microscopic image can be obtained.

According to the sixteenth embodiment having the above-described construction, a motion angle (tilt angle) of the mirror portion 2017 in the mirror device 2016 in the optical scanning optical system 2006 within the distal end part of the optical scanning probe 2005 is detected by the PSD sensor 2030. Thus, if the mirror portion 2017 is moved to an extent allowing imaging, the mirror portion 2017 is controlled to move at a certain motion angle. In synchronization with the motion angle, imaging processing is performed based on the return light from the subject 7. Thus, the image resulting from the imaging is displayed on the display 13.

On the other hand, if the mirror portion 2017 is being moved by a small motion angle not requiring imaging or is terminated without motion, the light emission of the light source 2 is terminated. Thus, the wasteful light generation at a state that imaging is essentially meaningless or imaging is not possible can be terminated, and the decrease in life of the light source 2002 can be prevented.

Therefore, according to this embodiment, an optical scan image resulting from optical scanning can be obtained in a stable manner at a certain motion angle, that is, with the scanning in a predetermined scanning range, which is significantly effective for diagnosis. By terminating the light emission of the light source 2002 for a state with a motion angle equal to or lower than a motion angle, which cannot be imaged, the life of the light source 2002 can be increased.

The optical image capturing apparatus 2001 according to the sixteenth embodiment is especially effective by being applied to the optical image pickup apparatus according to the first to fourteenth embodiments.

Seventeenth Embodiment

FIG. 61 shows a front view of a mirror device 2041 according to a seventeenth embodiment of the invention.

The mirror device 2041 (internally) has a mirror portion 17 tiltably held by hinges 2026b and 2026b orthogonal to hinges 2026a and 2026a within a mirror outer frame portion (gimball ring) 2042 tiltably held by the hinges 2026a and 2026a.

The mirror outer frame portion 2042 is driven by nonresonant driving in response to a drive signal, and the internal mirror portion 2017 is driven by resonant driving. Thus, light reflected by the mirror portion 2017 is two-dimensionally scanned (tilt scanning).

According to this embodiment, as enlarged in FIG. 62A, a strain gauge 2044 containing polysilicon or the like is provided on a surface near the rim close to the hinge 2026a, for example, in the mirror portion 2017 being subject to resonant driving.

As shown in FIG. 62B, a weight 2045 is provided at the end projecting in the direction of the radius of the mirror portion 2017. The strain gauge 2044 functions as an acceleration sensor for detecting an acceleration acting on a strain gauge part near the weight 2045. In other words, in comparison with the state in FIG. 62B, when an acceleration acts on the end of the mirror portion 2017 as shown in FIG. 62C, the strain gauge 2044 is stretched. Thus, the acceleration can be detected.

The strain gauge 2044 is connected to motion angle calculating means 2046. The motion angle calculating means 2046 calculates a motion angle as follows.

An output signal of the motion angle calculating means 46 is sent to optical scanning driving means 2021 and a light source 2002 in FIG. 57 and is controlled based on the detected motion angle like the sixteenth embodiment.

An operation for motion angle calculation according to this embodiment will be described next.

The mirror portion 2017 is driven by a drive signal, and the inclination of the mirror portion 2017 varies by $A \sin \omega t$ where an angular speed of the drive signal is $\omega$ and time is t. Here, A refers to an amplitude.

Thus, the speed of the end (rim part) of the mirror portion 2017 is a value resulting from the differentiation of the slope, that is, a value proportional to $A\omega \cos \omega t$.

The acceleration acting on the mirror end is a value resulting from a further differentiation, that is, a value proportional to $A\omega^2 \sin \omega t$.

As a result, the output signal of the strain gauge 2044 functioning as an acceleration sensor at the end, that is, acceleration information is input to the motion angle calculating means 2046. The motion angle calculating means 2046 performs two differentiations on the acceleration information and calculates the motion angle. Thus, the motion angle in the resonant driving state can be detected.

If the detected motion angle is a predetermined motion angle, the state for optical scanning is maintained. If the detected motion angle is equal to or lower than the predetermined value, the light emission of the light source 2002 is terminated.

For simple description, the detection of a motion angle of the mirror portion 2017 subject to resonant-driving has been described above. When the mirror outer frame portion 2042 is driven by nonresonant driving, a strain gauge is provided.

Thus, a drive waveform of nonresonant driving is numerically referred and is calculated so that a motion angle by nonresonant driving can be detected.

In other words, according to this embodiment, substantially the same advantages can be obtained as those of the sixteenth embodiment.

An optical capturing apparatus according to the seventeenth embodiment is especially effective when the optical capturing apparatus is applied to the optical image pickup apparatus according to the fifteenth embodiment.

Eighteenth Embodiment

An eighteenth embodiment of the invention will be described next. FIG. 63 shows a motion-angle detecting mechanism 2052 provided in a mirror device 2051 according to the eighteenth embodiment. According to the eighteenth embodiment, a motion angle is detected by detecting that an electrostatic capacitance between a mirror portion 1207 (to be tilted) and a substrate 2026 opposing thereto is changed in accordance with a distance between them.

Like the case shown in FIGS. 59A and 59B, the mirror portion 2017 is tiltably held by a hinge 2026. Both ends of the mirror portion 2017 tiltably held by the hinge 2026 as a fulcrum are connected to capacitance detecting means 2053. Thus, an electrostatic capacitance (abbreviated as C, hereinafter) with respect to a substrate 2027, which is the ground (GND) can be detected.

A sinusoidal drive signal is applied between (the electrode of) the mirror portion 2017 and the substrate 2026, which is the GND, opposing thereto. The mirror portion 2017 is driven by the electrostatic gravity acting therebetween. As a distance between the mirror portion 2017 and the GND (substrate 2026) varies, the size of the C-component varies.

On the other hand, a high frequency component having a small amplitude may be added to the drive signal (driving voltage) to be applied to both of them. The driving of the mirror portion 2017 is not affected thereby if the frequency is sufficiently larger than the resonant frequency of the mirror portion 2017.

By using the high frequency component, the size of the C-component can be measured. Thus, an amount of change of the mirror portion 2017 can be measured. In other words, the capacitance detecting means captures the high frequency component through a band-pass filter allowing the high frequency component to pass through. Thus, the C-component can be detected from a current (amplitude) having the captured high frequency component. Then, an effective distance of both sides of the hinge 2026 in the mirror portion 2017 and a motion angle of the mirror portion 2017 can be calculated from the value of the C-component.

A part indicated by a dashed line in FIG. 63 refers to a state where the mirror portion 17 is tilted. On the side (left side) away from the substrate 27, C is calculated small while C is calculated large on the other side. The shown Va and Vb refer to voltages for tilting the mirror portion 17.

By dividing an opposing effective area by C, a value proportional to a distance can be calculated, and a motion angle can be calculated.

Also according to this embodiment, the C-component of the mirror portion 2017 is detected. However, as shown in FIG. 61, a two-dimensional motion angle can be detected by detecting a C-component on the mirror frame portion 2042 side.

According to this embodiment, a motion angle can be detected two-dimensionally without changing the construction of the mirror device 2051 largely. In other words, with a simple construction, substantially the same advantages can be obtained as those of the sixteenth embodiment.

The optical image capturing apparatus according to the eighteenth embodiment is especially effective when the optical image capturing apparatus is applied to the optical image pickup apparatus according to the fifteenth embodiment.

Nineteenth Embodiment

A nineteenth embodiment of the invention will be described next. FIG. 64A shows a motion-angle detecting mechanism in a mirror device 2041 according to the nineteenth embodiment. FIG. 64B shows a section of the mirror device 2041.

In the mirror device 2041 shown in FIG. 61, the motion-angle detecting mechanism has comb-like electrodes 2057 and 2058 instead of the strain gauge 2044. The comb-like electrodes 2057 and 2058 are connected to capacitance detecting means as shown in FIG. 63.

FIG. 64B shows a construction of the one comb-like electrode 2057. The other comb-like electrode 2058 has the same construction.

Small plate pieces 2057$a$ and 2057$b$ are opposed to each other between a mirror frame portion 2042 and an internal mirror portion 2017 in a part opposing to the hinge 2026$a$, for example, in the mirror portion 2017 so as to obtain the comb-like electrode 57.

When the mirror portion 2017 is tilted as indicated by the dashed line in FIG. 64B, for example, the opposing area part of the plate pieces 2057$a$ and 2057$b$ of the comb-like electrode 2057 decreases. Thus, the motion angle (tilting angle) of the mirror portion 2017 can be calculated from the C-component proportional to the area.

Similarly, a motion angle of the mirror frame portion 2042 can be calculated from the value of the C-component on the comb-like electrode 2058.

In the motion-angle detecting mechanism adopting the comb-like electrodes 2057 and 2058 according to this embodiment, a detected size of C can be linearly proportional to a motion angle. Thus, a motion angle can be detected easily with high accuracy.

In driving, the value of C may be designed to vary from zero (0) to a maximum value of C. In other words, a variation rate may be designed significantly large, and the detection accuracy can be improved. In addition, substantially the same advantages as those of the sixteenth embodiment are obtained.

The optical image capturing apparatus according to the nineteenth embodiment is especially effective when the optical image capturing apparatus is applied to the optical image pickup apparatus according to the fifteenth embodiment.

Twentieth Embodiment

Next, a twentieth embodiment of the invention will be described. FIG. 65A shows a motion-angle detecting mechanism in the mirror device 2041 according to the fifth embodiment. FIG. 65B shows a section of the mirror device 2041.

In FIG. 61, the motion-angle detecting mechanism according to this embodiment has a square (or circular) ring-shaped sensing coil 2061 in the mirror portion 2017 instead of the strain gauge 2044. Furthermore, as shown in FIG. 65B, a permanent magnet 2062 is provided on the bottom surface of the mirror device 2041. A magnetic flux B lies through the sensing coil 2061 thereabove.

Both ends of the sensing coil 2061 are connected to inductive motive force measuring means 2063. Thus, inductive motive force generated by the sensing coil 2061 is measured (detected), and a tilting angle (motion angle) of the mirror portion 2017 can be calculated from the inductive motive force.

In other words, when the mirror portion 2017 is resonantly driven, a value of the magnetic flux B extending through the sensing coil 2061 on the surface of the mirror portion 2017 changes. In accordance with the change, inductive motive force is generated in the sensing coil 2061.

The inductive motive force (voltage) is measured by the inductive motive force measuring means 2063. In accordance with the value, an angular speed of (the sensing coil 2061 of) the mirror portion 2017 can be detected. In accordance with the integral amount, the motion angle of the mirror portion 2017 can be monitored.

By providing a sensing coil also on the mirror frame portion 2042 side, a two-dimensional motion angle can be detected.

Also according to this embodiment, a motion angle can be detected with high accuracy with a simpler construction.

The optical image capturing apparatus according to the twentieth embodiment is especially effective when the optical image capturing apparatus is applied to the optical image pickup apparatus according to the fifteenth embodiment.

Twenty First Embodiment

Next, a twenty first embodiment of the invention will be described. FIG. 66 shows a motion-angle detecting mechanism in a mirror device 2041 according to the twenty first embodiment.

A motion angle detecting mechanism according to this embodiment, strain gauges 2071 and 2072 are provided on two hinges 2026*a* and 2026*b* instead of the strain gauge 2044 in the mirror portion 2017 in FIG. 66. The strain gauges 2071 and 2072 are connected to resistance change measuring means 2073. How much the hinges 2026*a* and 2026*b* are bent by the strain gauge 2071 and 2072 is measured in accordance with a change in resistance due to the bending. Thus, a motion angle can be detected.

More specifically, both ends of the strain gauge 2071 mounted on the one hinge 2026*a* are connected to the resistance change measuring means 2073 through a wire 2074 for motion-angle sensing. Both ends of the strain gauge 2072 mounted on the other hinge 2026*b* are connected to the resistance change measuring means 2073 through a wire 2075 for motion-angle sensing.

Electrodes 2076*a* and 2076*b* having a mirror function on both sides of a line connecting the hinges 2026*b* and 2026*b* in the mirror portion 2017 are connected to scan driving means 2021 through mirror drive lines 2077*a* and 2077*b*. A drive signal is applied to the electrode 2076*a* and 2076*b*.

Electrodes 2078*a* and 2078*b* on both sides of a line connecting the hinges 2026*a* and 2026*a* in the mirror frame portion 2042 are connected to scan driving means 2021 through mirror drive lines 2079*a* and 2079*b*. A drive signal is applied to the electrode 2078*a* and 2078*b*.

In this way, according to this embodiment, the drive signal line and the wire for mirror motion-angle sensing are provided separately. Thus, the resistance change measuring means 2073 can detect changes in resistance of the strain gauges 2071 and 2072 and can detect motion angles of the mirror frame portion 2042 and mirror portion 2017.

FIG. 67 shows a variation example. In the variation example, a wire is used for both driving and sensing.

Generally, since an electrostatically driven device has a C-component and an infinite resistance (abbreviated as R, hereinafter), current does not keep flowing therein. Therefore, when a strain gauge (=R-component) is provided therein in parallel, only an amount of change in resistant value of the strain gauge can be detected from the wire for driving.

Based on the principle, the construction as shown in FIG. 67 is provided. In other words, both of the electrodes 2076*a* and 2076*b* of the mirror portion 2017 are connected resistance change measuring & scan driving means 2081 for both resistance change measuring and scan driving through wires 2080*a* and 2080*b* for both mirror driving and sensing.

The electrodes 2078*a* and 2087*b* of the mirror frame portion 2042 are also connected to the resistance change & scan driving means 2081 for both resistance change measuring and scan driving through the wires 2082*a* and 2082*b* for both mirror frame driving and sensing.

The wires 2082*a* and 2082*b* connected to the electrodes 2078*a* and 2078*b* are connected to ends of the strain gauge 2071 on the hinge 2026*a*. The resistance of the strain gauge 2071 can be detected by the resistance change measuring & scan driving means 2081.

The wire 2080*a* connecting to the electrode 2076*a* is connected to one end of the strain gauge 2072 on the hinge 2026*b*. The other end of the strain gauge 2072 is connected to a wire part extending on the hinge 2026*b* from the electrode 2076*b*. The resistance of the strain gauge 2072 can be detected by the resistance change measuring & scan driving means 2081.

According to this variation example, a motion angle can be detected with a simpler configuration. In addition, the same advantages as those of the sixteenth embodiment can be provided.

The optical image capturing apparatus according to the twenty first embodiment is especially effective when the optical image capturing apparatus is applied to the optical image pickup apparatus according to the fifteenth embodiment.

Twenty Second Embodiment

Next, a twenty second embodiment of the invention will be described. FIG. 68A shows a motion-angle detecting mechanism in an optical scanning optical system 6 according to the twenty second embodiment.

According to this embodiment, a range of a motion angle of a mirror portion 2017 is further increased with respect to the above-described ranges. Thus, timing for launching light into the outside of an effective diameter of a convergence lens 2018 is created. Image capturing is performed in a range of a mirror motion angle for fitting light within the lens effective diameter. By using the timing for launching light to the outside of the effective diameter with a larger motion angle than the motion angle in the range, a motion angle can be detected and/or calibrated.

The motion angle detecting mechanism according to this embodiment, a PD (photodiode) 2085 is provided in a part outside of the lens effective diameter on the back side opposing to the mirror device 2016 in the convergence lens 2018. The output of the PD 2085 indicates that light has moved by the mirror portion 2017 up to an angle allowing light to launch to the PD 2085. Based on the fact and the drive voltage at that time, a relationship between a voltage and a motion angle can be calibrated.

In this case, multiple PDs 2085 are provided in directions of two-dimensional scanning by the mirror portion 2017 (two PDs 2085 are also provided vertically on FIG. 68A).

The rest is the same as that of the construction described in FIG. 58. According to this embodiment, a motion angle can be detected two-dimensionally with a simple construction. In addition, the same advantages as those of the sixteenth embodiment are provided.

FIG. 68B shows a first variation example. In FIG. 68B, a reflective mirror (mirror) 2086 is provided outside of the lens effective diameter. Like the case in FIG. 68A, when light scanned by the mirror portion 2017 moves largely up to the outside of the effective diameter, the light is reflected by the mirror 2086. The reflected light is reflected in order of the mirror portion 2017 and fixed mirror 2015 and returns to an optical fiber 2004. Since the return light here has a much higher strength than that of rear scattering light by biological observation, the return light can be retrieved as a motion angle signal of the mirror portion 2017. Thus, the motion angle can be detected.

FIG. 69A shows a second variation example.

A real probe contains a highly dense implementation and is narrow. A spacer is provided between the convergence lens 2018 and the mirror device 2016 in order to fix a positional relationship therebetween.

In this variation example, as shown in FIG. 69A, a PD is provided on the internal radius of the spacer 2087 for fixing the convergence lens 2012. Here, the PD is a multi-function Integrated Film (abbreviated to MIF, hereinafter) 2088. The MIF 2088 may be integrated with a flexible wire having a polyimide film so as to form a silicon device having a thickness reduced to the order of several μm. The construction is disclosed in Japanese Unexamined Patent Application Publication No. 7-86551.

Multiple thin silicon device may be integrated on one polyimide wire. Since silicon is thin, a silicon part having a reduced thickness may be pasted onto a surface curved to some extent. Since multiple small PDs can be aligned, the PDs can be implemented onto the internal surface of the spacer 2087 in some manner. Also in this case, substantially the same advantages can be obtained.

FIG. 69B shows a third variation example.

In this variation example, besides the light for observation (that is, light with λ1 where the wavelength may have a band like an SLD (superluminescent diode)), light (with λ2) for observing a driving state is launched. An anti-reflection coat (AR coat) 2091 compliant with light with the wavelength λ1 is provided on the surface of the convergence lens 2018.

However, the reflecting function of the AR coat 2091 is lowered for the light with λ2 having a different wavelength. The light with λ2 reflected by the lens surface returns to the optical fiber 2004 to some extent and can be detected from a device outside of the probe. Thus, the resonant frequency or nonresonant frequency can be checked.

A construction of an image capturing apparatus 2001B according to this variation example is shown in FIG. 70. The image capturing apparatus 2001B includes a light source 92 for generating light with the wavelength λ2 is provided in addition to the light source 2 for generating light with the wavelength λ1 in the image capturing apparatus 2001 in FIG. 57. Light beams from the light sources 2002 and 2092 are launched into the optical fibers 2003e and 2003f, respectively, and are mixed in an optical coupler 2093. Then, the light is guided to the optical fiber 2003a side. An optical fiber 2003g is closed at the ends so as to reduce reflected light like the optical fiber 2003d.

The light guided to the optical fiber 2003a is transmitted to an optical scanning optical system 2006 side shown in FIG. 69B through the optical fiber 2004 within the optical scanning probe 2005B and is irradiated to a subject 2007 side. The optical scanning probe 2005B is only different from the optical scanning probe 2005 in FIG. 57 in the construction of the motion-angle detecting means.

The return light on the subject 2007 side and light reflected by the lens surface follow an opposite path of the outward path. A part of the light is separated into reflected light and passing light by a dichroic prism 2094 through the optical fiber 2003c. The reflected light with the wavelength λ1 is received by a photodetector 2009.

On the other hand, the transmitted light with the wavelength λ2 is received by the photodetector 2095. The optoelectronically converted signal is input to operation state judging means 2096, and the operation state judging means 2096 controls operations of the light sources 2002 and 2092 in accordance with the judgement result. The other construction is the same as the construction in FIG. 57, and the description will be omitted.

The operation state judging means 2096 detects light with the wavelength λ2 periodically when the mirror portion 2017 is tilted. In this case, the operation states of the light emission of the light sources 2002 and 2092 are maintained. On the other hand, like the case that the mirror portion 2017 is not tilted or is tilted slightly, when light with the wavelength λ2 is always detected or is almost always detected, light is not moved at a predetermined motion angle. Thus, since imaging becomes meaningless, the operations of light emission of the light sources 2002 and 2092 are terminated. Therefore, the wasteful reduction of the lives of the light sources 2002 and 2092 can be prevented.

The optical capturing apparatus according to the twenty second embodiment and variation examples are especially effective when the optical capturing apparatus is applied to the optical image pickup apparatuses according to the first to fourteenth embodiment.

Twenty Third Embodiment

A twenty third embodiment of the invention will be described next. FIG. 71 shows motion-angle judging means provided on the periphery of the mirror device according to the twenty third embodiment. According to this embodiment, means is provided for judging whether a mirror portion 2017 of a mirror device 2041 has been driven or not.

As shown in FIG. 71, a sound sensor 2097 is provided around the mirror device 2041, for example, on the mirror device 2041 or near the mirror device 2041 within a probe.

A resonant frequency of the mirror device 2041 is about 3 kHz, and, if resonant driving is performed therein, the sound thereof is transmitted to the surroundings. A low-speed scan side is driven by sawtooth waves at about 20 Hz. The mirror device 2041 is swung at a certain speed and also the mirror portion 2017 moves rapidly when returning to an initial portion. As a result, the higher harmonics component can be retrieved as sounds.

As described above, a driving state of the mirror device 2041 can be judged by the sound sensor 2097. Based on the judgement result, an operation of the light source 2002 in FIG. 57 can be controlled.

The optical capturing apparatus according to the twenty third embodiment is especially effective when the optical capturing apparatus is applied to the optical image pickup apparatus according to the fifteenth embodiment.

Twenty Fourth Embodiment

A twenty fourth embodiment of the invention will be described next. FIG. 72 shows a motion-angle detecting mechanism in a mirror device according to the twenty fourth embodiment. The motion-angle detecting mechanism has a construction close to that of the variation example of the sixteenth embodiment.

In FIG. 58, light is irradiated from an optical fiber 2029 to the back side of a mirror portion 2017 through a hole 2028 of a substrate 2027 on the back side of the mirror portion 2017, and the reflective spot is detected by a PSD sensor 2030. On the other hand, according to this embodiment, a larger hole 2028' is provided. Light is irradiated by an LED (or plane light emitting laser) 2098 on the bottom surface side to the back of the mirror portion 2017. The reflected light is received by a two-part split (or four-part split) PD 2099 below the LED 2098 or the like. The other construction is the same as that of the sixteenth embodiment. This embodiment has substantially the same advantages as those of the sixteenth embodiment.

The optical capturing apparatus according to the twenty fourth embodiment is especially effective when the optical capturing apparatus is applied to the optical image pickup apparatus according to the first to fourteenth embodiments.

Twenty Fifth Embodiment

A twenty fifth embodiment of the invention will be described next. FIG. 73 shows an optical scanning optical system 2006 within an optical scanning probe according to the twenty fifth embodiment. A motion-angle detecting mechanism is provided in a mirror device 2016 in the optical scanning optical system 2006. The motion-angle detecting mechanism has a construction close to that of the variation example of the sixteenth embodiment. Light from a light source 2002 is used as light used for motion-angle detection.

A PD 2100 is provided on the surface of a substrate 2027 on the back side of a mirror portion 2017 in the mirror device 2016. Light passes through the end of the mirror portion 2017 and is subject to a tilting movement. The light is received by the PD 2100 and detects the tilting movement (motion angle).

FIG. 74A shows a sectional structure of a mirror device 16. FIG. 74B is an enlarged view of a part indicated by the dashed line in FIG. 74A.

Light emitted from an optical fiber 4 as shown in FIG. 73 is reflected by a fixed mirror 15 and is launched into the mirror device 16 at some angle.

In this case, as shown in FIGS. 74A and 74B, the incident angle of light to the mirror device 2016 is around 25 degrees. The motion angle of the mirror portion 2017 of the mirror device 2016 is several degrees (assumed as 3 degrees in FIG. 74A). As shown in the enlarged view of the end of the mirror portion 2017, a shadow part thereof moves on the substrate 2027 even with the motion angle of 3 degrees. Thus, the PD 2100 is disposed in the part, and motion-angle information can be obtained from the output.

Also according to this embodiment, a motion angle can be detected with a simple construction.

The optical capturing apparatus according to the twenty fifth embodiment is especially effective when the optical capturing apparatus is applied to the optical image pickup apparatus according to the first to fourteenth embodiments.

In the description above, when the mirror portion 2017 has a motion angle not needing imaging, the light emission of the light source 2 is terminated, that is, the irradiation light is terminated. However, when, like a laser diode as the light source 2002, the output and/or wavelength vary in accordance with a temperature and a time is required for obtaining a stable operation, the light to a subject side may be shielded instead of the termination of the light emission of the light source 2002.

Twenty Sixth Embodiment

An optical image capturing apparatus 3010 according to a twenty sixth embodiment of the invention includes, as shown in FIG. 75, a fixed reflective mirror 3012, a scan mirror 3014 and a convergence lens 3013. The fixed reflective mirror 3012 reflects observation light irradiated from a fiber 3011 for guiding observation light to the scan mirror 3014, which will be described later. The scan mirror 3014 has a mirror portion 3015 for inclining observation light reflected from the fixed reflective mirror 3012 by using voltage applied through a lead line 3016. The convergence lens 3013 gathers observation light reflected from the mirror portion 3015 of the scan mirror 3014 and is brought into a focus on a subject in the body.

In other words, observation light brought into a focus on the subject in the body from the convergence lens 3013 can scan the subject by adjusting and driving a tilting angle of the mirror portion 3015 of the scan mirror 3014 in accordance with the voltage applied through the lead line 3016.

The observation light having scanned the subject is reflected at the subject, and the reflected light is captured to an optical fiber 3011 through the opposite path of the path of the irradiation of the observation light to the subject.

A configuration of the scan mirror 3014 of the image capturing apparatus 3010 will be described with reference to FIGS. 76 and 77.

The scan mirror 3014 includes a rectangular-parallelepiped silicon substrate 3021 and a plate wafer 3017. The plate wafer 3017 has a rectangular film having two layers of silicon nitride film and silicon included in the mirror portion 3015 stacked on the upper surface of the silicon substrate 3021. A concave 3018 corresponding to the mirror portion 3015 provided in the plate wafer 3017 is bored in the upper surface of the silicon substrate 3021. Furthermore, the plate wafer 3017 is mounted and pasted thereto.

The plate wafer 3017 includes a plate wafer substrate portion 3017a with a predetermined width along the perimeter and an opening 3017b substantially similar to the outer shape. The plate wafer 3017 has a substantial square shape. The opening 3017b has a form similar to that of the outer diameter of the plate wafer 3017, and a mirror support 3019 containing silicon nitride film is disposed therein. The center of opposing sides of the mirror support 3019 is held in the plate wafer substrate portion 3017a of the plate wafer 3017 by hinges 3020a and 3020b. In other words, the mirror support 3019 is tilted and is driven about the hinges 3020a and 3020b.

The center of the mirror support 3019 has a substantially circular opening, and a circular mirror portion 3015 containing silicon nitride film is disposed within the opening. The mirror portion 3015 is held by the mirror support 3019 through the hinges 3022a and 3022b at a position axially orthogonal to the hinges 3020a and 3020b of the mirror support 3019. In other words, the mirror portion 3015 is tilted and is driven about the hinges 3022a and 3022b.

In other words, the mirror support 3019 and the mirror portion 3015 are tilted and driven in directions, which are orthogonal to each other, that is, in two axial directions about the hinges 3020a and 3020b, 3022a and 3022b, respectively.

The mirror portion 3015 has a layer structure having a thin layer of silicon 3042 with a thickness of 10 μm, a silicon nitride film 3044 and reflective films 3029 and 3030. The mirror support 3019 has a layer structure having a thin layer of silicon 3042, a silicon nitride film 3044 and wires 3031, 3032, 3033 and 3034, which will be described later. In other words, the wires 3031 to 3034 are disposed on the uppermost layer of the mirror support 3019 instead of a reflective film.

The mirror portion 3015 has two reflective films 3029 and 3030 with reference to the center line connecting the hinges 3022a and 3022b.

The wires 3031 to 3034 are used for voltage application for tilting and driving the mirror support 3019 and mirror portion 3015 by applying voltage to the mirror support 3019 and the mirror portion 3015 and using electrostatic gravity.

Next, a configuration of the mirror portion 3015 and hinge 3022a within a range indicated by an ellipse B shown in FIG. 77 will be described with reference to FIG. 79. The hinge 3022a has a silicon nitride film 3044 having a beam shape and a wire 3031 having two-layer film of aluminum 3049 and titan nitride 3048 extending to the mirror portion 3015 through and on the surface of the silicon nitride film 3044.

The mirror portion 3015 has a layer structure including the thin film of silicon 3042, the silicon nitride film 3044 from the hinge 3021 and the reflective film 3029. The reflective film 3029 has a layer structure having chrome 3047 for improving adhesion and gold 3046, which is a real reflective surface.

The distal end of the wire 3031 of the hinge 3022a is inserted to a part of the end of the reflective film 3029 so that the reflective film 3029 and the wire 3031 are tightly stacked. Thus, the reflective film 3029 and the wire 3031 can be electrically continuous. The hinge 3022b of the mirror portion 3015 has the same construction as that of the hinge 3022a. The constructions of the hinges 3020a and 3020b of the mirror support 3019 have the same constructions of the hinges 3022a and 3022b.

The reflective films 3029 and 3030 and the wires 3031 to 3034 are conductors, and the silicon nitride film 3044 is an insulator. Thus, the reflective films 3029 and 3030 and the wires 3031 to 3034 are disposed in an insulating manner on the surface of the silicon nitride film 3044 included in the mirror portion 3015 and the mirror support 3019 excluding a specific area.

The electric connection of the thin film of silicon 3042 of the mirror portion 3015 and the mirror support 3017, the reflective films 3029 and 3030 and the wires 3031 to 3034 is achieved by contact portions 3038 and 3039 provided in the reflective films 3029 and 3030 of the mirror portion 3015 and contact portions 3036 and 3037 provided in the mirror support 3017.

The construction of the contact portions 3036 to 3039 will be described with reference to FIG. 78 and with respect to the contact portion 3039 provided in the mirror portion 3015 in an ellipse A shown in FIG. 76, for example.

A P+ area 3043 in which a high concentration of boron is scattered is formed in the thin film of silicon 3042 in a part on which the contact portion 3039 of the mirror portion 3015 will be formed. The silicon nitride film 3044 having an opening is formed on the surface of the formed P+ area 3043. A contact pad 3045 having a thin film of aluminum is formed through the opening. The contact pad 3045 and the P+ area 3043 are brought into conduction. Then, the reflective film 3029 is formed on the upper surface of the contact pad 3045.

The other contact portions 3036 to 3038 have the same construction. However, the wires 3032 and 3034 are disposed in the contact portions 3036 and 3037 instead of the reflective film 3029 of the contact portions 3038 and 3039.

The arrangement of the wires 3031 to 3034 will be described below. As shown in FIG. 77, the wire 3031 having the distal end connected to the reflective film 3029 of the mirror portion 3015 extends from the surface of the hinge 3022a near the internal radius of a circular hole in which the mirror portion 3015 in the mirror support 3019 is provided to the pad 3024 provided in the plate wafer 3017a through the surface of the hinge 3020a of the mirror support 3019. The wire 3033 having the distal end connected to the reflective film 3030 of the mirror portion 3015 extends from the surface of the hinge 3022a near the internal radius of the circular hole in which the mirror portion 3015 in the mirror support 3019 is provided to the pad 3026 provided in the plate wafer 3017a through the surface of the hinge 3020b of the mirror support 3019.

The wire 3032 connected to the contact portion 3036 of the mirror support 3019 extends from the surface of the mirror support 3019 to the pad 3025 provided in the plate wafer 3017a through the surface of the hinge 3020a of the mirror support 3019. The wire 3034 connected to the contact portion 3037 of the mirror support 3017 extends from the surface of the mirror support 3019 to the pad 3027 provided in the plate wafer 3017a through the surface of the hinge 3020b of the mirror support 3019.

In other words, the pad 3024 and the pad 3026 are brought into conduction through the wire 3031, the reflective film 3029 of the mirror portion 3015, the contact portion 3039, the thin film of silicon 4302 of the mirror portion 3015, the contact portion 3038, the reflective film 3030 of the mirror portion 3015 and the wire 3033. The pad 3025 and the pad 3027 are brought into conduction through the wire 3032, the contact portion 3036, the thin film of silicon 3042 of the mirror support 3019, the contact portion 3037 and the wire 3034.

The plate wafer substrate 3017a has pads 3040 and 3028 in addition to the pads 3024 to 3027. The pad 3040 has an opening 3041 reaching to a silicon substrate 3021 in the plate wafer 3017a. The pad 3040 and the silicon substrate 3021 are electrically brought into conduction through the opening 3041. The pad 3040 is connected to the pad 3028 through the wire 3035 on the plate wafer 3017a.

A lead line 3016 shown in FIG. 75 is connected to the pads 3024 to 3028. A voltage application lead line for tilt-driving the mirror portion 3015 is connected to the pads 3024 and 3026. A voltage application lead line for tilt-driving the mirror support 3019 is connected to the pads 3025 and 3027. The ground lead line is connected to the pad 3028.

Operations of the optical image capturing apparatus having the above-described construction will be described. The ground potential is connected to the pad 3028. Sinusoidal potentials having opposite phases from each other are applied to the pads 3024 and 3026. The sinusoidal frequency is defined to a resonant frequency of the mirror portion 3015.

Resistant values of the wires 3031 and 3033 connecting to the pads 3024 and 3026 and reflective films 3029 and 3030 are defined much smaller than that of the thin film of silicon 3042 of the mirror portion 3015. Thus, potentials input to the pads 3024 and 3026 generate a potential distribution in accordance with a resistant component within the thin film of silicon 3042 of the mirror portion 3015.

In other words, when 50 V is input to the pad 3024 and 0 V is input to the pad 3026, about 50 V immediately under the contact portion 3039 and about 0 V immediately under the contact portion 3038 are obtained in the thin film of silicon 3042 of the mirror portion 3015. Thus, a potential distribution in which the potential slightly varies between the contact portions 3039 and 3038.

By the way, the potential at the bottom surface of the concave 3018 of the silicon substrate 3021 opposing to the bottom surface of the thin film of silicon 3042 of the mirror portion 3015 is 0 V, which is the ground potential, due to the conduction with the pad 3028. A potential difference between the thin film of silicon 3042 of the mirror portion 3015 and the bottom surface of the concave 3018 occurs, and Coulomb gravity occurs as a result. The Coulomb gravity has a distribution in accordance with the potential distribution within the thin film of silicon 3042 of the mirror portion 3015. Thus, torsional moment is generated with respect to the hinges 3022a and 3022b, and the entire mirror 15 is tilt-driven horizontally.

Next, the potentials of sinusoidal waves having opposite phases to each other or sawtooth waves are input to the pads 3025 and 3027. Because of the input of the potentials, Coulomb gravity occurs between the thin film of silicon 3042 of the mirror support 3019 and the concave 3018 of the silicon substrate 3021 like the mirror portion 3015. Thus, the mirror support 3019 generates torsial moment with respect to the hinges 3020a and 3020b, and the mirror support 3019 is tilt-driven.

Because of the tilt-driving of the mirror portion 3015 and the mirror support 3019, observation light or light reflected by the mirror portion 3015 is reflected by the reflective films 3029 and 3030 on the surface of the mirror portion 3015. Since only the reflective portions 3029 and 3030 are provided on the surface of the mirror portion 3015, unnecessary noise light is not generated.

On the other hand, the light reflected especially by the wires 3031 to 3034 of light reflected by the mirror support 3019 supporting the mirror portion 3015 is optical noise. However, since the surfaces of the wires 3031 to 3034 in the mirror support 3019 are covered with the titan nitride 3048, the reflectivity is reduced. Thus, the optical noise can be reduced.

In other words, the reflectivity of the titan nitride 3048 is lower than the reflectivity of the base substrate silicon nitride film 3044 of the scan mirror 3014. By covering the aluminum 3049 of the wires 3031 to 3034 with the titan nitride 3048 having the lower reflectivity than that of the silicon nitride film 3044, the light reflection by the wires 3031 to 3034 is significantly reduced. Thus, an optical image capturing apparatus can be provided which does not easily generate optical noise by the scan mirror 3014. The potential supply can be easier for controlling over tilt-driving of the scan mirror 3014.

In the optical image capturing apparatus according to the first embodiment of the invention, the reflective films 3029 and 3030 of the mirror portion 3015 have a two-layer thin film construction having the chrome 3047 and the gold 3046. The wires 3031 to 3034 have a two-layer construction having the aluminum 3049 and the titan nitride 3048. The infinite numbers of combinations therebetween may be considered in accordance with a wavelength range of observation light to be used for observation.

For example, the wires 3031 to 3034 may have two-layer film of aluminum and chrome oxide. Furthermore, in the connection parts between the wire 3031 and the reflective film 3029 and between the wire 3033 and the reflective film 3030, the distal ends of the wires 3031 and 3033 may be provided on the reflective films 3029 and 3030.

Furthermore, when observation light has a visible light range, the wires 3031 to 3034 may contain chrome oxide having a lower reflectivity than that of the titan nitride 3048. When observation light is near-ultraviolet light around 300 nm, silver having a light-absorbing peak near 300 nm may be used. Thus, the reflectivity can be reduced to about 10%. Therefore, the reflective surfaces 3029 and 3030 may contain aluminum, and the wires 3031 to 3034 may be a silver thin film. Furthermore, the surface of the silver thin film may be exposed. Alternatively, the wires 3031 to 3035 may be a thin film of resin containing a large amount of carbon. As a result, the optical noise can be reduced. Furthermore, by using a one-layer construction also for a conductive function, the assembly efficiency can be improved.

The wires 3031 to 3034 may have a tree-layer construction having an anti-reflection film coated on a two-layer construction of aluminum and titan nitride. Thus, the reflectivity can be further reduced.

Twenty Seventh Embodiment

A twenty seventh embodiment of an optical image capturing apparatus according to the invention will be described with reference to FIG. 80. FIG. 80 is a plan view showing a configuration of a scan mirror used in the twenty seventh embodiment of the optical image capturing apparatus according to the invention. The same reference numerals are given to the same components as those of FIG. 77, and the detail descriptions thereof will be omitted here.

As shown in FIG. 77, in the scan mirror 3014 according to the twenty sixth embodiment, the pads 3025 and 3027 are connected to the contact portions 3036 and 3037 of the mirror support 3019 through the wires 3032 and 3034. The wires 3032 and 3034 having a predetermined width on the mirror support 3019 follows the external form of the mirror support 3019.

As shown in FIG. 80, in a scan mirror 3014 according to the twenty seventh embodiment, wires 3032a and 3034a are substantially provided on the entire upper surface of a mirror support 3019. In other words, the wires 3032 and 3034 having a predetermined width are provided on the upper surfaces of the plate wafer substrate 3017a and hinges 3020a and 3020b from the pads 3025 and 3027. The wires 3032 and 3034 are connected to wires 3032a and 3034a substantially provided on the entire upper surface of the mirror support 3019. The wires 3032a and 3034a are provided closely to the vicinity of the periphery of the mirror portion 3015.

On the other hand, observation light is irradiated from the optical fiber 3011, is reflected by a fixed reflective mirror 3012 and is irradiated to the scan mirror 3014. Since the observation light has a strength distribution having a Gaussian curve, the maximum light strength can be obtained at the center of the mirror portion 3015 in the scan mirror 3014. As a result, the light strength decreases gradually from the center in the direction of the radius.

Therefore, the reflected light outside of a reflection effective diameter, which causes optical noise, is preferably reduced as the distance to the mirror portion 3015 decreases on the surface of the mirror support 3019. In other words, the irradiated light is desirably absorbed.

Therefore, like the twenty seventh embodiment, the wires 3032a and 3034a are provided substantially on the entire upper surface, to which the observation light is irradiated, of the mirror support 3019, and the wires 3032a and 3034a are covered by the titan nitride 3049. Thus, the light reflectivity of the mirror support 3019 can be significantly reduced.

In other words, since the titan nitride 3049 has a lower reflectivity than that of the silicon nitride film 3044 of the mirror support 3019, the light reflectivity of the mirror support 3019 of the twenty seventh embodiment is more improved than the mirror support 3019 of the twenty sixth embodiment. Thus, the optical noise can be further reduced.

Next, an operation for observing a subject within a body cavity by using the optical image capturing apparatus 3010 according to the invention will be described with reference to FIGS. 81 to 85.

First of all, an insertable probe-type optical image capturing apparatus using a forceps channel, for example, in an endoscope will be described with reference to FIGS. 81 to 83.

FIG. 81 is an explanatory diagram for illustrating a state that a probe-type optical image capturing apparatus according to the invention is being inserted through the channel of the endoscope. FIG. 82 is a section diagram showing a first construction of the distal end of the probe-type optical image capturing apparatus according to the invention. FIG. 83 is a section diagram showing a second construction of the distal end of the probe-type optical image capturing apparatus according to the invention.

As shown in FIG. 81, a probe-type optical image capturing apparatus 3061 is provided to be inserted through a channel provided from an operation portion 3060b of the endoscope 3060 to an insert portion 3060a by using the endoscope 3060. The endoscope 3060 includes an insert portion 3060a having objective optical means for capturing subject image within a body cavity by being inserted into the body cavity and an operation portion 3060b having eye-piece optical means, which is provided at the base end of the insert portion 3060a, for manipulating the insert portion 3060a and for observing a subject image captured by the objective optical means.

As shown in FIG. 82, in the first construction of a distal end portion 3061a of the probe-type optical image capturing apparatus 3061, the distal end of the probe 3065 contains the optical image capturing apparatus 3062 for scanning and irradiating observation light coaxially with the probe 3065. A potential supply cable and a universal code 3064 are connected to the optical image capturing apparatus 3062. The potential supply cable drives a scan mirror. The universal code 3064 has an optical fiber for guiding observation light irradiating a subject and being reflected from the subject.

The probe-type optical image capturing apparatus 3061 having the construction is inserted through the channel of the endoscope 3060. Observation light 3063, for example, is irradiated from the optical image capturing apparatus 3062 in the distal end portion 3061a of the probe 3065 to a subject. The observation light 3063 is scanned like observation light 3063a indicated by the shown dashed line by tilt-driving the scan mirror of the optical image capturing apparatus 3062.

In other words, in order to observe a subject under the endoscope 3060, observation light may be scan-irradiated to the subject by using the probe-type optical image capturing apparatus 3061. Thus, a sectional image of the subject can be observed.

With the first construction of the distal end portion 3061a of the probe-type optical image capturing apparatus 3061 shown in FIG. 82, observation light can be irradiated coaxially with the probe 3065. On the other hand, a distal end portion 3061a' of the probe-type optical image capturing apparatus 3061 shown in FIG. 83 has an optical image capturing apparatus 3066 for scan-irradiating observation light in a direction orthogonal to the axial direction of the probe 3065. In other words, shown observation light beams 3067 and 3067a from the optical image capturing apparatus 3066 are scan-irradiated in the direction orthogonal to the axial direction of the probe 3065. Thus, a sectional image of a subject within a body cavity orthogonal to a insert direction of the endoscope 3060 and the probe type optical image capturing apparatus 3061 can be observed.

Next, an optical image capturing apparatus having the probe-type optical image capturing apparatus and an endoscope integrally will be described with reference to FIGS. 84 and 85.

The endoscope 3070 includes an insert portion 3071a to be inserted into a body cavity and an operation portion 3071b, which is provided at the base end of the insert portion 3071a, for manipulating the insert portion 3071a.

As shown in FIG. 85, the optical image capturing apparatus 3010 is provided coaxially with the insert portion 3071a in the distal end of the insert portion 3071a of the endoscope 3070. An illumination glass 3074 is provided on the front face of the optical image capturing apparatus 3010. Thus, the observation light from the optical image capturing apparatus 3010 is irradiated coaxially with the insert portion 3071a.

Furthermore, the objective lens 3072 and an image pickup element 3073 are provided in the distal end of the insert portion 3071a of the endoscope 3070. The image pickup element 3073 is provided at the image-forming position of the objective lens 3072. A subject image captured by the objective lens 3072 is output to the operation portion 3071b side as image pickup signals by the image pickup element 3073.

A universal cable 3075 such as a potential supply line for tilt-driving control over the scan mirror of the optical image capturing apparatus 3010, an optical fiber for guiding observation light and reflected light and a signal line for drive signals and image pickup signals for the image pickup element 3073 is provided from the insert portion 3071a to the operation portion 3071b. Furthermore, the universal cable 3075 is connected to a light source apparatus, an optical image creating apparatus, an image pickup signal processor and so on (not shown) from the operation portion 3071b.

In this way, by using an optical image capturing apparatus integrated with the probe-type optical image capturing apparatus and an endoscope, the optical image capturing apparatus 3010, 3062 and 3066 can be quickly driven, and required sectional images can be observed in order to observe a subject in a general diagnosis by using an endoscope and to observe a sectional image or three-dimensional images of the subject.

In this invention, it is apparent that various modifications different in a wide range can be made on this basis of this invention without departing from the spirit and scope of the invention. This invention is not restricted by any specific embodiment except being limited by the appended claims.

The invention claimed is:

1. An optical image pickup apparatus, comprising:
at least one light source;
a probe having at least one optical scanning means for scanning light emitted from the light source to a target;
waveform signal generating means for generating a drive waveform for driving the optical scanning means;
an optical system including first light transmitting means for irradiating light from the light source to the target and first optical detecting means for receiving return light from the target;
image creating means for converting the first light from the optical system to electric signals and creating images;
scanning permit generating means for generating a scanning permit signal for permitting driving of the optical scanning means;
scanning state detecting means for detecting a scanning state signal indicating a driving state of the optical scanning means; and
light source output control means for generating a light source output control signal and controlling the light source as far as all of the scanning permit signal and scanning state signal are valid;
wherein the probe has a probe connection connector removably connected to the signal generating means, and connection detecting means for detecting a connection state of the probe connection connector and generating a connection detection signal.

2. An optical image pickup apparatus according to claim 1, wherein the scanning state detecting means includes:
scanning frequency detecting means for detecting a scanning frequency of the optical scanning means; and
scanning width detecting means for detecting a scanning width of the optical scanning means, wherein, when the scanning frequency and/or the scanning width are equal to or lower than a predetermined value (predetermined values), the scanning state signal is invalid.

3. An optical image pickup apparatus according to claim 1, wherein the scanning permit signal includes a drive waveform output permit signal, which is generated by the waveform signal generating means, for permitting output of the drive waveform and a light source output permit signal, which is generated from a light source output permit control means for controlling output of the light source, wherein, when all of the drive waveform output permit signal and light source output permit signal are valid, the scanning permit signal is valid.

4. An optical image pickup apparatus according to claim 1, wherein the optical scanning means is a scanning mirror.

5. An optical image pickup apparatus according to claim 1, wherein the scanning state detecting means has form change detecting means for detecting a change in form of a movable part of the optical scanning means.

6. An optical image pickup apparatus according to claim 4, wherein the scanning state detecting means has electrostatic capacitance detecting means for detecting a change in electrostatic capacitance due to driving of the optical scanning means.

7. An optical image pickup apparatus according to claim 4, wherein the scanning minor is a micromachine mirror produced in a semiconductor process.

8. An optical image pickup apparatus according to claim 1, wherein at least a part of the scanning state detecting means is integrated with the optical scanning means.

9. An optical image pickup apparatus according to claim 1, wherein the probe has a flexible insert portion having a small diameter.

10. An optical image pickup apparatus according to claim 1, wherein the probe has a confocal optical system.

11. An optical image pickup apparatus comprising:
at least one light source;
a probe having at least one optical scanning means for scanning light emitted from the light source to a target;
waveform signal generating means for generating a drive waveform for driving the optical scanning means;
an optical system including first light transmitting means for irradiating light from the light source to the target and first optical detecting means for receiving return light from the target;
image creating means for converting the first light from the optical system to electric signals and creating images;
scanning permit generating means for generating a scanning permit signal for permitting driving of the optical scanning means;
scanning state detecting means for detecting a scanning state signal indicating a driving state of the optical scanning means; and
light source output control means for generating a light source output control signal and controlling the light source as far as all of the scanning permit signal and scanning state signal are valid;
wherein the scanning state detecting means includes:
scanning frequency detecting means for detecting a scanning frequency of the optical scanning means; and
scanning width detecting means for detecting a scanning width of the optical scanning means, wherein, when the scanning frequency and/or the scanning width are equal to or lower than a predetermined value (predetermined values), the scanning state signal is invalid.

12. An optical image pickup apparatus comprising:
at least one light source;
a probe having at least one optical scanning means for scanning light emitted from the light source to a target;
waveform signal generating means for generating a drive waveform for driving the optical scanning means;
an optical system including first light transmitting means for irradiating light from the light source to the target and first optical detecting means for receiving return light from the target;
image creating means for converting the first light from the optical system to electric signals and creating images;
scanning permit generating means for generating a scanning permit signal for permitting driving of the optical scanning means;
scanning state detecting means for detecting a scanning state signal indicating a driving state of the optical scanning means; and
light source output control means for generating a light source output control signal and controlling the light source as far as all of the scanning permit signal and scanning state signal are valid;
wherein the scanning permit signal includes a drive waveform output permit signal, which is generated by the waveform signal generating means, for permitting output of the drive waveform and a light source output permit signal, which is generated from a light source output permit control means for controlling output of the light source,
wherein, when all of the drive waveform output permit signal and light source output permit signal are valid, the scanning permit signal is valid.

13. An optical image pickup apparatus comprising:
at least one light source;
a probe having at least one optical scanning means for scanning light emitted from the light source to a target;
waveform signal generating means for generating a drive waveform for driving the optical scanning means;
an optical system including first light transmitting means for irradiating light from the light source to the target and first optical detecting means for receiving return light from the target;
image creating means for converting the first light from the optical system to electric signals and creating images;
scanning permit generating means for generating a scanning permit signal for permitting driving of the optical scanning means;
scanning state detecting means for detecting a scanning state signal indicating a driving state of the optical scanning means; and
light source output control means for generating a light source output control signal and controlling the light source as far as all of the scanning permit signal and scanning state signal are valid;
wherein the scanning state detecting means has form change detecting means for detecting a change in form of a movable part of the optical scanning means.

14. An optical image pickup apparatus comprising:
at least one light source;
a probe having at least one optical scanning means for scanning light emitted from the light source to a target;
waveform signal generating means for generating a drive waveform for diving the optical scanning means;

an optical system including first light transmitting means for irradiating light from the light source to the target and first optical detecting means for receiving return light from the target;

image creating means for converting the first light from the optical system to electric signals and creating images;

scanning permit generating means for generating a scanning permit signal for permitting driving of the optical scanning means;

scanning state detecting means for detecting a scanning state signal indicating a driving state of the optical scanning means; and light source output control means for generating a light source output control signal and controlling the light source as far as all of the scanning permit signal and scanning state signal are valid;

wherein the optical scanning means is a scanning mirror and the scanning state detecting means has electrostatic capacitance detecting means for detecting a change in electrostatic capacitance due to driving of the optical scanning means.

* * * * *